US012421321B2

(12) United States Patent
Bhargava et al.

(10) Patent No.: US 12,421,321 B2
(45) Date of Patent: Sep. 23, 2025

(54) METHODS FOR TREATING FIBRODYSPLASIA OSSIFICANS PROGRESSIVA

(71) Applicant: Ashibio, Inc., Brisbane, CA (US)

(72) Inventors: Pankaj Bhargava, Redwood City, CA (US); Victoria Smith, Burlingame, CA (US)

(73) Assignee: Ashibio, Inc., Brisbane, CA (US)

( * ) Notice: Subject to any disclaimer, the term of this patent is extended or adjusted under 35 U.S.C. 154(b) by 0 days.

(21) Appl. No.: 19/034,098

(22) Filed: Jan. 22, 2025

(65) Prior Publication Data

US 2025/0163184 A1    May 22, 2025

Related U.S. Application Data

(63) Continuation of application No. PCT/US2024/049868, filed on Oct. 3, 2024.

(60) Provisional application No. 63/699,035, filed on Sep. 25, 2024, provisional application No. 63/542,679, filed on Oct. 5, 2023.

(51) Int. Cl.
  *C07K 16/40* (2006.01)
  *A61P 19/00* (2006.01)
  *A61P 21/00* (2006.01)
  *A61K 39/00* (2006.01)

(52) U.S. Cl.
  CPC .............. *C07K 16/40* (2013.01); *A61P 19/00* (2018.01); *A61P 21/00* (2018.01); *A61K 2039/505* (2013.01); *A61K 2039/545* (2013.01); *C07K 2317/56* (2013.01)

(58) Field of Classification Search
  None
  See application file for complete search history.

(56) References Cited

U.S. PATENT DOCUMENTS

| 8,377,443 B2* | 2/2013 | McCauley | A61P 35/04 530/388.1 |
| 9,550,836 B2 | 1/2017 | Smith et al. | |
| 10,800,857 B2 | 10/2020 | Smith et al. | |

FOREIGN PATENT DOCUMENTS

WO   WO-2023192880 A2 * 10/2023 ........... A61K 31/197

OTHER PUBLICATIONS

Schroeder et al. (J Allergy Clin Immunol 2010, 125:S41-S52).*
Lloyd et al. (Protein Engineering, Design & Selection 2009, 22:159-168).*
Rudikoff et al. (Proc Natl Acad Sci USA 1982 vol. 79 p. 1979).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Piche-Nicholas et al. MABS 2018, 10:81-94.*
A Study of Andecaliximab in Participants With Fibrodysplasia Ossificans Progressiva (FOP) (ANDECAL) clinical study first posted on Jul. 18, 2024, includes results first posted on Dec. 18, 2024 (18 pages).
Agarwal, S., Loder, S. J., Breuler, C., Li, J., Cholok, D., Brownley, C., Peterson, J., Hsieh, H. H., Drake, J., Ranganathan, K., Niknafs, Y. S., Xiao, W., Li, S., Kumar, R., Tompkins, R., Longaker, M. T., Davis, T. A., Yu, P. B., Mishina, Y., & Levi, B. Strategic Targeting of Multiple BMP Receptors Prevents Trauma-Induced Heterotopic Ossification. *Molecular therapy : the journal of the American Society of Gene Therapy* 2017, 25(8), 1974-1987.
Appleby, T. C.; Greenstein, A. E.; Hung, M.; Liclican, A.; Velasquez, M.; Villaseñor, A. G.; Wang, R.; Wong, M. H.; Liu, X.; Papalia, G. A.; Schultz, B. E.; Sakowicz, R.; Smith, V.; Kwon, H. J. Biochemical Characterization and Structure Determination of a Potent, Selective Antibody Inhibitor of Human MMP9. *Journal of Biological Chemistry* 2017, 292 (16), 6810-6820.
Bergers, G.; Brekken, R.; McMahon, G.; Vu, T. H.; Itoh, T.; Tamaki, K.; Tanzawa, K.; Thorpe, P.; Itohara, S.; Werb, Z.; Hanahan, D. Matrix Metalloproteinase-9 Triggers the Angiogenic Switch during Carcinogenesis. *Nat Cell Biol* 2000, 2 (10), 737-744 (22 pages).
Billings, P. C.; Yang, E.; Mundy, C.; Pacifici, M. Domains with Highest Heparan Sulfate-Binding Affinity Reside at Opposite Ends in BMP2/4 versus BMP5/6/7: Implications for Function. *Journal of Biological Chemistry* 2018, 293 (37), 14371-14383.
Bonilla-Fornés, S.; Galán-Ledesma, L.; Pérez, P. M.; Modamio-Høybjør, S.; Carbonell-Pérez, J. M.; Parrón-Pajares, M.; Heath, K. E.; Galán-Gómez, E. Early Clinical and Radiological Improvement in a Young Boy with Metaphyseal Anadysplasia Type 2. *European Journal of Medical Genetics* 2021, 64 (10), 104307 (5 pages).
Davis, E. L.; Sonnet, C.; Lazard, Z. W.; Henslee, G.; Gugala, Z.; Salisbury, E. A.; Strecker, E. V.; Davis, T. A.; Forsberg, J. A.; Davis, A. R.; Olmsted-Davis, E. A. Location-dependent Heterotopic Ossification in the Rat Model: The Role of Activated Matrix Metalloproteinase 9. *Journal Orthopaedic Research* 2016, 34 (11), 1894-1904.
Elkins, P. A., Ho, Y. S., Smith, W. W., Janson, C. A., D'Alessio, K. J., McQueney, M. S., Cummings, M. D., & Romanic, A. M. (2002). Structure of the C-terminally truncated human ProMMP9, a gelatin-binding matrix metalloproteinase. Acta crystallographica. Section D, Biological crystallography, 58(Pt 7), 1182-1192.

(Continued)

*Primary Examiner* — Sharon X Wen
(74) *Attorney, Agent, or Firm* — Pamela J. Sherwood; Bret E. Field; Bozicevic, Field & Francis LLP

(57) ABSTRACT

The present disclosure provides methods and compositions for treating non hereditary heterotopic ossification and genetic heterotopic ossification, such as fibrodysplasia ossificans progressive (FOP). Such methods are directed to MMP-9 inhibition in therapeutic applications.

15 Claims, 3 Drawing Sheets

Specification includes a Sequence Listing.

(56) References Cited

OTHER PUBLICATIONS

Evans, K. N.; Potter, B. K.; Brown, T. S.; Davis, T. A.; Elster, E. A.; Forsberg, J. A. Osteogenic Gene Expression Correlates With Development of Heterotopic Ossification in War Wounds. Clin Orthop Relat Res 2014, 472 (2), 396-404.
Fields G. B. (2019). The Rebirth of Matrix Metalloproteinase Inhibitors: Moving Beyond the Dogma. Cells, 8(9), 984 (24 pages).
Garg, P.; Vijay-Kumar, M.; Wang, L.; Gewirtz, A. T.; Merlin, D.; Sitaraman, S. V. Matrix Metalloproteinase-9-Mediated Tissue Injury Overrides the Protective Effect of Matrix Metalloproteinase-2 during Colitis. American Journal of Physiology-Gastrointestinal and Liver Physiology 2009, 296 (2), G175-G184.
Gossage, D. L.; Cieslarová, B.; Ap, S.; Zheng, H.; Xin, Y.; Lal, P.; Chen, G.; Smith, V.; Sundy, J. S. Phase 1b Study of the Safety, Pharmacokinetics, and Disease-Related Outcomes of the Matrix Metalloproteinase-9 Inhibitor Andecaliximab in Patients With Rheumatoid Arthritis. Clinical Therapeutics 2018, 40 (1), 156-165.e5 (16 pages).
Hatsell, S. J.; Idone, V.; Wolken, D. M. A.; Huang, L.; Kim, H. J.; Wang, L.; Wen, X.; Nannuru, K. C.; Jimenez, J.; Xie, L.; Das, N.; Makhoul, G.; Chernomorsky, R.; D'Ambrosio, D.; Corpina, R. A.; Schoenherr, C. J.; Feeley, K.; Yu, P. B.; Yancopoulos, G. D.; Murphy, A. J.; Economides, A. N. ACVR1$^{R206H}$ Receptor Mutation Causes Fibrodysplasia Ossificans Progressiva by Imparting Responsiveness to Activin A. Sci. Transl. Med. 2015, 7 (303).
Hawinkels, L. J. A. C.; Zuidwijk, K.; Verspaget, H. W.; De Jonge-Muller, E. S. M.; Duijn, W. V.; Ferreira, V.; Fontijn, R. D.; David, G.; Hommes, D. W.; Lamers, C. B. H. W.; Sier, C. F. M. Vegf Release by MMP-9 Mediated Heparan Sulphate Cleavage Induces Colorectal Cancer Angiogenesis. European Journal of Cancer 2008, 44 (13), 1904-1913 (11 pages).
Hwang, C.; Pagani, C. A.; Das, N.; Marini, S.; Huber, A. K.; Xie, L.; Jimenez, J.; Brydges, S.; Lim, W. K.; Nannuru, K. C.; Murphy, A. J.; Economides, A. N.; Hatsell, S. J.; Levi, B. Activin A Does Not Drive Post-Traumatic Heterotopic Ossification. Bone 2020, 138, 115473 (10 pages).
Itoh, T.; Matsuda, H.; Tanioka, M.; Kuwabara, K.; Itohara, S.; Suzuki, R. The Role of Matrix Metalloproteinase-2 and Matrix Metalloproteinase-9 in Antibody-Induced Arthritis. The Journal of Immunology 2002, 169 (5), 2643-2647 (6 pages).
Kalev-Altman, R.; Janssen, J. N.; Ben-Haim, N.; Levy, T.; Shitrit-Tovli, A.; Milgram, J.; Shahar, R.; Sela-Donenfeld, D.; Monsonego-Ornan, E. The Gelatinases, Matrix Metalloproteinases 2 and 9, Play Individual Roles in Skeleton Development. Matrix Biology 2022, 113, 100-121.
Kessenbrock, K., Plaks, V., & Werb, Z. (2010). Matrix metalloproteinases: regulators of the tumor microenvironment. Cell, 141(1), 52-67 (30 pages).
Knight, C. G., Willenbrock, F., & Murphy, G. (1992). A novel coumarin-labelled peptide for sensitive continuous assays of the matrix metalloproteinases. FEBS letters, 296(3), 263-266.
Lausch, E.; Keppler, R.; Hilbert, K.; Cormier-Daire, V.; Nikkel, S.; Nishimura, G.; Unger, S.; Spranger, J.; Superti-Furga, A.; Zabel, B. Mutations in MMP9 and MMP13 Determine the Mode of Inheritance and the Clinical Spectrum of Metaphyseal Anadysplasia. The American Journal of Human Genetics 2009, 85 (2), 168-178.
Lees-Shepard, J. B.; Yamamoto, M.; Biswas, A. A.; Stoessel, S. J.; Nicholas, S.-A. E.; Cogswell, C. A.; Devarakonda, P. M.; Schneider, M. J.; Cummins, S. M.; Legendre, N. P.; Yamamoto, S.; Kaartinen, V.; Hunter, J. W.; Goldhamer, D. J. Activin-Dependent Signaling in Fibro/Adipogenic Progenitors Causes Fibrodysplasia Ossificans Progressiva. Nat Commun 2018, 9 (1), 471 (14 pages).
Li, S.; Shimono, C.; Norioka, N.; Nakano, I.; Okubo, T.; Yagi, Y.; Hayashi, M.; Sato, Y.; Fujisaki, H.; Hattori, S.; Sugiura, N.; Kimata, K.; Sekiguchi, K. Activin A Binds to Perlecan through Its Pro-Region That Has Heparin/Heparan Sulfate Binding Activity. Journal of Biological Chemistry 2010, 285 (47), 36645-36655.

Lounev, V.; Groppe, J. C.; Brewer, N.; Wentworth, K. L.; Smith, V.; Xu, M.; Schomburg, L.; Bhargava, P.; Al Mukaddam, M.; Hsiao, E. C.; Shore, E. M.; Pignolo, R. J.; Kaplan, F. S. Matrix Metalloproteinase-9 Deficiency Confers Resilience in Fibrodysplasia Ossificans Progressiva in a Man and Mice. Journal of Bone and Mineral Research 2024, 39 (4), 382-398 (17 pages).
Marshall, D. C.; Lyman, S. K.; McCauley, S.; Kovalenko, M.; Spangler, R.; Liu, C.; Lee, M.; O'Sullivan, C.; Barry-Hamilton, V.; Ghermazien, H.; Mikels-Vigdal, A.; Garcia, C. A.; Jorgensen, B.; Velayo, A. C.; Wang, R.; Adamkewicz, J. I.; Smith, V. Selective Allosteric Inhibition of MMP9 Is Efficacious in Preclinical Models of Ulcerative Colitis and Colorectal Cancer. PLoS One 2015, 10 (5), e0127063 (26 pages).
Ogata, Y., Itoh, Y., & Nagase, H. (1995). Steps involved in activation of the pro-matrix metalloproteinase 9 (progelatinase B)-tissue inhibitor of metalloproteinases-1 complex by 4-aminophenylmercuric acetate and proteinases. The Journal of biological chemistry, 270(31), 18506-18511.
Peterson, J. R., Agarwal, S., Brownley, R. C., Loder, S. J., Ranganathan, K., Cederna, P. S., Mishina, Y., Wang, S. C., & Levi, B. (2015). Direct Mouse Trauma/Burn Model of Heterotopic Ossification. Journal of visualized experiments : JoVE, (102), e52880 (5 pages).
Sandborn, W. J.; Bhandari, B. R.; Fogel, R.; Onken, J.; Yen, E.; Zhao, X.; Jiang, Z.; Ge, D.; Xin, Y.; Ye, Z.; French, D.; Silverman, J. A.; Kanwar, B.; Subramanian, G. M.; McHutchison, J. G.; Lee, S. D.; Shackelton, L. M.; Pai, R. K.; Levesque, B. G.; Feagan, B. G. Randomised Clinical Trial: A Phase 1, Dose-ranging Study of the Anti-matrix Metalloproteinase-9 Monoclonal Antibody GS-5745 versus Placebo for Ulcerative Colitis. Aliment Pharmacol Ther 2016, 44 (2), 157-169.
Sandborn, W. J.; Bhandari, B. R.; Randall, C.; Younes, Z. H.; Romanczyk, T.; Xin, Y.; Wendt, E.; Chai, H.; McKevitt, M.; Zhao, S.; Sundy, J. S.; Keshav, S.; Danese, S. Andecaliximab [Anti-Matrix Metalloproteinase-9] Induction Therapy for Ulcerative Colitis: A Randomised, Double-Blind, Placebo-Controlled, Phase 2/3 Study in Patients With Moderate to Severe Disease. Journal of Crohn's and Colitis 2018 12(9):1021-1029.
Shah, M. A.; Starodub, A.; Sharma, S.; Berlin, J.; Patel, M.; Wainberg, Z. A.; Chaves, J.; Gordon, M.; Windsor, K.; Brachmann, C. B.; Huang, X.; Vosganian, G.; Maltzman, J. D.; Smith, V.; Silverman, J. A.; Lenz, H.-J.; Bendell, J. C. Andecaliximab/GS-5745 Alone and Combined with mFOLFOX6 in Advanced Gastric and Gastroesophageal Junction Adenocarcinoma: Results from a Phase I Study. Clinical Cancer Research 2018, 24 (16), 3829-3837.
Shi, W.-Z.; Ju, J.-Y.; Xiao, H.-J ; Xue, F.; Wu, J.; Pan, M.-M.; Ni, W.-F. Dynamics of MMP-9, MMP-2 and TIMP-1 in a Rat Model of Brain Injury Combined with Traumatic Heterotopic Ossification. Molecular Medicine Reports 2017, 15 (4), 2129-2135.
Strong, A. L.; Spreadborough, P. J.; Dey, D.; Yang, P.; Li, S.; Lee, A.; Haskins, R. M.; Grimm, P. D.; Kumar, R.; Bradley, M. J.; Yu, P. B.; Levi, B.; Davis, T. A. BMP Ligand Trap ALK3-Fc Attenuates Osteogenesis and Heterotopic Ossification in Blast-Related Lower Extremity Trauma. Stem Cells and Development 2021, 30 (2), 91-105.
Tomkinson, A.; Moores, S.; Adamo-Trigiani, M.; Guillot, M.; Bienvenue, J.; Robinson, K.; Burns-Naas, L. Endochondral Ossification in Developing Long Bones of F1 Offspring Following Administration of Andecaliximab to F0 Dams During Gestation and Lactation. Poster 2764, 57th Annual Meeting of the Society of Toxicology, Mar. 11-15, 2018, San Antonio, Texas.
Van Wart, H. E., & Birkedal-Hansen, H. The cysteine switch: a principle of regulation of metalloproteinase activity with potential applicability to the entire matrix metalloproteinase gene family. Proceedings of the National Academy of Sciences of the United States of America 1990, 87(14), 5578-5582.
Vandooren, J.; Van Den Steen, P. E.; Opdenakker, G. Biochemistry and Molecular Biology of Gelatinase B or Matrix Metalloproteinase-9 (MMP-9): The next Decade. Critical Reviews in Biochemistry and Molecular Biology 2013, 48 (3), 222-272 (52 pages).
Velasquez, M.; O'Sullivan, C.; Brockett, R.; Mikels-Vigdal, A.; Mikaelian, I.; Smith, V.; Greenstein, A. E. Characterization of

(56) References Cited

OTHER PUBLICATIONS

Active MMP9 in Chronic Inflammatory Diseases Using a Novel Anti-MMP9 Antibody. *Antibodies* 2023, 12 (1), 9 (13 pages).

Vu, T. H.; Shipley, J. M.; Bergers, G.; Berger, J. E.; Helms, J. A.; Hanahan, D.; Shapiro, S. D.; Senior, R. M.; Werb, Z. MMP-9/Gelatinase B Is a Key Regulator of Growth Plate Angiogenesis and Apoptosis of Hypertrophic Chondrocytes. *Cell* 1998, 93 (3), 411-422 (21 pages).

Yang, E.; Mundy, C.; Rappaport, E. F.; Pacifici, M.; Billings, P. C. Identification and Characterization of a Novel Heparan Sulfate-Binding Domain in Activin A Longest Variants and Implications for Function. *PLoS One* 2019, 14 (9), e0222784 (24 pages).

\* cited by examiner

METHODS FOR TREATING FIBRODYSPLASIA OSSIFICANS PROGRESSIVA

CROSS-REFERENCE TO RELATED APPLICATIONS

This application is a continuation of International Patent Application No. PCT/US2024/049868, filed Oct. 3, 2024, which claims the benefit of and priority to U.S. Provisional Application No. 63/542,679, filed Oct. 5, 2023 and U.S. Provisional Application No. 63/699,035, filed Sep. 25, 2024, the entire disclosures of each of which are incorporated by reference herein in their entirety for all purposes.

SEQUENCE LISTING

This application contains a Sequence Listing which has been submitted electronically in XML format and is hereby incorporated by reference in its entirety. Said XML copy, created on Nov. 15, 2024, is named ASH-004WO_SL.xml and is 110,383 bytes in size.

FIELD OF THE DISCLOSURE

The present invention relates generally to the fields of treatment of disorders associated with extracellular matrix enzymes, proteases and administration of therapeutic or prophylactic compositions to remediate such disorders.

BACKGROUND

Matrix metalloproteinases (MMPs) are enzymes involved in extracellular matrix formation and remodeling. All MMPs share a conserved catalytic domain containing a zinc atom coordinated by three histidine residues. Types of MMPs include collagenases, gelatinases, stromelysins, matrilysins, enamelysins, and membrane MMPs. Structurally, MMP-9 is a gelatinase and as such has a signal peptide, propeptide, catalytic, zinc-binding and hemopexin-like domains common to MMPs, as well as a plurality of fibronectin-like domains and an O-glycosylated domain. MMP-9, in particular, has a hemopexin-like domain, catalytic domain, signal peptide, hinge region, and propeptide region. The catalytic domain of MMP-9 contains fibronectin type II (FN2) domains, an active site and a zinc-binding region, and the activity of the MMP-9 enzyme depends on zinc. MMPs are capable of degrading numerous extracellular matrix (ECM) components, as well as affecting cell-cell and cell-matrix interactions. MMP-9 is involved in many developmental processes, including ECM degradation, angiogenesis and formation of endochondral bone (for which it appears to play a unique role in the MMP family). MMP-9 in particular is found to be highly elevated in many human diseases, compared to limited expression in healthy tissues. Studies in knockout mice reveal opposing roles for MMP-9 and its most closely related MMP, MMP-2, the only other gelatinase. While loss of MMP-9 confers protection against disease in a variety of different models, loss of MMP-2 tends to lack this benefit and can even result in disease exacerbation. Substrates of MMP-9 include matrix proteins, growth factors, and cytokines. In addition to extracellular matrix remodeling, MMP-9 can render growth factors bioavailable (e.g., VEGF from heparin sulfate proteoglycans) or potentiate the activity of cytokines by cleavage. MMP-9 has also been shown to be involved in cell proliferation, migration, invasion, and epithelial-mesenchymal transition (EMT).

Numerous studies indicate MMPs as suitable targets to treat cardiovascular diseases, autoimmune diseases, and cancer. Despite concerted efforts to target MMPs, development of MMP inhibitors for various indications has been difficult, perhaps due to the conserved catalytic domain shared among the different MMPs. Small molecule inhibitors that target the catalytic domain not only affect a specific MMP implicated in pathogenesis, but also essential MMPs needed for normal functioning. For example, a broad spectrum MMP inhibitor was found to have musculoskeletal toxicity. Another broad-spectrum inhibitor, doxycycline, which is approved for the treatment of periodontal disease, appears to inhibit MMP-2 synthesis and activity.

Directed therapies are in development, such as andecaliximab—an anti-MMP-9 recombinant chimeric, humanized antibody that was evaluated in several clinical trials for a number of conditions including chronic obstructive pulmonary disease, gastric adenocarcinoma, Crohn's disease, rheumatoid arthritis, cystic fibrosis, various solid tumors, and ulcerative colitis. Andecaliximab binds MMP-9 in the catalytic domain at residue R162 and other residues near the cleavage site of the MMP-9 propeptide.

Fibrodysplasia ossificans progressiva (FOP) is a rare, autosomal dominant genetic condition characterized by worsening heterotopic ossification of the soft connective tissues. Approximately one in 1.3-2 million people worldwide is affected with FOP. Patients with FOP experience episodic flare-ups of inflammation in the soft tissues, occurring spontaneously or as a result of triggers including trauma, injury, illness, or immunization. These flare-ups can lead to heterotopic ossification of the soft tissues which over time causes increasing joint immobilization and disability. In certain cases, flare-ups can occur in the absence of subsequent heterotopic ossification.

MMP-9 could be playing several key roles in FOP. The mechanism of FOP centers on a highly recurrent autosomal dominant gain-of-function missense mutation in the ACVR1/ALK2 gene, ACVR1 R206H, encoding a BMP receptor. Activin A has been shown to be a critical ligand that promotes the differentiation of tissue-resident fibroadipogenic progenitors down a chondrocytic pathway in the context of ALK2 R206H. Activin A is not a canonical osteogenic BMP ligand and typically elicits pSMAD2/3 signaling through its receptors. However, unlike wild type ALK2, ALK2 R206H responds to Activin A, eliciting aberrant pSMAD1/5/8 (BMP-mothers against decapentagenic homolog 1/5/8) signaling, chondrogenesis and HO formation. The source of activin A appears to be inflammatory cells (e.g., macrophages) recruited to the prospective site of HO formation, and availability of Activin A has been proposed as a limiting factor for initiation of HO. In vivo studies indicate an ongoing requirement for Activin A by chondrocytes in nascent FOP lesions. Long splice forms of Activin A that are produced by inflammatory macrophages, and possibly also chondrocytes, associate with the heparin sulfate chains of perlecan which can serve to sequester Activin A in the extracellular matrix. Important MMP-9 substrates include extracellular matrix proteins such as heparan sulfate proteoglycans (HSPG) and fibrillin. The robust inflammation associated with FOP flares would induce both Activin A and MMP-9 expression, and MMP-9 could render Activin A bioavailable to drive aberrant chondrogenesis rather than normal tissue repair.

Additional roles for MMP-9 in FOP are possible. BMP signaling is matrix regulated, with tethering of BMP ligands (such as BMP2, 4, and others) to extracellular matrix proteins such as heparan sulfate proteoglycans (e.g., perlecan) and fibrillin, which constrains their activity. These proteins are MMP-9 substrates. For example, MMP-9 generates bioavailable VEGF by release from heparan sulfate proteoglycans. MMP-9 could promote BMP signaling via BMPs produced by both macrophages and early progenitors that differentiate into chondrocytes and continue to drive chondrocyte or osteoblast activation via provision of bioavailable BMPs. It could then further promote formation of bone via matrix remodeling, angiogenesis (including VEGF), and recruitment of other progenitors. MMP-9 could be playing additional roles in the recruitment and or activation of progenitors.

There are currently no curative treatments for FOP. Current treatments focus on glucocorticoids, nonsteroidal anti-inflammatory drugs, mast-cell inhibitors, leukotriene inhibitors, bisphosphonates at the outset of a flare-up to reduce inflammation. Prevention of flare-ups focuses on avoiding trauma and injury. Nongenetic HO commonly occurs after trauma or surgery. It occurs in up to 40% of hip arthroplasty cases, 30% of bone fracture or dislocation cases, high-energy extremity trauma, spinal cord injury, trauma, brain injuries, burns, fractures, muscle contusion, joint arthroplasty/replacement, hip surgery/replacement, acetabular surgery/replacement, elbow fracture, fracture of the long bones of the lower leg, combat-related trauma, amputation, neuromuscular blockade used to manage adult respiratory distress syndrome, and nontraumatic myelopathy, and other neurological disorders, and over 90% of severe traumatic amputations. (Meyers C, et al. Heterotopic Ossification: A Comprehensive Review. *JBMR Plus*. 3 (4) (2019): e10172. doi: 10.1002/jbm4.10172). Development of HO is also associated with predisposing, often pro-inflammatory, conditions such as axial spondylarthrites or ankylosing spondylitis and diffuse idiopathic skeletal hyperostosis (DISH). HO has also been described for patients experiencing serious complications as result of infection, such as SarsCoV2/COVID-19.

Heterotopic ossification occurs in one or more tissues selected from the group consisting of: bone, skin, subcutaneous tissue, skeletal muscle, tendon, ligament, aponeuroses, fibrotic tissue adjacent to joints, walls of blood vessels, and ligaments.

As disclosed in Hatsell et al., previous studies have shown that genetic variants of HO, such as fibrodysplasia ossificans progressiva (FOP), are caused by hyperactivating mutations of the type I bone morphogenetic protein receptor (T1-BMPR) ACVR1/ALK2, so studies evaluating therapies for HO have been directed primarily toward drugs for this specific receptor (Hatsell S J, et al., (2015). Sci Transl Med., 7 (303): 303ra137). However, patients with trauma-induced HO do not carry known T1-BMPR mutations. Although BMP signaling is required for NHHO, no single T1-BMPR (ACVR1/ALK2, BMPR1a/ALK3, or BMPR1b/ALK6) alone is necessary for the occurrence of this disease (Agarwal S, et al., (2017). Mol Ther, 25 (8): 1974-1987).

The present disclosure provides methods for treating hereditary forms of heterotopic ossification, such as fibrodysplasia ossificans progressiva by inhibiting MMP-9, thereby resulting in effective treatment or improved clinical outcomes in subjects with such disorders without the deleterious effects of broad-spectrum MMP inhibitors. In the case of FOP, the preferred therapy could be administered in early childhood and administration would continue life-long to reduce or prevent flares and accumulation of heterotopic ossification, both of which are difficult to predict.

SUMMARY OF THE INVENTION

Disclosed herein, in certain embodiments, are methods of treating a non-hereditary heterotopic ossification disorder and for treating a genetic heterotopic ossification (gHO), such as fibrodysplasia ossificans progressiva (FOP) by administering an effective amount of one or more MMP-9 inhibitors. In some embodiments, the MMP-9 inhibitor can be an anti-MMP-9 antibody or antigen-binding fragment thereof, an inhibitory RNA, an inhibitory polypeptide, a small molecule inhibitor, or a CRISPR-Cas system.

Disclosed herein, in certain embodiments, is a method of treating inflammatory flare-ups in a subject with fibrodysplasia ossificans progressiva (FOP), comprising administering to the subject an MMP-9 inhibitor. In certain embodiments, the inflammatory flare-ups are associated with heterotopic ossification in the subject. In certain embodiments, the inflammatory flare-ups are not associated with heterotopic ossification in the subject. In certain embodiments, the flare-ups are spontaneous or induced by an external trigger. In certain embodiments, the external trigger is selected from the group consisting of intra-muscular injections, biopsy, muscle fatigue, dental work, trauma, or infection. In certain embodiments, the external trigger is not known. In certain embodiments, the external trigger is heterotopic ossification in the subject. In certain embodiments, the method reduces the frequency of inflammatory flare-ups as compared to the frequency of inflammatory flare-ups prior to administering the MMP-9 inhibitor. In certain embodiments, the method reduces the severity of inflammatory flare-ups as compared to the severity of inflammatory flare-ups prior to administering the MMP-9 inhibitor.

Disclosed herein, in some embodiments, is a method of treating a gHO in a subject in need thereof, comprising administering to the subject a MMP-9 inhibitor.

In some embodiments, the MMP-9 inhibitor is selected from the group consisting of: an anti-MMP-9 antibody or antigen-binding fragment thereof, an inhibitory RNA, an inhibitory polypeptide, a small molecule inhibitor, and a CRISPR-Cas system. In some embodiments, the anti-MMP-9 antibody or antigen-binding fragment thereof is an anti-MMP-9 antibody or antigen-binding fragment thereof. In some embodiments, the anti-MMP-9 antibody or antigen-binding fragment thereof binds to: (i) an MMP-9 pro-form and inhibits activation of the pro-form; and/or (ii) an MMP-9 active form and inhibits activity of the active form. In some embodiments, the anti-MMP-9 antibody or antigen-binding fragment thereof binds to the MMP-9 pro-form. In some embodiments, the anti-MMP-9 antibody or antigen-binding fragment thereof binds to the active form of MMP-9. In some embodiments, the anti-MMP-9 antibody or antigen-binding fragment thereof comprises a heavy chain variable region (VH) comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a light chain variable region (VL) comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 7. In some embodiments, the anti-MMP-9 antibody or antigen-binding fragment thereof comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 7. In some embodiments, the anti-MMP-9 antibody or antigen-binding fragment thereof comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 55 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 7. In some embodiments, the anti-MMP-9 antibody or antigen-binding fragment thereof comprises a VH comprising an amino acid having at least 95% (e.g., at least 95%, 96%, 97%, 98%, 99%, or more) sequence identity to the amino acid sequence of SEQ ID NO: 55 and a VL comprising an amino acid sequence having at least 95% (e.g., at least 95%, 96%, 97%, 98%, 99%, or more) sequence identity to the amino acid sequence of SEQ ID NO: 7. In some embodiments, the anti-MMP-9 antibody or antigen-binding fragment thereof comprises a VH comprising an amino acid having at least 99% (e.g., at least 99%, or more) sequence identity to the amino acid sequence of SEQ ID NO: 55 and a VL comprising an amino acid sequence having at least 99% (e.g., at least 99%, or more) sequence identity to the amino acid sequence of SEQ ID NO: 7. In some embodiments, the anti-MMP-9 antibody or antigen-binding fragment thereof comprises a VH comprising an amino acid having 100% sequence identity to the amino acid sequence of SEQ ID NO: 55 and a VL comprising an amino acid sequence having 100% sequence identity to the amino acid sequence of SEQ ID NO: 7. In some embodiments, the anti-MMP-9 antibody or antigen-binding fragment thereof comprises andecaliximab or an antigen-binding fragment thereof. In some embodiments, the anti-MMP-9 antibody or antigen-binding fragment thereof comprises one or more amino acid sequences having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to any one of the amino acid sequences listed in Table 1. In some embodiments, the anti-MMP-9 antibody or antigen-binding fragment thereof comprises one or more amino acid sequences having at least 85% (e.g., at least 85%, 86%, 87%, 88%, 89%, 90%, 91%, 92%, 93%, 94%, 95%, 96%, 97%, 98%, 99%, or more) identity to any one of amino acid sequences listed in Table 1. In some embodiments, the anti-MMP-9 antibody or antigen-binding fragment thereof comprises one or more amino acid sequences having at least 90% (e.g., at least 90%, 91%, 92%, 93%, 94%, 95%, 96%, 97%, 98%, 99%, or more) identity to any one of amino acid sequences listed in Table 1. In some embodiments, the anti-MMP-9 antibody or antigen-binding fragment thereof comprises one or more amino acid sequences having at least 95% (e.g., at least 95%, 96%, 97%, 98%, 99%, or more) identity to any one of amino acid sequences listed in Table 1. In some embodiments, the anti-MMP-9 antibody or antigen-binding fragment thereof comprises one or more amino acid sequences having at least 99% (e.g., at least 99%, or more) identity to any one of amino acid sequences listed in Table 1. In some embodiments, the anti-MMP-9 antibody or antigen-binding fragment thereof comprises one or more amino acid sequences having 100% identity to any one of amino acid sequences listed in Table 1.

In some embodiments, the inhibitory RNA comprises an antisense oligonucleotide (ASO), a short interfering RNA (siRNA), a microRNA (miRNA), a short hairpin RNA (shRNA), or a shRNA-adapted microRNA (shmiRNA). In some embodiments, the inhibitory RNA comprises an ASO. In some embodiments, the inhibitory RNA comprises a siRNA. In some embodiments, the inhibitory RNA comprises a miRNA. In some embodiments, the inhibitory RNA comprises a shRNA. In some embodiments, the inhibitory RNA comprises a shmiRNA. In some embodiments, the inhibitory RNA comprises a nucleic acid sequence of any one of SEQ ID NOs: 63-80.

In some embodiments, the inhibitory RNA or the CRISPR-Cas system are formulated in a lipid nanoparticle (LNP).

In some embodiments, the method further comprises administration of an additional active agent or supportive therapy for treating gHO. In some embodiments, the additional active agent or supportive therapy for treating gHO is selected from the group consisting of: isotretinoin, etidronate with oral corticosteroids, perhexiline maleate, Activin-A inhibitor, Activin A Receptor Type 2 (ALK2) inhibitor, allele-specific RNA interference of ALK2, hypoxia inducible factor-1α (Hif-1α) inhibitor, small molecule inhibitor of Bone Morphogenetic Protein (BMP) signaling, anti-BMP9 antibody or antigen-binding fragment thereof, anti-BMP10 antibody or antigen-binding fragment thereof, anti-TGF-B antibody or antigen-binding fragment thereof, an IL1beta inhibitor, an IL6 inhibitor, momelotinib, chromolyn, imatinib, apyrase, rapamycin, a kinase inhibitor, saracatinib, palovarotene, retinoic acid receptor gamma agonists, retinoic acid receptor alpha agonists, bisphosphonates, radiation therapy, anti-inflammatory agents, physical therapy, and combinations thereof. In some embodiments, the additional active agent comprises a second MMP inhibitor selected from the group consisting of an MMP-2 inhibitor, an MMP-7 inhibitor, an MMP-13 inhibitor, an MMP-14 inhibitor, or an MMP-16 inhibitor. In some embodiments, the additional active agent or supportive therapy is administered concurrently with the MMP-9 inhibitor. In some embodiments, the additional active agent or supportive therapy is administered sequentially with the MMP-9 inhibitor.

In some embodiments, the gHO is FOP. In some embodiments, the gHO is characterized by endochondral ossification. In some embodiments, the gHO occurs in one or more tissues selected from the group consisting of bone, skin, subcutaneous tissue, skeletal muscle, tendon, ligament, aponeuroses, fibrotic tissue adjacent to joints, walls of blood vessels, and ligaments.

In some embodiments, the MMP-9 inhibitor is administered in a therapeutically effective amount. In some embodiments, administration of the MMP-9 inhibitor to the subject results in a reduction in symptoms selected form the group consisting of: a number of heterotopic ossifications, size of heterotopic ossifications, growth of heterotopic ossifications, or formation of heterotopic ossifications as compared to the symptoms in the subject prior to administration of the MMP-9 inhibitor.

In some embodiments, the subject has been identified as exhibiting formation of a gHO. In some embodiments, the subject has been identified as exhibiting formation of a gHO by way of a triple bone scan, computed tomography (CT) scan, or genetic analysis. In some embodiments, a genetic analysis identifies the subject as exhibiting formation of gHO by detecting a genetic mutation consistent with gHO.

In some embodiments, the MMP-9 inhibitor is an anti-MMP-9 antibody and is administered via subcutaneous administration at a dose of about 50 mg, about 100 mg, about 150 mg, about 200 mg, about 250 mg, about 300 mg, or about 400 mg.

In some embodiments, the subject is a human. In some embodiments, the subject is under about thirty years of age. In some embodiments, the subject is aged 12 years or above. In some embodiments, the antibody is administered weekly or every 2 weeks. In some embodiments, the subject is aged 18 years or above. In some embodiments, the subject is aged 6-12 years and the antibody is administered subcutaneously. In some embodiments, the subject is aged 2-5 years and the antibody is administered subcutaneously.

In preferred embodiments, the subject is of age greater than about 12 years and an MMP-9 inhibitor dose of 150 mg is administered every week. In another preferred embodiment, the subject is of age greater than about 12 years and an MMP-9 inhibitor dose of 50 mg is administered every week. In another preferred embodiment, the subject is aged between about 6 to about 11 years and an MMP-9 inhibitor dose of 75 mg is administered every week. In another preferred embodiment, the subject is aged between about 6 to about 11 years and an MMP-9 inhibitor dose of 25 mg is administered every week. In another preferred embodiment, the subject is aged between 2 and about 5 years and an MMP-9 inhibitor dose of 45 or 50 mg is administered every week. In another preferred embodiment, the subject is aged between 2 and about 5 years and an MMP-9 inhibitor dose of 15 mg is administered every week.

In preferred embodiments, the subject is aged between about 6 and about 11 years and an MMP-9 inhibitor dose of 75 mg is administered every week. In some embodiments, the subject is aged between about 6 and about 11 years and a dose of 25 mg is administered every week. In some embodiments, the subject is aged between about 2 and about 5 years and a dose of 50 or 45 mg is administered every other week. In some embodiments, the subject is aged 2-5 years and a dose of 15 mg is administered every other week. In some embodiments, the subject is aged 6-11 years and a dose of 75 mg is administered every other week. In some embodiments, the subject is aged 2-5 years and a dose of 45 or 50 mg is administered every other week.

In some embodiments, the subject has a gain-of-function mutation in the ACVR1/ALK2 gene. In some embodiments, the gain-of-function mutation the ACVR1/ALK2 gene is R206H.

In some embodiments, the MMP-9 inhibitor is administered by way of systemic delivery. In some embodiments, the systemic delivery comprises intravenous, intraarterial, intramuscular, subcutaneous, intraperitoneal, or intra-thoracic administration. In some embodiments, the MMP-9 inhibitor is administered by way of local delivery. In some embodiments, the local delivery comprises direct injection into an area of heterotopic ossification, a tissue, or an organ. In some embodiments, the MMP-9 inhibitor is administered once daily. In some embodiments, the MMP-9 inhibitor is administered to the subject for a duration that is between one month and 90 years. In some embodiments, administration of the MMP-9 inhibitor begins between the age of 2 and 18 and terminates between the age of 30 and 100.

In some embodiments, the MMP-9 inhibitor has no detectable inhibitory activity to human MMP-2.

Disclosed herein, in some embodiments, is a pharmaceutical composition comprising an inhibitory IgG4 antibody selective for matrix metalloproteinase-9 (MMP-9) with no detectable inhibitory activity to human MMP-2, in an amount effective to reduce heterotopic bone formation in a tissue selected from muscle, tendon, ligament, and fascia in a human subject under the age of about thirty and having a gain-of-function mutation in the ACVR1/ALK2 gene, when administered once daily by intravenous or subcutaneous administration to the human subject. In certain embodiments, detectable inhibitory activity is determined from lack of binding of the anti-MMP-9 antibody to MMP-2. In certain embodiments, no detectable binding of the anti-MMP-9 antibody to MMP-2 is observed in the presence of the anti-MMP-9 antibody at a concentration of up to 100 nM.

In some embodiments, the inhibitory IgG4 antibody comprises andecaliximab, and wherein the human subject comprises an R206H mutation in the ACVR1/ALK2 gene.

In some embodiments, the inhibitory IgG4 antibody comprises andecaliximab, and wherein the human subject has at least one symptom FOP.

Disclosed herein, in some embodiments, is a unit dosage comprising the pharmaceutical composition of the foregoing embodiments, wherein the inhibitory IgG4 antibody comprises andecaliximab, in an amount effective to reduce heterotopic bone formation in a tissue selected from muscle, tendon, ligament, and fascia by at least about 10% (e.g., at least about 10%, 20%, 30%, 40%, 50%, 60%, 70%, 80%, 90%, 95%, 99% or more) over a period of no greater than about four weeks in a human subject under the age of about thirty and having a gain-of-function mutation in the ACVR1/ALK2 gene, when administered once daily by intravenous or subcutaneous administration to the human subject. In some embodiments, the unit dosage is formulated for subcutaneous administration.

DETAILED DESCRIPTION

Definitions

Figure 1:
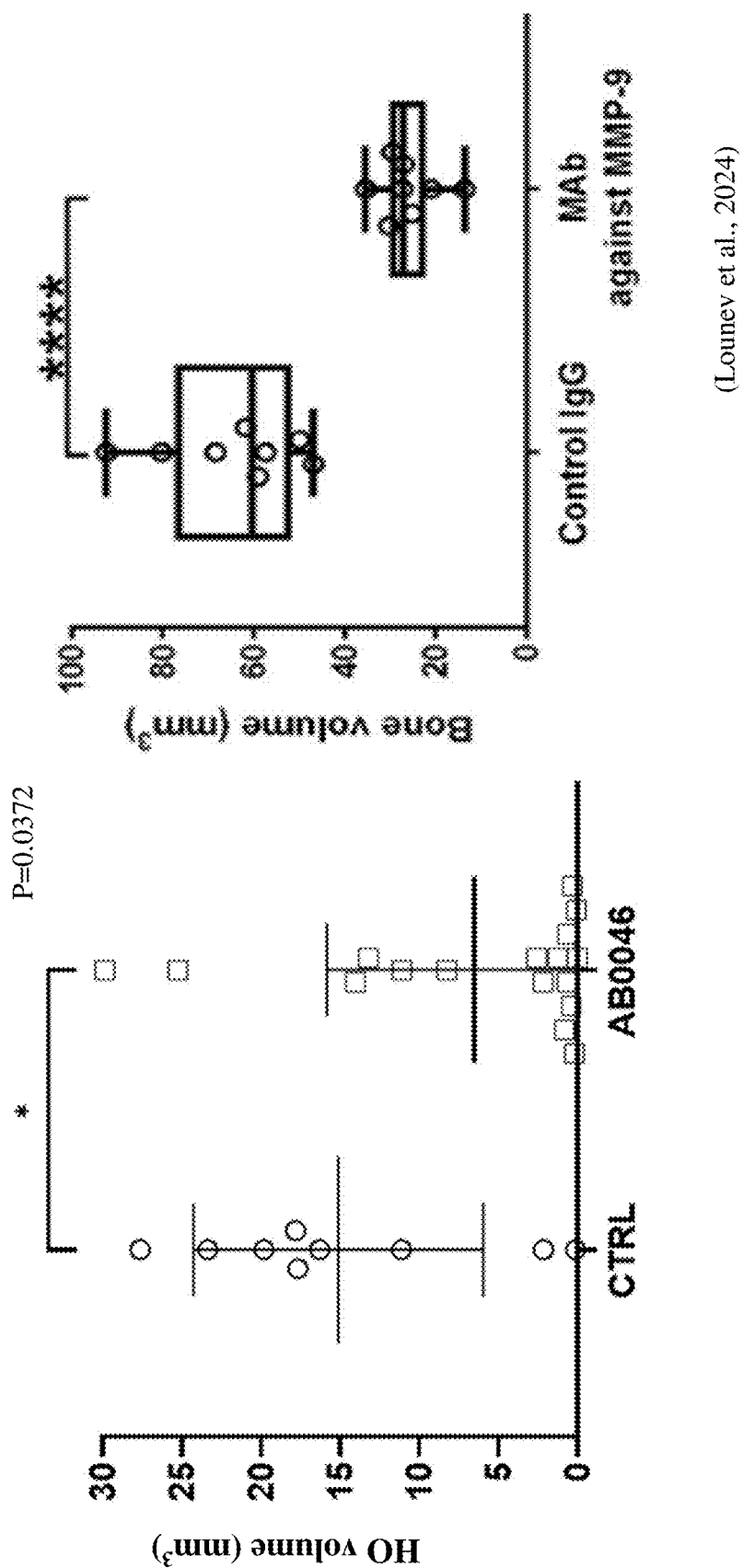
FIG. 1 is a plot showing heterotopic ossification (HO) in an inducible mouse model of FOP having the R206H mutation (Acvr1[R206H]FlEx/+, Gt(ROSA26)SorCre-ERT2/+) treated with a control vehicle or AB0046 antibody (murine surrogate of andecaliximab that recapitulates MMP-9 inhibitory activity). The induction of disease occurred via tamoxifen (75 mg/kg×7 days, IP) and cardiotoxin injection on day 0 (10 µM, 100 µL) in the right gastrocnemius muscle. Dosing occurred at 30 mg/kg three days prior to injury (loading dose to address initial target-mediated drug disposition), then 15 mg/kg on days 0 and 3, or 15 mg/kg continuing twice per week after day 3, via IP route via IP route. Ex vivo quantification of HO at the injury site was assessed using high-resolution micro CT and analyzed using 3D morphometry. In IgG control-treated mice, the amount of HO was shown to be significantly greater than in anti-MMP-9 antibody-treated mice (left panel), yielding consistent findings to that reported Lounev et al., 2024 (right panel). These results demonstrate that anti-MMP-9 antibody treatment reduced HO in mice.

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art.

The methods and techniques of the present invention are generally performed according to conventional methods well known in the art and as described in various general and more specific references that are cited and discussed throughout the present specification unless otherwise indicated.

All publications, patents and other references mentioned herein are hereby incorporated by reference in their entirety.

The following terms, unless otherwise indicated, shall be understood to have the following meanings:

Throughout this specification and claims, the word "comprise" or variations such as "comprises" or "comprising", will be understood to imply the inclusion of a stated integer or group of integers but not the exclusion of any other integer or group of integers.

The term "dosing" refers to the administration of one or more compositions (e.g., an anti-MMP-9 antibody) in a subject with the associated MMP-9 disorder.

The term "MMP-9 mediated disorder" generally refers to disease or conditions in which MMP-9 activity or expression is implicated or associated with one or more disease, or conditions.

The term "combination" therapy refers to the administration of one or more therapeutic compositions, e.g., a JAK inhibitor with an MMP-9 inhibitor or binding protein; or a BTK inhibitor with an MMP-9 inhibitor or binding protein; or a BMP receptor kinase inhibitor with an MMP-9 inhibitor or binding protein; or an MMP-9 inhibitor or binding protein with saracatinib; or an MMP-9 inhibitor or binding protein with a TNF inhibitor; or an inhibitor of another MMP, including, but not limited to, MMP-2, 7, 14, and/or 16, with a MMP-9 inhibitor or binding protein; or an inhibitor of the BMP signaling pathway, or an anti-TNF agent.

As used herein, the term "heterotopic ossification" or "HO" refers to the abnormal formation of bone in soft tissue where bone typically does not exist.

As used herein, the terms "inflammatory flare-up" or "flare-up" refer to a symptom of FOP characterized by soft-tissue swelling and inflammation. Flare-ups can be spontaneous or induced by an external trigger, such as intra-muscular injections, biopsy, muscle fatigue, dental work, trauma, or infection. In certain embodiments, the external trigger is not known. In certain embodiments, the external trigger for a flare-up is heterotopic ossification in the subject. Flare-ups occur more frequently in the neck, trunk, and upper limbs in patients below the age of 8, and more frequently in lower limbs thereafter. Flare-ups may be associated with subsequent heterotopic ossification, but may also occur in the absence of subsequent heterotopic ossification. Common symptoms associated with flare-ups include swelling, redness, warmth, stiffness, and decreased range of motion.

The term "polynucleotide" or "nucleic acid molecule" or "nucleotide sequence" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, and as an example for all sequences described herein under the general format, e.g., "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

As used herein, the term "heterotopic ossification" or "HO" refers to the abnormal formation of bone in soft tissue where bone typically does not exist. HO can be hereditary/genetic (gHO) or nonhereditary (NHHO). The focus of the present disclosure is treatment of gHO. gHO is a collection of rare autosomal dominant conditions presenting with new formation of bone in extraskeletal tissues. A non-limiting example of a gHO is fibrodysplasia ossificans progressiva (FOP).

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

In general, "stringent hybridization" is performed at about 25° C. below the thermal melting point I for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., Technique, 1:11-15 (1989) and Caldwell and Joyce, PCR Methods Applic. 2:28-33 (1992)); and "oligonucleotide-directed mutagenesis" (a process which enables the generation of site-specific mutations in any cloned DNA segment of interest; see, e.g., Reidhaar-Olson and Sauer, Science 241:53-57 (1988)).

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

The term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell and are thereby replicated along with the host genome. Moreover, certain preferred vectors are capable of directing the expression of genes to which they are operatively linked. Such vectors are referred to herein as "recombinant expression vectors" (or simply "expression vectors").

The term "operatively linked" or "operably linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The terms "peptide" or "polypeptide" as used herein refers to a short sequence of amino acid residues, e.g., one that is typically less than about 50 amino acids long and more typically less than about 30 amino acids long. The term as used herein encompasses analogs and mimetics that mimic structural and thus biological function. The terms "peptide" or "polypeptide" encompass both naturally-occurring and non-naturally-occurring proteins, and fragments, mutants, derivatives, and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}I$, $^{32}P$, $^{35}S$, and $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference).

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present invention have particular utility. The heterologous polypeptide included within the fusion protein of the present invention is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "non-peptide analog" refers to a compound with properties that are analogous to those of a reference polypeptide. A non-peptide compound may also be termed a "peptide mimetic" or a "peptidomimetic." See, e.g., Jones, *Amino Acid and Peptide Synthesis*, Oxford University Press (1992); Jung, *Combinatorial Peptide and Nonpeptide Libraries: A Handbook*, John Wiley (1997); Bodanszky et al., *Peptide Chemi-ry—A Practical Textbook*, Springer Verlag (1993); *Synthetic Peptides: A Users Guide*, (Grant, ed., W. H. Freeman and Co., 1992); Evans et al., *J. Med. Chem.* 30:1229 (1987); Fauchere, *J. Adv. Drug Res.* 15:29 (1986); Veber and Freidinger, *Trends Neurosci.*, 8:392-396 (1985); and references sited in each of the above, which are incorporated herein by reference. Such compounds are often developed with the aid of computerized molecular modeling. Peptide mimetics that are structurally similar to useful peptides of the present invention may be used to produce an equivalent effect and are therefore envisioned to be part of the present invention.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino and carboxy termini. A mutein may have the same but preferably has a different biological activity compared to the naturally-occurring protein. A mutein has at least 85% overall sequence homology to its wild-type counterpart. Even more preferred are muteins having at least 90%, 95%, 96%, 97%, 98%, 99% or higher overall sequence homology to the wild-type protein.

Sequence homology may be measured by any common sequence analysis algorithm, such as Gap or Bestfit.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (Golub and Gren eds., Sinauer Associates, Sunderland, Mass., $2^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The following six groups each contain amino acids that are conservative substitutions for one another: 1) Serine(S), Threonine (T); 2) Aspartic Acid (D), Glutamic AI (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (incorporated by reference herein). For example, percent sequence identity between amino acid sequences can be determined using FASTA with its default parameters (a word size of 2 and the PAM250 scoring matrix), as provided in GCG Version 6.1, herein incorporated by reference.

"Specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity) and antibody fragments as described herein. Bispecific antibodies are monoclonal and may be human or humanized antibodies that have binding specificities for at least two different antigens. In the context of the present disclosure, the two different binding specificities can be directed to two different MMPs, or to two different epitopes on a single MMP (e.g., MMP-9).

An antibody as disclosed herein can also be an immunoconjugate. Such immunoconjugates comprise an antibody (e.g., to MMP-9) conjugated to a second molecule, such as a reporter. An immunoconjugate can also comprise an antibody conjugated to a cytotoxic agent such as a chemotherapeutic agent, a toxin (e.g., an enzymatically active toxin of bacterial, fungal, plant, or animal origin, or fragments thereof), or a radioactive isotope (i.e., a radioconjugate). An antibody that "specifically binds to" or is "specific for" a particular polypeptide or an epitope on a particular polypeptide is one that binds to that particular polypeptide or epitope without substantially binding to any other polypeptide or polypeptide epitope. In some embodiments, an antibody of the present disclosure specifically binds to human MMP-9 with a dissociation constant (Kd) equal to or lower than 100 nM, optionally lower than 10 nM, optionally lower than 1 nM, optionally lower than 0.5 nM, optionally lower than 0.1 nM, optionally lower than 0.01 nM, or optionally lower than 0.005 nM; in the form of monoclonal antibody, scFv, Fab, or other form of antibody measured at a temperature of about 4° C., 25° C., 37° C. or 42° C.

An antibody can be human, humanized, chimeric, and/or affinity matured.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D., et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody", as used herein, is intended to refer to an antibody that is substantially free of other antibodies having different antigenic specificities (e.g., an isolated antibody that specifically binds MMP-9 is substantially free of antibodies that specifically bind antigens other than MMP-9). An isolated antibody that specifically binds MMP-9 may, however, have cross-reactivity to other antigens, such as MMP-9 molecules from other species. Moreover, an isolated antibody may be substantially free of other cellular material and/or chemicals.

An "antibody fragment" comprises a portion of a full-length antibody, for example, the antigen-binding or variable region of a full-length antibody. Such antibody fragments may also be referred to herein as "functional fragments" or "antigen-binding fragments". Examples of antibody fragments include Fab, Fab', F(ab')2, and Fv fragments; diabodies; linear antibodies (Zapata et al. (1995) Protein Eng. 8 (10): 1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F (ab')2 fragment that has two antigen combining sites and is still capable of cross-linking antigen.

"Fv" is the minimum antibody fragment which contains a complete antigen-recognition and antigen-binding site. This region consists of a dimer of one heavy and one light chain variable domain in tight, non-covalent association. It is in this configuration that the three complementarity-determining regions (CDRs) of each variable domain interact to define an antigen-binding site on the surface of the VH-VL dimer. Collectively, the six CDRs confer antigen-binding specificity to the antibody. However, even a single variable domain (or an isolated VH or VL region comprising only three of the six CDRs specific for an antigen) has the ability to recognize and bind antigen, although generally at a lower affinity than does the entire Fv fragment.

The "Fab" fragment also contains, in addition to heavy and light chain variable regions, the constant domain of the light chain and the first constant domain (CH1) of the heavy chain. Fab fragments were originally observed following papain digestion of an antibody. Fab' fragments differ from Fab fragments in that F (ab') fragments contain several additional residues at the carboxy terminus of the heavy chain CH1 domain, including one or more cysteines from the antibody hinge region. F (ab')2 fragments contain two Fab fragments joined, near the hinge region, by disulfide bonds, and were originally observed following pepsin digestion of an antibody. Fab'-SH is the designation herein for Fab' fragments in which the cysteine residue(s) of the constant domains bear a free thiol group. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to five major classes: IgA, IgD, IgE, IgG, and IgM, and several of these may be further divided into subclasses (isotypes), e.g., IgG1, IgG2, IgG3, IgG4, IgA1, and IgA2.

"Single-chain Fv" or "sFv" or "scFv" antibody fragments comprise the VH and VL domains of antibody, wherein these domains are present in a single polypeptide chain. In some embodiments, the Fv polypeptide further comprises a polypeptide linker between the VH and VL domains, which enables the sFv to form the desired structure for antigen binding. For a review of sFv, see Pluckthun, in The Pharmacology of Monoclonal Antibodies, vol. 113 (Rosenburg and Moore eds.) Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain, thereby creating two antigen-binding sites. Diabodies are additionally described, for example, in EP 404,097; WO 93/11161 and Hollinger et al. (1993) Proc. Natl. Acad. Sci. USA 90:6444-6448.

As used herein, the term "MMP-9 activation" refers to cleavage of the inactive pro-form of MMP-9 to produce the active form of MMP-9.

As used herein, the term "MMP-9 activity" refers to the enzymatic activity of the active form of MMP-9.

As used herein, the term "MMP-9 inhibitor" refers to an agent that inhibits or reduces MMP-9 activation, activity, or function. MMP-9 inhibitors include anti-MMP-9 inhibitory antibodies, small molecule inhibitors, RNA interference agents (e.g., siRNA), recombinant expression systems capable of knocking-out MMP-9 (e.g., CRISPR-Cas system), or other agents that inhibit or reduce MMP-9 expression, MMP-9 binding, MMP-9 function or activity. MMP-9 inhibitors reduce MMP-9 activation, activity, or function by 10% or more (e.g., 10%, 20%, 30%, 40%, 50%, 60%, 70%, 80%, 90%, 95%, 98% or more). The term "humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody comprises substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally comprises at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

Human antibodies can be produced, for example, by using phage display libraries. Hoogenboom et al. (1991) J. Mol. Biol, 227:381; Marks et al. (1991) J. Mol. Biol. 222:581. Other methods for preparing human monoclonal antibodies are described by Cole et al. (1985) "Monoclonal Antibodies and Cancer Therapy," Alan R. Liss, p. 77 and Boerner et al. (1991) J. Immunol. 147:86-95.

Human antibodies can also be made by introducing human immunoglobulin loci into transgenic animals (e.g., mice) in which the endogenous immunoglobulin genes have been partially or completely inactivated. Upon immunological challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al. (1992) Bio/Technology 10:779-783 (1992); Lonberg et al. (1994) Nature 368:856-859; Morrison (1994) Nature 368:812-813; Fishwald et al. (1996) Nature Biotechnology 14:845-851; Neuberger (1996) Nature Biotechnology 14:826; and Lonberg et al. (1995) Intern. Rev. Immunol. 13:65-93.

The term "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154 (7): 3310-9 (1995); and Hawkins et al, J. Mol. Biol. 226:889-896 (1992).

As used herein, the term "immunoadhesin" designates antibody-like molecules which combine the "binding domain" of a heterologous protein (an "adhesin", e.g. a receptor, ligand or enzyme) with the effector component of immunoglobulin constant domains. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as IgG1, IgG2, IgG3, or IgG4 subtypes, IgA, IgE, IgD or IgM.

The term "Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. The Fc sequence of an immunoglobulin generally comprises two constant domains, a CH2 domain and a CH3 domain, and optionally comprises a CH4 domain. By "Fc polypeptide" herein is meant one of the polypeptides that make up an Fc region. An Fc polypeptide may be obtained from any suitable immunoglobulin, such as IgG1, IgG2, IgG3, or IgG4 subtypes, IgA, IgE, IgD or IgM. In some embodiments, an Fc polypeptide comprises part or all of a wild type hinge sequence (generally at its N terminus). In some embodiments, an Fc polypeptide does not comprise a functional or wild type hinge sequence.

As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

The term "pharmaceutical formulation" refers to preparations of the active ingredients with one or more additional pharmaceutical agents, which can be found, for example, in in Remington: The Science and Practice of Pharmacy 21st ed., Lippincott Williams & Wilkins, 2005 (incorporated herein by reference).

"Pharmaceutically acceptable" excipients (vehicles, additives) are those which can reasonably be administered to a subject to provide an effective dose of the active ingredient employed.

The phrase "pharmaceutically acceptable carrier" is art recognized and includes a pharmaceutically acceptable material, composition or vehicle, suitable for administration to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient or subject.

A "stable" formulation is one in which the molecule, for example, the antibody composition essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993), for example. Stability can be measured at a selected temperature for a selected time period. In some embodiments, the formulation is stable at room temperature (about 30° C.) or at 40° C. for at least 1 month and/or stable at about 2-8° C. for at least 1 year, for at least 2 years. Furthermore, the formulation is preferably stable following freezing (to, e.g., −70° C.) and thawing of the formulation, hereinafter referred to as a "freeze/thaw cycle."

As used herein in reference to antibody compositions, an antibody "retains its physical stability" in a pharmaceutical formulation if it shows substantially no signs of aggregation, precipitation and/or denaturation upon visual examination of color and/or clarity, or as measured by UV light scattering or by size exclusion chromatography.

As used herein in reference to antibody compositions, an antibody "retains its chemical stability" in a pharmaceutical formulation, if the chemical stability at a given time is such that the antibody is considered to still retain its biological activity as defined below. Chemical stability can be assessed by detecting and quantifying chemically altered forms of the antibody. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example.

As used herein in reference to antibody compositions, an antibody "retains its biological activity" in a pharmaceutical formulation, if the antibody in a pharmaceutical formulation is biologically active for its intended purpose. For example, biological activity is retained if the biological activity of the antibody in the pharmaceutical formulation is within about 30%, about 20%, or about 10% (within the errors of the assay) of the biological activity exhibited at the time the pharmaceutical formulation was prepared (e.g., as determined in an antigen binding "assay). "Isotonic" is a term recognized in the art. Isotonic can mean, for example, that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example. A "tonicity agent" is a compound which renders the formulation isotonic.

As used herein, "buffer" refers to a buffered solution that resists changes in pH by the action of its acid-base conjugate components. The buffer of this invention has a pH in the range from about 4 to about 8; preferably from about 4.5 to about 7; and most preferably has a pH in the range from about 5.0 to about 6.5. Examples of buffers that will control the pH in this range include acetate (e.g. sodium acetate), succinate (such as sodium succinate), gluconate, histidine, citrate and other organic acid buffers.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

As used herein, the terms "NHHO" or "non-hereditary heterotopic ossification" or "NGHO" or "non-genetic heterotopic ossification" are used interchangeably and include a non-genetic condition of progressive formation of ectopic bone in soft tissues, often following trauma. Spinal cord and traumatic brain injuries, injuries associated with war or gunshots, and severe burns can give rise to the formation of extraskeletal bone in joints, muscles or tendons. Nongenetic heterotopic ossification can occur with essentially any musculoskeletal trauma, spinal cord injury, central nervous system injury, head injury, cerebrovascular accident, sickle cell anemia, hemophilia, tetanus, poliomyelitis, multiple sclerosis, toxic epidermal necrolysis, viral infections including COVID-19, and burns. Examples of musculoskeletal trauma include, but are not limited to, hip, knee, shoulder, or elbow arthroplasty; fractures; joint dislocations; or soft-tissue trauma, with the musculus quadriceps femoris and *Musculus brachialis*. Surgical removal often leads to the recurrence of HO, as does surgical intervention in some pre-disposing conditions involving chronic inflammation and bone formation, such as axial spondyloarthritis. NHHO can occur nearly anywhere in the body, but the most common areas include locations that are susceptible to trauma, such as the elbow, thigh, pelvis, and shoulder. NHHO can cause pain around the ossification site, loss of joint mobility and subsequently loss of function, as discussed in Myers C, et al., (2019). JBMR Plus, 3 (4): e10172. Examples of musculoskeletal trauma include, but are not limited to, hip, knee, shoulder, or elbow arthroplasty; fractures; joint dislocations; or soft-tissue trauma, with the musculus quadriceps femoris and musculus brachialis. Non-genetic heterotopic ossification can also be associated with fever, swelling, and erythema (e.g., local, patchy reddening of the skin). As a non-limiting example, NHHO is associated with one or more disorders or conditions selected from the group of spinal cord injury, trauma, brain injuries, burns, fractures, muscle contusion, joint arthroplasty/replacement, hip surgery/replacement, acetabular surgery/replacement, elbow fracture, fracture of the long bones of the lower leg, combat-related trauma, amputation, neuromuscular blockade used to manage adult respiratory distress syndrome, and nontraumatic myelopathy.

As used herein, the terms "triple bone scan" or a "three-phase bone scan" are used interchangeably and refer to the diagnostic procedure that includes a series of images that can show early bone disease, infection, or fractures. These conditions can be imaged with the scan before they can be seen on standard X-rays in many cases. This scan uses a small amount of radioactive material as a tracer that is absorbed into the bones and detected by a camera to result in an image.

As used herein, the term "prevention" refers to the treatment of at risk patients before the symptoms of HO (eg., NHHO or FOP) arise, to further prevent condition development.

As used herein, the term "tenotomy" refers to the surgical act which involves the division or severance of a tendon.

The term "ad libitum" as used herein, refer to having access to something as often or as necessary as desired. As a non-limiting example, in this application, the mice used in these experimental conditions have "ad libitum", or free access and availability to food and water.

The term "musculoskeletal disease or condition" or "MSD" refers to an injury, condition and/or pain in a subject's bones, joints, ligaments, muscles, nerves, tendons, and structures that support limbs, neck, and back.

As used herein, the terms "treatment," "treat" or "treating" refer to the medical management of a subject with the intent to improve, ameliorate, stabilize (i.e., not worsen), cure a disease, pathological condition, or disorder, and in some circumstances, a "treatment" may include the prevention of the disease, disorder or condition. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder or symptoms of the disease, pathological condition, or disorder); and supportive treatment (treatment employed to supplement another therapy). Treatment also includes diminishment of the extent of the disease or condition; preventing spread of the disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to have the condition or disorder or those in which the condition or disorder is to be prevented.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

As used herein, the term "therapeutically effective amount" or "effective amount" refers to an amount of a therapeutic composition that when administered alone or in combination with another therapeutic composition to a subject is effective to prevent or ameliorate the disease condition or the progression of the disease, e.g., genetic heterotopic ossification. The term also includes a prophylactically effective amount at dosages and for periods of time necessary, to achieve the desired prophylactic result. Typically, since a prophylactic dose is used in subjects prior to or at an earlier stage of disease, the prophylactically effective amount will be less than the therapeutically effective amount.

A "disorder" is any condition that would benefit from treatment with the antibody. This includes chronic and acute disorders or diseases including those pathological conditions which predisposes the subject to the disorder in question.

Actual dosage levels of the active ingredients (e.g., antibody, small molecule or peptide inhibitor, inhibitory nucleic acids, and CRISPR-Cas) in the pharmaceutical formulation of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the antibody found in the formulation, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition of the present invention required. For example, the physician or veterinarian could start doses of the compounds of the invention employed in the pharmaceutical formulation at levels lower than that required in order to achieve the desired therapeutic effect and gradually increase the dosage until the desired effect is achieved.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131;

and Johnson, B., et al. (1991) Anal. Biochem. 198:268-277. The term "$K_{off}$", as used herein, is intended to refer to the off rate constant for dissociation of an antibody from the antibody/antigen complex. The term "$K_d$", as used herein, is intended to refer to the dissociation constant of a particular antibody-antigen interaction.

The term, "$EC_{50}$," is intended to refer to the concentration of a substance (e.g., a compound or a drug) that is required for 50% activation or enhancement of a biological process, or component of a process. For example, EC 50 can refer to the concentration of agonist that provokes a response halfway between the baseline and maximum response in an appropriate assay of the target activity.

The term, "$IC_{50}$," is intended to refer to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay.

As used herein, the phrase "inhibitory nucleic acid" refers to any nucleic acid that, when administered interacts with a target gene, results in inhibition of the expression or activity of that target gene, e.g., MMP-9. A nucleic acid molecule that inhibits, i.e., an inhibitory nucleic acid may be DNA, or an inhibitory RNA (e.g., siRNA, miRNA, antisense oligonucleotide (ASO), shRNA, lncRNA, pre-miRNA, or miRNA), wherein the RNA is single stranded, double stranded, or contains both single stranded and double stranded regions. In some embodiments, an inhibitory nucleic acid is an siRNA. In some embodiments, an inhibitory nucleic acid is an antisense oligonucleotide (ASO). The ASO can be a single-stranded or double-stranded DNA, RNA, or DNA/RNA hybrid. See, e.g., Antisense Oligodeoxynucleotides and Antisense RNA: Novel Pharmacological and Therapeutic Agents, CRC Press, Boca Raton, Fla., 1997. It is understood that the compositions disclosed herein have certain desired functions, e.g., inhibit MMP-9 activity or activation to treat MMP-9 mediated disorders, e.g., genetic heterotopic ossification. Disclosed herein are methods and compositions of a number of therapeutic modalities for performing the disclosed functions, and it is understood that there are a variety of structures that can perform the same or similar function that are related to the methods and compositions, which are anticipated to achieve the same or similar result.

Unless otherwise defined, all technical and scientific terms used herein have the same meaning as commonly understood by one of ordinary skill in the art to which this present invention pertains. Exemplary methods and materials are described below, although methods and materials similar or equivalent to those described herein can also be used in the practice of the present disclosure and will be apparent to those of skill in the art. All publications and other references mentioned herein are incorporated by reference in their entirety. In case of conflict, the present specification, including definitions, will control. The materials, methods, and examples are illustrative only and not intended to be limiting.

In various aspects of the present invention, provided are methods and compositions for treating a subject by administering one or more inhibitors of MMP-9. In some embodiments, the methods described herein are used to treat genetic heterotopic ossification, such as fibrodysplasia ossificans progressiva (FOP).

Methods of Treatment
Selection of Subjects

Disclosed herein, in some embodiments, are methods of treating a subject identified as having a genetic heterotopic ossification (gHO), comprising administering to the subject a composition, such as a pharmaceutical composition comprising an MMP-9 inhibitor (e.g., anti-MMP-9 antibody or antigen-binding fragment thereof, inhibitory RNA, small molecule, inhibitory polypeptide, or a recombinant gene knock-out or knock-down system, such as a CRISPR-Cas system). In some embodiments, the disclosure provides a use an MMP-9 inhibitor as described herein for the manufacture of a medicament. In some embodiments, the disclosure provides a use of an antibody as described herein for the treatment of a gHO. In some embodiments, the gHO is fibrodysplasia ossificans progressiva (FOP).

In some embodiments, the subject is a mammal, such as a human. In some embodiments, the subject is under about thirty years of age. In some embodiments, the subject is aged 12 or above. In some embodiments, the subject is aged 18 or above. In some embodiments, the subject is aged 6-12. In some embodiments, the subject is aged 2-12. In some embodiments, the subject has a gain-of-function mutation in the ACVR1/ALK2 gene. In some embodiments, the gain-of-function mutation the ACVR1/ALK2 gene is R206H.

Heterotopic ossification is ectopic lamellar bone formation in soft tissues. (Ranganathan, K., Loder, S., Agarwal, S., Wong, V. W., Forsberg, J., Davis, T. A., Wang, S., James, A. W., and Levi, B., J Bone Joint Surg Am. 2015 Jul. 1; 97 (13): 1101-1111). Common causes of heterotopic ossification are joint arthroplasty, spinal cord injury, traumatic brain injury, blast trauma, elbow and acetabular fractures, and thermal injury. (Ranganathan, K., Loder, S., Agarwal, S., Wong, V. W., Forsberg, J., Davis, T. A., Wang, S., James, A. W., and Levi, B., J Bone Joint Surg Am. 2015 Jul. 1; 97 (13): 1101-1111). Factors affecting the cellular transition from progenitor cells to osteogenic precursor cells include oxygen tension, pH, availability of micronutrients, and mechanical stimuli. (Ranganathan, K., Loder, S., Agarwal, S., Wong, V. W., Forsberg, J., Davis, T. A., Wang, S., James, A. W., and Levi, B., J Bone Joint Surg Am. 2015 Jul. 1; 97 (13): 1101-1111). The condition has also been referred to as paraosteoarthropathy, myositis ossificans, periarticular new bone formation, periarticular ectopic ossification, neurogenic osteoma, neurogenic ossifying fibromyopathy and heterotopic calcification. (Sawyer J R, Myers M A, Rosier R N, Puzas J E. Heterotopic ossification: clinical and cellular aspects. Calcif Tissue Int 1991; 49:208-15).

The clinical signs of heterotopic ossification are pain, decreased range of motion, swelling or warmth in the joint area, increased spasticity, and fever. There is an absence of effective treatment, and heterotopic ossification can occur for unknown cause. Lisa Harvey BAppSc, GradDipAppSc (exSpSc), MAppSc, PhD, in Management of Spinal Cord Injuries, 2008.

Heterotopic ossification can be addressed prophylactically with non-steroidal anti-inflammatory drugs (NSAIDs) or radiation. (Ranganathan, K., Loder, S., Agarwal, S., Wong, V. W., Forsberg, J., Davis, T. A., Wang, S., James, A. W., and Levi, B., J Bone Joint Surg Am. 2015 Jul. 1; 97 (13): 1101-1111). To treat heterotopic ossification, surgery is sometimes recommended, though this is not an option when heterotopic ossification occurs in fibrodysplasia ossificans progressiva, an inherited form of heterotopic ossification. (Ranganathan, K., Loder, S., Agarwal, S., Wong, V. W., Forsberg, J., Davis, T. A., Wang, S., James, A. W., and Levi, B., J Bone Joint Surg Am. 2015 Jul. 1; 97 (13): 1101-1111). A putative mechanism has been proposed for heterotopic ossification. It is suggested that heterotopic ossification occurs through a progression beginning with injury or trauma to skeletal myocytes, followed by neuronal stimulation, release of Substance P, mast cell degranulation and inflammation, recruitment of myeloid cells and lymphocytes, and the release of TGFb and bone morphogenic proteins (BMPs). It is thought that TGFb and BMPs act on blood vessels, leading to endothelial-to-mesenchymal transition (EMT). Following EMT, endothelial mesenchymal stem-like cells (MSCs) and resident MSCs undergo chondrogenesis, followed by endochondral ossification, as well as osteogenesis.

MMP-9 induces EMT in human kidney glomerular endothelial cells via Notch activation. Without being bound by theory, it is believed herein that MMP-9 mediated disorders such as genetic heterotopic ossification (e.g., FOP) may be treated by preventing EMT. Accordingly, in some embodiments, disclosed herein are methods and compositions for treating a subject by administering one or more inhibitors of MMP-9 to prevent EMT and progression of heterotopic ossification.

In certain aspects of the invention, methods and compositions of the invention reduce BMP levels and/or BMP signaling in the subject. In further aspects of the invention, methods and compositions of the invention reduce BMP signaling in the context of inflammation and heterotopic ossification in soft tissues, joints, muscles, ligaments, bones and other sites of injury or inflammation. In some embodiments of the invention, the method reduces pathologic BMP signaling without impacting homeostatic BMP signaling.

Based on the Brooker system, heterotopic ossification is classified into four grades: I-IV. Patients with heterotopic ossification Brooker grade III and IV showed no improvement of passive range of motion of the hip joint in the postoperative follow-up.

Accordingly, it is an object of the invention to improve clinical outcomes in subjects with genetic heterotopic ossification (e.g., FOP) of higher degree (Brooker III, IV). In some embodiments, one or more therapies of the present invention are administered to reduce the higher degrees of genetic heterotopic ossification. In certain some embodiments, postoperative passive range of motion in subjects is improved. For instance, with respect to the hip joint, flexion, internal and external rotation, abduction and adduction movement are improved.

FOP is a genetic form of progressive heterotopic ossification in soft tissue and muscle. The most common genetic basis for FOP is an autosomal dominant gain of function missense mutation in the ACVR1/ALK2 gene, where a G to A substitution at nucleotide c.617 changes a CGC codon encoding arginine to CAC, encoding histidine (R206H). The R260H mutation occurs in the GS domain of ACVR1, thereby resulting in BMP binding of ACVR1 and overactivation of the SMAD 1/5/8 signaling pathway. In addition, Activin A binds R260H-mutated ACVR1, causing ACVR1 to phosphorylate SMAD 1/5/8 rather than SMAD 2/3. SMAD 1 and 5 contribute to the expression of osteoblastic differentiation factors in C2C12 cells when co-expressed with R260H-mutated ACVR1 and could play a role in heterotopic ossification in FOP.

The standard of care for FOP is treatment with glucocorticoids, NSAIDs, mast cell inhibitors, leukotriene inhibitors, or bisphosphonates. However, these treatments are not highly effective, and the main approach to managing FOP is avoiding injury, which is thought to initiate the progression to heterotopic ossification. It is, therefore, an object of the present disclosure to provide improved treatments for FOP.

Route of Administration

MMP-9 inhibitors suitable for use with the disclosed methods are formulated for any suitable route of administration to a subject including, but not limited to injection (e.g., intravenous injection), in some embodiments. Injection includes, e.g., subcutaneous, peritoneal, intravenous injection, or intramuscular injection. In some embodiments, the antibodies of the disclosure are formulated for subcutaneous administration. In some embodiments, the antibodies of the disclosure are formulated for peritoneal administration. In some embodiments, the antibodies of the disclosure are formulated for intravenous administration (e.g., intravenous injection or infusion). In some embodiments, the antibodies of the disclosure are formulated for intramuscular administration. In some embodiments, administration is in one, two, three, four, five, six, seven, or more injection sites. In some embodiments, administration is in one injection site. In some embodiments, administration is in two injection sites. In some embodiments, administration is in three injection sites. In some embodiments, administration is in four injection sites. In some embodiments, administration is in five injection sites. In some embodiments, administration is in six injection sites.

For in vivo applications, contacting occurs, e.g., via administration of a composition (e.g., a composition comprising an MMP-9 inhibitor) to a subject by any suitable means. An MMP-9 inhibitor disclosed herein, in some embodiments, is administered, e.g., either systemically or locally, including via parenteral, subcutaneous, intraperitoneal, intrapulmonary, and intranasal administration, and, if desired for local treatment, injection directly into the site of heterotopic ossification. Parenteral routes include, e.g., intravenous, intraarterial, intraperitoneal, epidural, intramuscular, and intrathecal administration. Such administration, in some embodiments, is as a bolus, continuous infusion, or pulse infusion. In some embodiments, compositions are administered by injection depending in part on whether the administration is brief or chronic. Other modes of administration methods are contemplated, including topical, particularly transdermal, transmucosal, rectal, oral, or local administration e.g., through a catheter placed close to the desired site.

Dosing

MMP-9 inhibitors suitable for use with the disclosed methods and compositions comprising the same may be administered in a manner compatible with the dosage formulation and in a therapeutically effective amount. The quantity to be administered depends on the subject to be treated, in some embodiments. Precise amounts of active ingredient required to be administered depend on the judgment of the practitioner and are peculiar to each subject. Suitable regimes for initial administration, but are typified by an initial administration followed by repeated doses at one hour intervals or longer by a subsequent administration. Alternatively, continuous administration that is sufficient to maintain concentrations in the blood are contemplated.

The amounts of the active ingredients (e.g., an MMP-9 inhibitor) in the compositions, the composition formulation, and the mode of administration, are among the factors that are varied to provide an amount of the active ingredient that is effective to achieve the desired therapeutic response for each subject, without being unduly toxic to the subject. The selected dosage level will depend upon a variety of factors including the activity of the particular compound employed, the route of administration, the time of administration, the rate of excretion or metabolism of the particular compound being employed, the duration of the treatment, other drugs, compounds and/or materials used in combination with the particular composition employed, the age, sex, weight, condition, general health, diet and prior medical history of the subject being treated, and like factors well known in the medical arts.

In some embodiments, an MMP-9 inhibitor suitable for use with the disclosed methods or a pharmaceutical composition comprising the same is administered to a subject in various dosing amounts and over various time frames. Additionally, the dose(s) of an MMP-9 inhibitor is administered, in some embodiments, twice a week, weekly, every two weeks, every three weeks, every 4 weeks, every 6 weeks, every 8 weeks, every 12 weeks, or any combination of weeks therein. Dosing cycles are also contemplated, such as, e.g., administering the MMP-9 inhibitor once or twice a week for 4 weeks, followed by two weeks without therapy. Additional dosing cycles including, e.g., different combinations of the doses and weekly cycles described herein are also contemplated within the disclosure.

Therapeutically effective amounts of an MMP-9 inhibitor or a composition comprising the same, in some embodiments, vary and depend on the severity of the disease, the subject's weight, and general state of the subject being treated. Administration is, in some embodiments, daily, on alternating days, weekly, twice a month, monthly, or more or less frequently, as necessary depending on the response of the disorder or condition and the subject's tolerance to the therapy. In some embodiments, maintenance dosages over a longer period of time, such as 4, 5, 6, 7, 8, 10, or 12 weeks or longer, are needed until a desired suppression of disorder symptoms occurs, and dosages are adjusted as necessary. The progress of this therapy is easily monitored by conventional techniques and assays.

A physician having ordinary skill in the art, in some cases, readily determines and prescribes the effective amount ($ED_{50}$) of the composition required. For example, the physician could start doses of the active agents employed in the composition at levels lower than that required to achieve the desired therapeutic effect and gradually increase the dosage until the desired effect is achieved. Alternatively, a dose remains constant in some embodiments.

An MMP-9 inhibitor suitable for use with the disclosed methods and compositions comprising the same may be presented in unit dosage forms to facilitate accurate dosing. The term "unit dose" or "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. In some embodiments, the dosage forms described herein can be administered as a unit dose. Typical unit dosage forms include prefilled, premeasured ampules or syringes of the liquid compositions or pills, tablets, capsules or the like in the case of solid compositions.

The dosage of an MMP-9 inhibitor or compositions comprising the same can vary depending on multiple factors, such as, e.g., the pharmacodynamic properties of the compound, the mode of administration, age, health, or weight of the recipient, the nature and extent of the symptoms, frequency of the treatment, the type of concurrent treatment, if any, and the clearance rate of the therapeutic agent in the animal to be treated. One of skill in the art can determine the appropriate dosage based on the above factors. An MMP-9 inhibitor or compositions comprising the same may be administered initially in a suitable dosage that may be adjusted as required, depending on the clinical response. It is noted that dosage values may vary with the type and severity of the condition to be alleviated. It is further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In some embodiments, the antibody is given at an initial loading dose by intravenous administration, then a maintenance dose given weekly via subcutaneous administration. In some embodiments, the initial loading dose and maintenance dose are both administered subcutaneously.

An exemplary, non-limiting range for a therapeutically or prophylactically effective amount of an antibody or antibody portion of the invention is selected from 10-100 mg, more preferably 20-80 mg and even more preferably about 40 mg, about 50 mg, or about 150 mg. As disclosed in U.S. Pat. No. 8,377,443, additional non-limiting ranges include 10 ng/kg to up to 100 mg/kg of mammal body weight or more per day administered to a subject. Preferably, the dosage is selected from 1 µg/kg/day, 100 µg/kg/day, 500 µg/kg/day, 1 mg/kg/day, 10 mg/kg/day or 20 mg/kg/day. It is noted that dosage values may vary with the type and severity of the condition to be alleviated. It is further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In some embodiments, the antibody is given at an initial loading dose by intravenous administration, then a maintenance dose given weekly via subcutaneous administration. In some embodiments, the initial loading dose is 400 mg, 500 mg, 600 mg, 700 mg, 800 mg, 900 mg, or 1000 mg of the antibody administered intravenously. In some embodiments, the maintenance dose is 50 mg, 100 mg, 150 mg, 200 mg, 250 mg, 300 mg, 350 mg, or 400 mg administered subcutaneously on a weekly schedule or every other week schedule.

In some embodiments, the initial loading dose and maintenance dose are both administered subcutaneous. In some embodiments, the initial loading dose is 150 mg, 300 mg, 400 mg, 500 mg, 600 mg, 700 mg, 800 mg, 900 mg, or 1000 mg of the antibody administered subcutaneously. In some embodiments, the maintenance dose is 50 mg, 100 mg, 150 mg, 200 mg, 250 mg, 300 mg, 350 mg, or 400 mg administered subcutaneously on a weekly schedule or every other week schedule.

In some embodiments, the subject is between about 2 and about 5 years of age and the antibody is administered subcutaneously with a dose of between 10 mg and 150 mg. Preferably, the antibody is administered subcutaneously with a dose of 15 mg to 50 mg. In some embodiments, the dose is 10 mg. In some embodiments, the dose is 15 mg. In some embodiments, the dose is 20 mg. In some embodiments, the dose is 25 mg. In some embodiments, the dose is 30 mg. In some embodiments, the dose is 35 mg. In some embodiments, the dose is 40 mg. In some embodiments, the dose is 45 mg. In some embodiments, the dose is 50 mg. In some embodiments, the dose is administered every week or every other week.

In some embodiments, a loading dose, or up to three loading doses, is followed one week later or two weeks later by a maintenance dose of administered every week or every other week, where the loading dose is greater than the maintenance dose. In other embodiments, the loading dose is not administered. In other embodiments, the loading dose is replaced by administration of another therapeutic modality.

In some embodiments, the subject is between about 6 and about 11 years of age and the antibody is administered subcutaneously with a dose of 25 mg to 150 mg. Preferably, the antibody is administered subcutaneously with a dose of 25 mg to 75 mg. In some embodiments, the dose is 25 mg. In some embodiments, the dose is 30 mg. In some embodiments, the dose is 35 mg. In some embodiments, the dose is 40 mg. In some embodiments, the dose is 45 mg. In some embodiments, the dose is 50 mg. In some embodiments, the dose is 55 mg. In some embodiments, the dose is 60 mg. In some embodiments, the dose is 65 mg. In some embodiments, the dose is 70 mg. In some embodiments, the dose is 75 mg. In some embodiments, the dose is administered every week or every other week.

In preferred embodiments, the subject is of age greater than about 12 years and an MMP-9 inhibitor (such as andecaliximab) dose of 150 mg is administered every week. In another preferred embodiment, the subject is of age greater than about 12 years and an MMP-9 inhibitor dose of 50 mg is administered every week. In another preferred embodiment, the subject is aged between about 6 to about 11 years and an MMP-9 inhibitor dose of 75 mg is administered every week. In another preferred embodiment, the subject is aged between about 6 to about 11 years and an MMP-9 inhibitor dose of 25 mg is administered every week. In another preferred embodiment, the subject is aged between 2 and about 5 years and an MMP-9 inhibitor dose of 45 or 50 mg is administered every week. In another preferred embodiment, the subject is aged between 2 and about 5 years and an MMP-9 inhibitor dose of 15 mg is administered every week.

In preferred embodiments, the subject is aged between about 6 and about 11 years and an MMP-9 inhibitor (such as andecaliximab) dose of 75 mg is administered every week. In some embodiments, the subject is aged between about 6 and about 11 years and a dose of 25 mg is administered every week. In some embodiments, the subject is aged between about 2 and about 5 years and a dose of 50 or 45 mg is administered every other week. In some embodiments, the subject is aged 2-5 years and a dose of 15 mg is administered every other week. In some embodiments, the subject is aged 6-11 years and a dose of 75 mg is administered every other week. In some embodiments, the subject is aged 2-5 years and a dose of 45 or 50 mg is administered every other week.

In some embodiments, there are two dosing regimens. In some embodiments, a higher dose gives complete target coverage across the entire age population. In other embodiments, the lower dose gives good coverage and mitigates potential side effects regarding open growth plates in children.

In other embodiments, the dosing is adjusted by age group.

In some embodiments, the antibody is formulated as a depot or sustained release formulation and the dosing interval frequency is reduced by a factor of about two or three or four or greater than four. Sustained release formulations are described in, e.g., U.S. Pat. No. 10,000,562. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. Microencapsulation of recombinant proteins for sustained release has been successfully performed with human growth hormone (rhGH), interferon-(rhIFN-), interleukin-2, and MN rpg 120. Johnson et al., Nat. Med. 2:795-799 (1996); Yasuda et al., Biomed. Ther. 27:1221-1223 (1993); Hora et al., Bio/Technology 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds., (Plenum Press: New York, 1995), pp. 439-462; WO 97/03692; WO 96/40072; WO 96/07399; and U.S. Pat. No. 5,654,010.

Combination Therapy

In some embodiments, a method of treating gHO (e.g., FOP) using an MMP-9 inhibitor as disclosed herein comprises administering a second therapeutic agent or supportive therapy to the subject. In some embodiments, the second therapeutic agent or supportive therapy is selected from the group consisting of isotretinoin, etidronate with oral corticosteroids, perhexiline maleate, Activin-A inhibitor, Activin A Receptor Type 2 (ALK2) inhibitor, allele-specific RNA interference of ALK2, hypoxia inducible factor-1α (Hif-1α) inhibitor, small molecule inhibitor of Bone Morphogenetic Protein (BMP) signaling, anti-BMP9 antibody or antigen-binding fragment thereof, anti-BMP10 antibody or antigen-binding fragment thereof, anti-TGF-B antibody or antigen-binding fragment thereof, an IL1beta inhibitor, an IL6 inhibitor, momelotinib, chromolyn, imatinib, apyrase, rapamycin, a kinase inhibitor, saracatinib, palovarotene, retinoic acid receptor gamma agonists, retinoic acid receptor alpha agonists, bisphosphonates, radiation therapy, anti-inflammatory agents, physical therapy, and combinations thereof.

In some embodiments, a method of treating gHO (e.g., FOP) with an MMP-9 inhibitor includes administering the MMP-9 inhibitor in combination with a second MMP inhibitor. In some embodiments, the second MMP inhibitor is selected from the group consisting of an MMP-2 inhibitor, an MMP-7 inhibitor, an MMP-13 inhibitor, an MMP-14 inhibitor, or an MMP-16 inhibitor.

In some embodiments, the MMP-9 inhibitor or a composition comprising the same is administered combination with a second therapeutic agent or supportive therapy either simultaneously or sequentially, depending upon the condition to be treated and the, the weight and age of the subject, the severity of the disease condition, the manner of administration, and the like, which, in some cases, are readily determined by one of ordinary skill in the art.

In some embodiments, a method of treating gHO (e.g., FOP) with an MMP-9 inhibitor includes administering the MMP-9 inhibitor in combination with an activin receptor type 2A (ACVR2A) antagonist.

In some embodiments, a method of treating gHO (e.g., FOP) with an MMP-9 inhibitor includes administering the MMP-9 inhibitor in combination with an activin receptor type 2B (ACVR2B) antagonist.

In some embodiments, a method of treating gHO (e.g., FOP) with an MMP-9 inhibitor includes administering the MMP-9 inhibitor in combination with an activin receptor type 1 (ACVR1) antagonist.

In some embodiments, a method of treating gHO (e.g., FOP) with an MMP-9 inhibitor includes administering the MMP-9 inhibitor in combination with an anti-activin receptor type 1 (ACVR1) antibody. In some embodiments, a method of treating gHO (e.g., FOP) with an MMP-9 inhibitor includes administering the MMP-9 inhibitor in combination with the anti-activin receptor type 1 (ACVR1) antibody REGN2477.

In some embodiments, a method of treating gHO (e.g., FOP) with an MMP-9 inhibitor includes administering the MMP-9 inhibitor in combination with a hypoxia inducible factor-1α (Hif-1α) inhibitor. Without being bound by theory, treatment with a Hif-1α inhibitor is thought to reduce heterotopic ossification by preventing Hif-1α mediated upregulation of signaling from BMP-2. In the BMP-2 pathway, a ligand activates BMP-2, causing phosphorylation of SMAD 1/5/8, which leads to gene transcription, cell differentiation, and cell proliferation resulting in increased osteogenic factors. Thus, blocking this pathway with a Hif-1α inhibitor could reduce heterotopic ossification. Additionally, Hif-1α leads to increased expression of vascular endothelial growth factor (VEGF), basic fibroblast growth factor (BFGF), platelet-derived growth factor (PDGF), and angiopoietin-2, all of which are needed for endothelial cell motility, recruitment, and proliferation. (Ranganathan, K., Loder, S., Agarwal, S., Wong, V. W., Forsberg, J., David, T. A., Wang, S., James, A. W., and Levi, B., J Bone Joint Surg Am. 2015 Jul. 1; 97 (13): 1101-1111). Hif-1α also contributes to heterotopic ossification by regulating sex-determining region Y-box 9, which is a necessary cartilage precursor. (Ranganathan, K., Loder, S., Agarwal, S., Wong, V. W., Forsberg, J., David, T. A., Wang, S., James, A. W., and Levi, B., J Bone Joint Surg Am. 2015 Jul. 1; 97 (13): 1101-1111). In some embodiments, a method of treating gHO (e.g., FOP) with an MMP-9 inhibitor includes administering the MMP-9 inhibitor in combination with the Hif-1α inhibitor applied locally. In some embodiments, the Hif-1α inhibitor is imatinib, rapamycin, or an inhibitory RNA.

In some embodiments, a method of treating gHO (e.g., FOP) with an MMP-9 inhibitor includes administering the MMP-9 inhibitor in combination with a small molecule inhibitor of bone morphogenetic protein (BMP) signaling.

In some embodiments, a method of treating gHO (e.g., FOP) with an MMP-9 inhibitor includes administering the MMP-9 inhibitor in combination with an antibody against Activin B.

In some embodiments, a method of treating gHO (e.g., FOP) with an MMP-9 inhibitor includes administering the MMP-9 inhibitor in combination with an antibody against BMP9.

In some embodiments, a method of treating gHO (e.g., FOP) with an MMP-9 inhibitor includes administering the MMP-9 inhibitor in combination with an antibody against BMP10.

In some embodiments, a method of treating gHO (e.g., FOP) with an MMP-9 inhibitor includes administering the MMP-9 inhibitor in combination with momelotinib.

In some embodiments, a method of treating gHO (e.g., FOP) with an MMP-9 inhibitor includes administering the MMP-9 inhibitor in combination with palovarotene. Without being bound by theory, the mechanism by which palovarotene is thought to inhibit heterotopic ossification is through the RAR-g receptor expressed on chondrogenic cells and chondrocytes, which is a transcriptional repressor that will inhibit osteogenesis. (Shimono K, Tung W E, Macolino C, Chi A H, Didizian J H, Mundy C, Chandraratna R A, Mishina Y, Enomoto-Iwamoto M, Pacifici M, Iwamoto M. Potent inhibition of heterotopic ossification by nuclear retinoic acid receptor-γ agonists. Nat Med. 2011. April; 17 (4): 454-60. Epub 2011 Apr. 3). Administering palovarotene, a RAR-g receptor agonist, prevents mesenchymal stem cell differentiation into chondrocytes, thereby preventing chondrogenesis and endochondral ossification. (Shimono K, Tung W E, Macolino C, Chi A H, Didizian J H, Mundy C, Chandraratna R A, Mishina Y, Enomoto-Iwamoto M, Pacifici M, Iwamoto M. Potent inhibition of heterotopic ossification by nuclear retinoic acid receptor-γ agonists. Nat Med. 2011. April; 17 (4): 454-60. Epub 2011 Apr. 3). Palovarotene has shown promise in a mouse model of fibrodysplasia ossificans progressiva and is currently in Stage 3 clinical trials. (Shimono K, Tung W E, Macolino C, Chi A H, Didizian J H, Mundy C, Chandraratna R A, Mishina Y, Enomoto-Iwamoto M, Pacifici M, Iwamoto M. Potent inhibition of heterotopic ossification by nuclear retinoic acid receptor-γ agonists. Nat Med. 2011. April; 17 (4): 454-60. Epub 2011 Apr. 3; Ongoing Clinical Trials in FOP, International Fibrodysplasia Ossificans Progressiva Association).

In some embodiments, a method of treating gHO (e.g., FOP) with an MMP-9 inhibitor includes administering the MMP-9 inhibitor in combination with imatinib.

In some embodiments, a method of treating gHO (e.g., FOP) with an MMP-9 inhibitor includes administering the MMP-9 inhibitor in combination with a BMP receptor kinase inhibitor.

In some embodiments, a method of treating gHO (e.g., FOP) with an MMP-9 inhibitor includes administering the MMP-9 inhibitor in combination with sarcatnib.

In some embodiments, a method of treating gHO (e.g., FOP) with an MMP-9 inhibitor includes administering the MMP-9 inhibitor in combination with a TNF inhibitor In some embodiments, a method of treating gHO (e.g., FOP) with an MMP-9 inhibitor includes administering the MMP-9 inhibitor in combination with a BTK inhibitor.

MMP-9 Inhibitors

Disclosed herein, in some embodiments, are MMP-9 inhibitors suitable for use in treating a patient having a genetic heterotopic ossification (gHO), such as fibrodysplasia ossificans progressiva (FOP). In some embodiments, an MMP-9 inhibitor suitable for use with the disclosed methods is an anti-MMP-9 antibody or an antigen-binding fragment thereof (e.g., an inhibitory anti-MMP-9 antibody or an antigen-binding fragment thereof). In some embodiments, an MMP-9 inhibitor suitable for use with the disclosed methods is an inhibitory RNA (e.g., antisense oligonucleotide (ASO), a short interfering RNA (siRNA), a microRNA (miRNA), a short hairpin RNA (shRNA), or an shRNA-adapted microRNA (shmiRNA)). In some embodiments, an MMP-9 inhibitor suitable for use with the disclosed methods is a small molecule inhibitor of MMP-9. In some embodiments, an MMP-9 inhibitor suitable for use with the disclosed methods is an inhibitory polypeptide. In some embodiments, an MMP-9 inhibitor suitable for use with the disclosed methods is a recombinant expression system capable of knocking out the MMP-9 gene from the MMP-9 gene locus in a subject (e.g., CRISPR-Cas system). In some embodiments, an MMP-9 inhibitor suitable for use with the disclosed methods is any combination of the aforementioned therapeutic modalities.

Anti-MMP-9 Antibodies

Disclosed herein, in some embodiments, are anti-MMP-9 antibodies or antigen-binding fragments thereof, such as inhibitory anti-MMP-9 antibodies or antigen-binding fragments thereof. For example, WO/2017/177179 discloses various anti-MMP-9 antibodies. The antibodies show anti-MMP-9 activity; however, there appears to be no known successful therapies including administration of such antibodies used to treat gHO, such as FOP. Accordingly, provided herein are methods for treating gHO by administering an anti-MMP-9 antibody or antigen-binding fragment thereof to inhibit MMP-9. In some embodiments, the anti-MMP-9 antibody or antigen-binding fragment thereof inhibits MMP-9 activation or enzymatic activity.

In some embodiments, the inhibitor of MMP-9 comprises an anti-MPP-9 antibody or antigen-binding fragment thereof, wherein the anti-MPP-9 antibody or antigen-binding fragment thereof binds to (i) an MMP-9 pro-form and inhibits activation of the pro-form and/or (ii) an MMP-9 active form and inhibits activity of the active form and is used as a method for treating gHO (e.g., FOP).

In some embodiments, the anti-MMP-9 antibody or antigen-binding fragment thereof binds to the MMP-9 pro-form to inhibit MMP-9 activation and is used as a method for treating gHO (e.g., FOP).

In some embodiments, the anti-MMP-9 antibody or antigen-binding fragment thereof binds allosterically to the active form of MMP-9 to inhibit MMP-9 activity and is used as a method for gHO (e.g., FOP).

In some embodiments, therapeutic antibodies for administration are characterized as binding to one or more processing sites (e.g., sites of proteolytic cleavage) in MMP-9, thereby effectively blocking processing of the proenzyme or preproenzyme to the catalytically active enzyme, and thus reducing the proteolytic activity of the MMP-9.

In some embodiments, therapeutic antibodies for administration are characterized as binding to MMP-9 with an affinity at least 2 times, at least 5 times, at least 10 times, at least 25 times, at least 50 times, at least 100 times, at least 500 times, or at least 1000 times greater than its binding affinity for another MMP. Binding affinity can be measured by any method known in the art and can be expressed as, for example, on-rate, off-rate, dissociation constant ($K_d$), equilibrium constant ($K_{eq}$) or any term in the art. Various examples of such affinity-matured antibodies are within the scope of the invention.

In some embodiments, therapeutic antibodies for administration are characterized as non-competitive inhibitor of the catalytic activity of MMP-9. In some embodiments, an anti-MMP-9 antibody or antigen-binding fragment thereof suitable for use with the methods of the present disclosure binds within the catalytic domain of MMP-9. In some embodiments, an anti-MMP-9 antibody or antigen-binding fragment thereof suitable for use with the methods of the present disclosure binds outside the catalytic domain of MMP-9.

Additional antibodies or antigen-binding fragments thereof are contemplated within the scope of the invention that compete with anti-MMP-9 antibodies or antigen-binding fragments thereof described herein for binding to MMP-9. For instance, anti-MMP-9 antibodies, and functional fragments thereof, that compete for binding with, for example, an antibody having a heavy chain polypeptide, a light chain polypeptide, or combinations thereof. In some embodiments, a method for treating gHO (e.g., FOP) comprises administration of one or more anti-MMP-9 antibodies or antigen-binding fragments comprising one or more amino acid sequences listed in Table 1.

SDS3 is a targeting antibody that binds to the $Zn^{2+}$ active site and surface epitopes of activated MMP-9, rather than mimicking the endogenous MMP-9 inhibitors, tissue inhibitor of metalloproteinases (TIMPs). In mice, SDS3 bound and inhibited MMP-9 with a $K_D$ of 200 nM and $K_i$ of 1 mM, respectively, providing both prophylactic and therapeutic benefits in a model of dextran sodium sulfate-induced colitis. (Sela-Passwell N, Kikkeri R, Dym O, Rozenberg H, Margalit R, Arad-Yellin R, et al. Antibodies targeting the catalytic zinc complex of activated matrix metalloproteinases show therapeutic potential. Nat Med. (2011)18:143-7. doi: 10.1038/nm.2582). Accordingly, in some embodiments, a method for treating gHO (e.g., FOP) comprises administration of humanized SDS3 antibodies. In various other embodiments, the method provides for the administration of similar antibodies or antigen-binding fragments thereof that bind to the $Zn^{2+}$ active site and surface epitopes of activated MMP-9.

Similar to SDS3, SDS4 is a targeting antibody that binds to the $Zn^{2+}$ active site and surface epitopes of activated MMP-9, rather than mimicking TIMPS. In mice, SDS3 bound and inhibited MMP-9 with a $K_D$ of 20 nM and $K_i$ of 54 nM, respectively. (Sela-Passwell N, Kikkeri R, Dym O, Rozenberg H, Margalit R, Arad-Yellin R, et al. Antibodies targeting the catalytic zinc complex of activated matrix metalloproteinases show therapeutic potential. Nat Med. (2011)18:143-7. doi: 10.1038/nm.2582). Accordingly, in some embodiments, a method of treating gHO (e.g., FOP) comprises administration of humanized SDS4 antibodies. In various other embodiments, the method provides for the administration of similar antibodies or antigen-binding fragments thereof that bind to the $Zn^{2+}$ active site and surface epitopes of activated MMP-9.

Mouse REGA-3G12 binds MMP-9 between Trp116 to Lys214, which is located in the catalytic domain separate from the $Zn^{2+}$ binding site. (Martens E, Leyssen A, Van Aelst I, Fiten P, Piccard H, Hu J, et al. A monoclonal antibody inhibits gelatinase B/MMP-9 by selective binding to part of the catalytic domain and not to the fibronectin or zinc binding domains. Biochim Biophys Acta. (2007)1770: 178-86. doi: 10.1016/j.bbagen.2006.10.012). Mouse REGA-3G12 binds MMP-9 with a $K_D$ of 2.1 nM. (Paemen L, Martens E, Masure S, Opdenakker G. Monoclonal antibodies specific for natural human neutrophil gelatinase B used for affinity purification, quantitation by two-site ELISA and inhibition of enzymatic activity. Eur J Biochem. (1995)234: 759-65. doi: 10.1111/j.1432-1033.1995.759_a.x). In rhesus monkeys, REGA-3G12 prevented the mobilization of hematopoietic progenitor cells in response to interleukin-8. (Hu J, Van den Steen P E, Houde M, Ilenchuk T T, Opdenakker G. Inhibitors of gelatinase B/matrix metalloproteinase-9 activity comparison of a peptidomimetic and polyhistidine with single-chain derivatives of a neutralizing monoclonal antibody. Biochem Pharmacol. (2004)67:1001-9. doi: 10.1016/j.bcp.2003.10.030). Accordingly, in some embodiments, a method of treating gHO (e.g., FOP) comprises administration of humanized REGA-3G12 antibodies or antigen-binding fragments thereofs that bind MMP-9 between Trp116 to Lys214, or that bind in the catalytic domain separate from the $Zn^{2+}$ binding site.

WO/2017/177179 discloses anti-MMP-9 antibodies, such as AB0045 (andecaliximab). Andecaliximab binds the catalytic domain of MMP-9 with additional points of contact shielding the site of physiological activation in the prodomain, where it inhibits pro-MMP-9 activation and noncompetitively inhibits MMP-9 activity. Andecaliximab binds to MMP-9 with a $K_D$ of 2.0-6.6 nM and to pro-MMP-9 with a $K_D$ of 0.008-0.043 nM. Andecaliximab inhibits activation of MMP-9 from human pro-MMP-9 with an $IC_{50}$ of 8.2 pM. Clinical trials with andecaliximab have shown the antibody to be safe and well-tolerated. Accordingly, in some embodiments, a method of treating gHO (e.g., FOP) comprises administration of andecaliximab or antigen-binding fragments thereof to a subject. In a surgical orthotopic xenograft model of colorectal carcinoma, the AB0046 antibody (a murine surrogate of andecaliximab) treatment resulted in reduced tumor growth and metastasis.

In some embodiments, the antibodies used in a method for treating gHO (e.g., FOP) comprise antibodies disclosed in WO/2017/177179, PCT/US2012/027160, PCT/US2016/067036, PCT/US2016/054780, WO/2016/023979A1, WO/2008/102359A1, WO/2002/066057, WO/2006/037513, WO/2009/111508, WO/2011/028883, WO/2012/154654, US/2010/0098659, WO/2010/048455, or WO/2012/048291, all of which are herein incorporated by reference in their entirety.

In some embodiments, antibodies or antigen-binding fragments thereof suitable for use with the methods of the disclosure can be derivatized or linked to another functional molecule. For example, the antibody is functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody with another molecule (such as a streptavidin core region or a polyhistidine tag).

In some embodiments, an antibody or antigen-binding fragment thereof suitable for use with the disclosed methods is used in a variety of settings. For example, an antibody or antigen-binding fragment thereof suitable for use with the disclosed methods is administered as a therapeutic agent. In such embodiments, an antibody or antigen-binding fragment thereof can exert its therapeutic effect by any of a variety of mechanisms. For example, an antibody or antigen-binding fragment thereof suitable for use with the disclosed methods may be an antagonist antibody. In yet another example, an antibody or antigen-binding fragment thereof suitable for use with the disclosed methods may be a blocking antibody. In some embodiments, an antibody or antigen-binding fragment thereof suitable for use with the disclosed methods is a neutralizing antibody.

In certain embodiments, an anti-MMP-9 antibody suitable for use with the disclosed methods comprises a heavy chain comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 35 and a light chain comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 36. In certain embodiments, an anti-MMP-9 antibody suitable for use with the disclosed methods comprises a heavy chain comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 35 and a light chain comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 36. In certain embodiments, an anti-MMP-9 antibody suitable for use with the disclosed methods comprises a heavy chain comprising an amino acid having at least 90% (e.g., at least 90%, 91%, 92%, 93%, 94%, 95%, 96%, 97%, 98%, 99%, or more) sequence identity to the amino acid sequence of SEQ ID NO: 35 and a light chain comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 36. In certain embodiments, an anti-MMP-9 antibody suitable for use with the disclosed methods comprises a heavy chain comprising an amino acid having at least 95% (e.g., at least 95%, 96%, 97%, 98%, 99%, or more) sequence identity to the amino acid sequence of SEQ ID NO: 35 and a light chain comprising an amino acid sequence having at least 95% (e.g., at least 95%, 96%, 97%, 98%, 99%, or more) sequence identity to the amino acid sequence of SEQ ID NO: 36. In certain embodiments, an anti-MMP-9 antibody suitable for use with the disclosed methods comprises a heavy chain comprising an amino acid having at least 99% (e.g., at least 99%, or more) sequence identity to the amino acid sequence of SEQ ID NO: 35 and a light chain comprising an amino acid sequence having at least 99% (e.g., at least 99%, or more) sequence identity to the amino acid sequence of SEQ ID NO: 36. In certain embodiments, an anti-MMP-9 antibody suitable for use with the disclosed methods comprises a heavy chain comprising an amino acid having 100% sequence identity to the amino acid sequence of SEQ ID NO: 35 and a light chain comprising an amino acid sequence having 100% sequence identity to the amino acid sequence of SEQ ID NO: 36.

In certain embodiments, an anti-MMP-9 antibody suitable for use with the disclosed methods comprises a heavy chain variable region (VH) comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a light chain variable region (VL) comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 7. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 7. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 55 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 7. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 55 and a VL comprising an amino acid sequence having at least 95% (e.g., at least 95%, 96%, 97%, 98%, 99%, or more) sequence identity to the amino acid sequence of SEQ ID NO: 7. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 55 and a VL comprising an amino acid sequence having at least 99% (e.g., at least 99%, or more) sequence identity to the amino acid sequence of SEQ ID NO: 7. In certain embodiments, an anti-MMP-9 antibody suitable for use with the disclosed methods comprises a VH comprising an amino acid having 100% sequence identity to the amino acid sequence of SEQ ID NO: 55 and a VL comprising an amino acid sequence having 100% sequence identity to the amino acid sequence of SEQ ID NO: 7.

In certain embodiments, an anti-MMP-9 antibody suitable for use with the disclosed methods comprises a heavy chain variable region comprising a heavy chain complementarity determining region 1 (HCDR1) comprising the amino acid sequence of SEQ ID NO: 8, an HCDR2 comprising the amino acid sequence of SEQ ID NO: 9, and an HCDR3 comprising the amino acid sequence of SEQ ID NO: 10, and a light chain variable region comprising a light chain complementarity determining region 1 (LCDR1) comprising the amino acid sequence of SEQ ID NO: 11, an LCDR2 comprising the amino acid sequence of SEQ ID NO: 12, and an LCDR3 comprising the amino acid sequence of SEQ ID NO: 13.

In certain embodiments, an anti-MMP-9 antibody suitable for use with the disclosed methods comprises a heavy chain comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 1 and a light chain comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 2. In certain embodiments, an anti-MMP-9 antibody suitable for use with the disclosed methods comprises a heavy chain comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 1 and a light chain comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 2. In certain embodiments, an anti-MMP-9 antibody suitable for use with the disclosed methods comprises a heavy chain comprising an amino acid having at least 90% (e.g., at least 90%, 91%, 92%, 93%, 94%, 95%, 96%, 97%, 98%, 99%, or more) sequence identity to the amino acid sequence of SEQ ID NO: 1 and a light chain comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 2. In certain embodiments, an anti-MMP-9 antibody suitable for use with the disclosed methods comprises a heavy chain comprising an amino acid having at least 95% (e.g., at least 95%, 96%, 97%, 98%, 99%, or more) sequence identity to the amino acid sequence of SEQ ID NO: 1 and a light chain comprising an amino acid sequence having at least 95% (e.g., at least 95%, 96%, 97%, 98%, 99%, or more) sequence identity to the amino acid sequence of SEQ ID NO: 2. In certain embodiments, an anti-MMP-9 antibody suitable for use with the disclosed methods comprises a heavy chain comprising an amino acid having at least 99% (e.g., at least 99%, or more) sequence identity to the amino acid sequence of SEQ ID NO: 1 and a light chain comprising an amino acid sequence having at least 99% (e.g., at least 99%, or more) sequence identity to the amino acid sequence of SEQ ID NO: 2. In certain embodiments, an anti-MMP-9 antibody suitable for use with the disclosed methods comprises a heavy chain comprising an amino acid having 100% sequence identity to the amino acid sequence of SEQ ID NO: 1 and a light chain comprising an amino acid sequence having 100% sequence identity to the amino acid sequence of SEQ ID NO: 2.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 3 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 3 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 3 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 3 and a VL comprising an amino acid sequence having at least 95% (e.g., at least 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 3 and a VL comprising an amino acid sequence having at least 99% (e.g., at least 99%, or more) sequence identity to the amino acid sequence of SEQ ID NO: 47. In certain embodiments, an anti-MMP-9 antibody suitable for use with the disclosed methods comprises a VH comprising an amino acid having 100% sequence identity to the amino acid sequence of SEQ ID NO: 3 and a VL comprising an amino acid sequence having 100% sequence identity to the amino acid sequence of SEQ ID NO: 47.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 3 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 3 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 3 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 3 and a VL comprising an amino acid sequence having at least 95% (e.g., at least 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 3 and a VL comprising an amino acid sequence having at least 99% (e.g., at least 99%, or more) sequence identity to the amino acid sequence of SEQ ID NO: 57. In certain embodiments, an anti-MMP-9 antibody suitable for use with the disclosed methods comprises a VH comprising an amino acid having 100% sequence identity to the amino acid sequence of SEQ ID NO: 3 and a VL comprising an amino acid sequence having 100% sequence identity to the amino acid sequence of SEQ ID NO: 57.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 3 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 3 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 3 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 3 and a VL comprising an amino acid sequence having at least 95% (e.g., at least 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 3 and a VL comprising an amino acid sequence having at least 99% (e.g., at least 99%, or more) sequence identity to the amino acid sequence of SEQ ID NO: 58. In certain embodiments, an anti-MMP-9 antibody suitable for use with the disclosed methods comprises a VH comprising an amino acid having 100% sequence identity to the amino acid sequence of SEQ ID NO: 3 and a VL comprising an amino acid sequence having 100% sequence identity to the amino acid sequence of SEQ ID NO: 58.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 3 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 3 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 3 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 3 and a VL comprising an amino acid sequence having at least 95% (e.g., at least 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 3 and a VL comprising an amino acid sequence having at least 99% (e.g., at least 99%, or more) sequence identity to the amino acid sequence of SEQ ID NO: 59. In certain embodiments, an anti-MMP-9 antibody suitable for use with the disclosed methods comprises a VH comprising an amino acid having 100% sequence identity to the amino acid sequence of SEQ ID NO: 3 and a VL comprising an amino acid sequence having 100% sequence identity to the amino acid sequence of SEQ ID NO: 59.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 3 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 3 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 3 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 3 and a VL comprising an amino acid sequence having at least 95% (e.g., at least 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 3 and a VL comprising an amino acid sequence having at least 99% (e.g., at least 99%, or more) sequence identity to the amino acid sequence of SEQ ID NO: 60. In certain embodiments, an anti-MMP-9 antibody suitable for use with the disclosed methods comprises a VH comprising an amino acid having 100% sequence identity to the amino acid sequence of SEQ ID NO: 3 and a VL comprising an amino acid sequence having 100% sequence identity to the amino acid sequence of SEQ ID NO: 60.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 3 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 3 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 3 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 3 and a VL comprising an amino acid sequence having at least 95% (e.g., at least 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 3 and a VL comprising an amino acid sequence having at least 99% (e.g., at least 99%, or more) sequence identity to the amino acid sequence of SEQ ID NO: 6. In certain embodiments, an anti-MMP-9 antibody suitable for use with the disclosed methods comprises a VH comprising an amino acid having 100% sequence identity to the amino acid sequence of SEQ ID NO: 3 and a VL comprising an amino acid sequence having 100% sequence identity to the amino acid sequence of SEQ ID NO: 6.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 46 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 46 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 46 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 46 and a VL comprising an amino acid sequence having at least 95% (e.g., at least 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 46 and a VL comprising an amino acid sequence having at least 99% (e.g., at least 99%, or more) sequence identity to the amino acid sequence of SEQ ID NO: 47. In certain embodiments, an anti-MMP-9 antibody suitable for use with the disclosed methods comprises a VH comprising an amino acid having 100% sequence identity to the amino acid sequence of SEQ ID NO: 46 and a VL comprising an amino acid sequence having 100% sequence identity to the amino acid sequence of SEQ ID NO: 47.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 46 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 46 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 46 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 46 and a VL comprising an amino acid sequence having at least 95% (e.g., at least 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 46 and a VL comprising an amino acid sequence having at least 99% (e.g., at least 99%, or more) sequence identity to the amino acid sequence of SEQ ID NO: 57. In certain embodiments, an anti-MMP-9 antibody suitable for use with the disclosed methods comprises a VH comprising an amino acid having 100% sequence identity to the amino acid sequence of SEQ ID NO: 46 and a VL comprising an amino acid sequence having 100% sequence identity to the amino acid sequence of SEQ ID NO: 57.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 46 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 46 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 46 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 46 and a VL comprising an amino acid sequence having at least 95% (e.g., at least 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 46 and a VL comprising an amino acid sequence having at least 99% (e.g., at least 99%, or more) sequence identity to the amino acid sequence of SEQ ID NO: 58. In certain embodiments, an anti-MMP-9 antibody suitable for use with the disclosed methods comprises a VH comprising an amino acid having 100% sequence identity to the amino acid sequence of SEQ ID NO: 46 and a VL comprising an amino acid sequence having 100% sequence identity to the amino acid sequence of SEQ ID NO: 58.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 46 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 46 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 46 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 46 and a VL comprising an amino acid sequence having at least 95% (e.g., at least 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 46 and a VL comprising an amino acid sequence having at least 99% (e.g., at least 99%, or more) sequence identity to the amino acid sequence of SEQ ID NO: 59. In certain embodiments, an anti-MMP-9 antibody suitable for use with the disclosed methods comprises a VH comprising an amino acid having 100% sequence identity to the amino acid sequence of SEQ ID NO: 46 and a VL comprising an amino acid sequence having 100% sequence identity to the amino acid sequence of SEQ ID NO: 59.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 46 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 46 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 46 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 46 and a VL comprising an amino acid sequence having at least 95% (e.g., at least 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 46 and a VL comprising an amino acid sequence having at least 99% (e.g., at least 99%, or more) sequence identity to the amino acid sequence of SEQ ID NO: 60. In certain embodiments, an anti-MMP-9 antibody suitable for use with the disclosed methods comprises a VH comprising an amino acid having 100% sequence identity to the amino acid sequence of SEQ ID NO: 46 and a VL comprising an amino acid sequence having 100% sequence identity to the amino acid sequence of SEQ ID NO: 60.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 46 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 46 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 46 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 46 and a VL comprising an amino acid sequence having at least 95% (e.g., at least 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 46 and a VL comprising an amino acid sequence having at least 99% (e.g., at least 99%, or more) sequence identity to the amino acid sequence of SEQ ID NO: 6. In certain embodiments, an anti-MMP-9 antibody suitable for use with the disclosed methods comprises a VH comprising an amino acid having 100% sequence identity to the amino acid sequence of SEQ ID NO: 46 and a VL comprising an amino acid sequence having 100% sequence identity to the amino acid sequence of SEQ ID NO: 6.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 48 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 48 and a VL comprising an amino acid sequence having at least 95% (e.g., at least 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 48 and a VL comprising an amino acid sequence having at least 99% (e.g., at least 99%, or more) sequence identity to the amino acid sequence of SEQ ID NO: 47. In certain embodiments, an anti-MMP-9 antibody suitable for use with the disclosed methods comprises a VH comprising an amino acid having 100% sequence identity to the amino acid sequence of SEQ ID NO: 48 and a VL comprising an amino acid sequence having 100% sequence identity to the amino acid sequence of SEQ ID NO: 47.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 48 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 48 and a VL comprising an amino acid sequence having at least 95% (e.g., at least 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 48 and a VL comprising an amino acid sequence having at least 99% (e.g., at least 99%, or more) sequence identity to the amino acid sequence of SEQ ID NO: 57. In certain embodiments, an anti-MMP-9 antibody suitable for use with the disclosed methods comprises a VH comprising an amino acid having 100% sequence identity to the amino acid sequence of SEQ ID NO: 48 and a VL comprising an amino acid sequence having 100% sequence identity to the amino acid sequence of SEQ ID NO: 57.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 48 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 48 and a VL comprising an amino acid sequence having at least 95% (e.g., at least 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 48 and a VL comprising an amino acid sequence having at least 99% (e.g., at least 99%, or more) sequence identity to the amino acid sequence of SEQ ID NO: 58. In certain embodiments, an anti-MMP-9 antibody suitable for use with the disclosed methods comprises a VH comprising an amino acid having 100% sequence identity to the amino acid sequence of SEQ ID NO: 48 and a VL comprising an amino acid sequence having 100% sequence identity to the amino acid sequence of SEQ ID NO: 58.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 48 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 48 and a VL comprising an amino acid sequence having at least 95% (e.g., at least 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 48 and a VL comprising an amino acid sequence having at least 99% (e.g., at least 99%, or more) sequence identity to the amino acid sequence of SEQ ID NO: 59. In certain embodiments, an anti-MMP-9 antibody suitable for use with the disclosed methods comprises a VH comprising an amino acid having 100% sequence identity to the amino acid sequence of SEQ ID NO: 48 and a VL comprising an amino acid sequence having 100% sequence identity to the amino acid sequence of SEQ ID NO: 59.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 48 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 48 and a VL comprising an amino acid sequence having at least 95% (e.g., at least 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 48 and a VL comprising an amino acid sequence having at least 99% (e.g., at least 99%, or more) sequence identity to the amino acid sequence of SEQ ID NO: 60. In certain embodiments, an anti-MMP-9 antibody suitable for use with the disclosed methods comprises a VH comprising an amino acid having 100% sequence identity to the amino acid sequence of SEQ ID NO: 48 and a VL comprising an amino acid sequence having 100% sequence identity to the amino acid sequence of SEQ ID NO: 60.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more)

sequence identity to the amino acid sequence of SEQ ID NO: 48 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 48 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 48 and a VL comprising an amino acid sequence having at least 95% (e.g., at least 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 48 and a VL comprising an amino acid sequence having at least 99% (e.g., at least 99%, or more) sequence identity to the amino acid sequence of SEQ ID NO: 6. In certain embodiments, an anti-MMP-9 antibody suitable for use with the disclosed methods comprises a VH comprising an amino acid having 100% sequence identity to the amino acid sequence of SEQ ID NO: 48 and a VL comprising an amino acid sequence having 100% sequence identity to the amino acid sequence of SEQ ID NO: 6.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 48 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 48 and a VL comprising an amino acid sequence having at least 95% (e.g., at least 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 48 and a VL comprising an amino acid sequence having at least 99% (e.g., at least 99%, or more) sequence identity to the amino acid sequence of SEQ ID NO: 47. In certain embodiments, an anti-MMP-9 antibody suitable for use with the disclosed methods comprises a VH comprising an amino acid having 100% sequence identity to the amino acid sequence of SEQ ID NO: 48 and a VL comprising an amino acid sequence having 100% sequence identity to the amino acid sequence of SEQ ID NO: 47.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 48 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 48 and a VL comprising an amino acid sequence having at least 95% (e.g., at least 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 48 and a VL comprising an amino acid sequence having at least 99% (e.g., at least 99%, or more) sequence identity to the amino acid sequence of SEQ ID NO: 57. In certain embodiments, an anti-MMP-9 antibody suitable for use with the disclosed methods comprises a VH comprising an amino acid having 100% sequence identity to the amino acid sequence of SEQ ID NO: 48 and a VL comprising an amino acid sequence having 100% sequence identity to the amino acid sequence of SEQ ID NO: 57.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 48 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 48 and a VL comprising an amino acid sequence having at least 95% (e.g., at least 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 48 and a VL comprising an amino acid sequence having at least 99% (e.g., at least 99%, or more) sequence identity to the amino acid sequence of SEQ ID NO: 58. In certain embodiments, an anti-MMP-9 antibody suitable for use with the disclosed methods comprises a VH comprising an amino acid having 100% sequence identity to the amino acid sequence of SEQ ID NO: 48 and a VL comprising an amino acid sequence having 100% sequence identity to the amino acid sequence of SEQ ID NO: 58.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 48 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 48 and a VL comprising an amino acid sequence having at least 95% (e.g., at least 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 48 and a VL comprising an amino acid sequence having at least 99% (e.g., at least 99%, or more) sequence identity to the amino acid sequence of SEQ ID NO: 59. In certain embodiments, an anti-MMP-9 antibody suitable for use with the disclosed methods comprises a VH comprising an amino acid having 100% sequence identity to the amino acid sequence of SEQ ID NO: 48 and a VL comprising an amino acid sequence having 100% sequence identity to the amino acid sequence of SEQ ID NO: 59.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 48 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 48 and a VL comprising an amino acid sequence having at least 95% (e.g., at least 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 48 and a VL comprising an amino acid sequence having at least 99% (e.g., at least 99%, or more) sequence identity to the amino acid sequence of SEQ ID NO: 60. In certain embodiments, an anti-MMP-9 antibody suitable for use with the disclosed methods comprises a VH comprising an amino acid having 100% sequence identity to the amino acid sequence of SEQ ID NO: 48 and a VL comprising an amino acid sequence having 100% sequence identity to the amino acid sequence of SEQ ID NO: 60.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 48 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 48 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 48 and a VL comprising an amino acid sequence having at least 95% (e.g., at least 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 48 and a VL comprising an amino acid sequence having at least 99% (e.g., at least 99%, or more) sequence identity to the amino acid sequence of SEQ ID NO: 6. In certain embodiments, an anti-MMP-9 antibody suitable for use with the disclosed methods comprises a VH comprising an amino acid having 100% sequence identity to the amino acid sequence of SEQ ID NO: 48 and a VL comprising an amino acid sequence having 100% sequence identity to the amino acid sequence of SEQ ID NO: 6.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 54 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 54 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 54 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 54 and a VL comprising an amino acid sequence having at least 95% (e.g., at least 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 54 and a VL comprising an amino acid sequence having at least 99% (e.g., at least 99%, or more) sequence identity to the amino acid sequence of SEQ ID NO: 47. In certain embodiments, an anti-MMP-9 antibody suitable for use with the disclosed methods comprises a VH comprising an amino acid having 100% sequence identity to the amino acid sequence of SEQ ID NO: 54 and a VL comprising an amino acid sequence having 100% sequence identity to the amino acid sequence of SEQ ID NO: 47.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 54 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 54 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 54 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 54 and a VL comprising an amino acid sequence having at least 95% (e.g., at least 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 54 and a VL comprising an amino acid sequence having at least 99% (e.g., at least 99%, or more) sequence identity to the amino acid sequence of SEQ ID NO: 57. In certain embodiments, an anti-MMP-9 antibody suitable for use with the disclosed methods comprises a VH comprising an amino acid having 100% sequence identity to the amino acid sequence of SEQ ID NO: 54 and a VL comprising an amino acid sequence having 100% sequence identity to the amino acid sequence of SEQ ID NO: 57.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 54 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 54 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 54 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 54 and a VL comprising an amino acid sequence having at least 95% (e.g., at least 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 54 and a VL comprising an amino acid sequence having at least 99% (e.g., at least 99%, or more) sequence identity to the amino acid sequence of SEQ ID NO: 58. In certain embodiments, an anti-MMP-9 antibody suitable for use with the disclosed methods comprises a VH comprising an amino acid having 100% sequence identity to the amino acid sequence of SEQ ID NO: 54 and a VL comprising an amino acid sequence having 100% sequence identity to the amino acid sequence of SEQ ID NO: 58.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 54 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 54 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 54 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 54 and a VL comprising an amino acid sequence having at least 95% (e.g., at least 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 54 and a VL comprising an amino acid sequence having at least 99% (e.g., at least 99%, or more) sequence identity to the amino acid sequence of SEQ ID NO: 59. In certain embodiments, an anti-MMP-9 antibody suitable for use with the disclosed methods comprises a VH comprising an amino acid having 100% sequence identity to the amino acid sequence of SEQ ID NO: 54 and a VL comprising ID NO: 59.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 54 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 54 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 54 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 54 and a VL comprising an amino acid sequence having at least 95% (e.g., at least 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 54 and a VL comprising an amino acid sequence having at least 99% (e.g., at least 99%, or more) sequence identity to the amino acid sequence of SEQ ID NO: 60. In certain embodiments, an anti-MMP-9 antibody suitable for use with the disclosed methods comprises a VH comprising an amino acid having 100% sequence identity to the amino acid sequence of SEQ ID NO: 54 and a VL comprising ID NO: 60.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 54 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 54 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 54 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 54 and a VL comprising an amino acid sequence having at least 95% (e.g., at least 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 54 and a VL comprising an amino acid sequence having at least 99% (e.g., at least 99%, or more) sequence identity to the amino acid sequence of SEQ ID NO: 6. In certain embodiments, an anti-MMP-9 antibody suitable for use with the disclosed methods comprises a VH comprising an amino acid having 100% sequence identity to the amino acid sequence of SEQ ID NO: 54 and a VL comprising ID NO: 6.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 55 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 55 and a VL comprising an amino acid sequence having at least 95% (e.g., at least 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 55 and a VL comprising an amino acid sequence having at least 99% (e.g., at least 99%, or more) sequence identity to the amino acid sequence of SEQ ID NO: 47. In certain embodiments, an anti-MMP-9 antibody suitable for use with the disclosed methods comprises a VH comprising an amino acid having 100% sequence identity to the amino acid sequence of SEQ ID NO: 55 and a VL comprising ID NO: 47.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 55 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 55 and a VL comprising an amino acid sequence having at least 95% (e.g., at least 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 55 and a VL comprising an amino acid sequence having at least 99% (e.g., at least 99%, or more) sequence identity to the amino acid sequence of SEQ ID NO: 57. In certain embodiments, an anti-MMP-9 antibody suitable for use with the disclosed methods comprises a VH comprising an amino acid having 100% sequence identity to the amino acid sequence of SEQ ID NO: 55 and a VL comprising ID NO: 57.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 55 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 55 and a VL comprising an amino acid sequence having at least 95% (e.g., at least 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 55 and a VL comprising an amino acid sequence having at least 99% (e.g., at least 99%, or more) sequence identity to the amino acid sequence of SEQ ID NO: 58. In certain embodiments, an anti-MMP-9 antibody suitable for use with the disclosed methods comprises a VH comprising an amino acid having 100% sequence identity to the amino acid sequence of SEQ ID NO: 55 and a VL comprising ID NO: 58.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 55 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 55 and a VL comprising an amino acid sequence having at least 95% (e.g., at least 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 55 and a VL comprising an amino acid sequence having at least 99% (e.g., at least 99%, or more) sequence identity to the amino acid sequence of SEQ ID NO: 59. In certain embodiments, an anti-MMP-9 antibody suitable for use with the disclosed methods comprises a VH comprising an amino acid having 100% sequence identity to the amino acid sequence of SEQ ID NO: 55 and a VL comprising ID NO: 59.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 55 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 55 and a VL comprising an amino acid sequence having at least 95% (e.g., at least 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 55 and a VL comprising an amino acid sequence having at least 99% (e.g., at least 99%, or more) sequence identity to the amino acid sequence of SEQ ID NO: 60. In certain embodiments, an anti-MMP-9 antibody suitable for use with the disclosed methods comprises a VH comprising an amino acid having 100% sequence identity to the amino acid sequence of SEQ ID NO: 55 and a VL comprising ID NO: 60.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 55 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 55 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 55 and a VL comprising an amino acid sequence having at least 95% (e.g., at least 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 55 and a VL comprising an amino acid sequence having at least 99% (e.g., at least 99%, or more) sequence identity to the amino acid sequence of SEQ ID NO: 6. In certain embodiments, an anti-MMP-9 antibody suitable for use with the disclosed methods comprises a VH comprising an amino acid having 100% sequence identity to the amino acid sequence of SEQ ID NO: 55 and a VL comprising ID NO: 6.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 56 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 56 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 56 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 56 and a VL comprising an amino acid sequence having at least 95% (e.g., at least 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 56 and a VL comprising an amino acid sequence having at least 99% (e.g., at least 99%, or more) sequence identity to the amino acid sequence of SEQ ID NO: 47. In certain embodiments, an anti-MMP-9 antibody suitable for use with the disclosed methods comprises a VH comprising an amino acid having 100% sequence identity to the amino acid sequence of SEQ ID NO: 56 and a VL comprising ID NO: 47.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 56 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 56 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 56 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 56 and a VL comprising an amino acid sequence having at least 95% (e.g., at least 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 56 and a VL comprising an amino acid sequence having at least 99% (e.g., at least 99%, or more) sequence identity to the amino acid sequence of SEQ ID NO: 57. In certain embodiments, an anti-MMP-9 antibody suitable for use with the disclosed methods comprises a VH comprising an amino acid having 100% sequence identity to the amino acid sequence of SEQ ID NO: 56 and a VL comprising ID NO: 57.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 56 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 56 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 56 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 56 and a VL comprising an amino acid sequence having at least 95% (e.g., at least 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 56 and a VL comprising an amino acid sequence having at least 99% (e.g., at least 99%, or more) sequence identity to the amino acid sequence of SEQ ID NO: 58. In certain embodiments, an anti-MMP-9 antibody suitable for use with the disclosed methods comprises a VH comprising an amino acid having 100% sequence identity to the amino acid sequence of SEQ ID NO: 56 and a VL comprising ID NO: 58.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 56 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 56 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 56 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 56 and a VL comprising an amino acid sequence having at least 95% (e.g., at least 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 56 and a VL comprising an amino acid sequence having at least 99% (e.g., at least 99%, or more) sequence identity to the amino acid sequence of SEQ ID NO: 59. In certain embodiments, an anti-MMP-9 antibody suitable for use with the disclosed methods comprises a VH comprising an amino acid having 100% sequence identity to the amino acid sequence of SEQ ID NO: 56 and a VL comprising ID NO: 59.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 56 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 56 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 56 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 56 and a VL comprising an amino acid sequence having at least 95% (e.g., at least 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 56 and a VL comprising an amino acid sequence having at least 99% (e.g., at least 99%, or more) sequence identity to the amino acid sequence of SEQ ID NO: 60. In certain embodiments, an anti-MMP-9 antibody suitable for use with the disclosed methods comprises a VH comprising an amino acid having 100% sequence identity to the amino acid sequence of SEQ ID NO: 56 and a VL comprising ID NO: 60.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 56 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 56 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 56 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 56 and a VL comprising an amino acid sequence having at least 95% (e.g., at least 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 56 and a VL comprising an amino acid sequence having at least 99% (e.g., at least 99%, or more) sequence identity to the amino acid sequence of SEQ ID NO: 6. In certain embodiments, an anti-MMP-9 antibody suitable for use with the disclosed methods comprises a VH comprising an amino acid having 100% sequence identity to the amino acid sequence of SEQ ID NO: 56 and a VL comprising ID NO: 6.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 4 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 4 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 4 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 4 and a VL comprising an amino acid sequence having at least 95% (e.g., at least 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 4 and a VL comprising an amino acid sequence having at least 99% (e.g., at least 99%, or more) sequence identity to the amino acid sequence of SEQ ID NO: 47. In certain embodiments, an anti-MMP-9 antibody suitable for use with the disclosed methods comprises a VH comprising an amino acid having 100% sequence identity to the amino acid sequence of SEQ ID NO: 4 and a VL comprising ID NO: 47.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 4 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 4 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 4 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 4 and a VL comprising an amino acid sequence having at least 95% (e.g., at least 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 4 and a VL comprising an amino acid sequence having at least 99% (e.g., at least 99%, or more) sequence identity to the amino acid sequence of SEQ ID NO: 57. In certain embodiments, an anti-MMP-9 antibody suitable for use with the disclosed methods comprises a VH comprising an amino acid having 100% sequence identity to the amino acid sequence of SEQ ID NO: 4 and a VL comprising ID NO: 57.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 4 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 4 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 4 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 4 and a VL comprising an amino acid sequence having at least 95% (e.g., at least 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 4 and a VL comprising an amino acid sequence having at least 99% (e.g., at least 99%, or more) sequence identity to the amino acid sequence of SEQ ID NO: 58. In certain embodiments, an anti-MMP-9 antibody suitable for use with the disclosed methods comprises a VH comprising an amino acid having 100% sequence identity to the amino acid sequence of SEQ ID NO: 4 and a VL comprising ID NO: 58.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 4 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 4 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 4 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 4 and a VL comprising an amino acid sequence having at least 95% (e.g., at least 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 4 and a VL comprising an amino acid sequence having at least 99% (e.g., at least 99%, or more) sequence identity to the amino acid sequence of SEQ ID NO: 59. In certain embodiments, an anti-MMP-9 antibody suitable for use with the disclosed methods comprises a VH comprising an amino acid having 100% sequence identity to the amino acid sequence of SEQ ID NO: 4 and a VL comprising ID NO: 59.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 4 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 4 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 4 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 4 and a VL comprising an amino acid sequence having at least 95% (e.g., at least 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 4 and a VL comprising an amino acid sequence having at least 99% (e.g., at least 99%, or more) sequence identity to the amino acid sequence of SEQ ID NO: 60. In certain embodiments, an anti-MMP-9 antibody suitable for use with the disclosed methods comprises a VH comprising an amino acid having 100% sequence identity to the amino acid sequence of SEQ ID NO: 4 and a VL comprising ID NO: 60.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 4 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 4 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 4 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 4 and a VL comprising an amino acid sequence having at least 95% (e.g., at least 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 4 and a VL comprising an amino acid sequence having at least 99% (e.g., at least 99%, or more) sequence identity to the amino acid sequence of SEQ ID NO: 6. In certain embodiments, an anti-MMP-9 antibody suitable for use with the disclosed methods comprises a VH comprising an amino acid having 100% sequence identity to the amino acid sequence of SEQ ID NO: 4 and a VL comprising ID NO: 6.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 5 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 5 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 5 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 5 and a VL comprising an amino acid sequence having at least 95% (e.g., at least 95%, 96%, 97%, 98%, 99%, or more) sequence identity to the amino acid sequence of SEQ ID NO: 47. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 5 and a VL comprising an amino acid sequence having at least 99% (e.g., at least 99%, or more) sequence identity to the amino acid sequence of SEQ ID NO: 47. In certain embodiments, an anti-MMP-9 antibody suitable for use with the disclosed methods comprises a VH comprising an amino acid having 100% sequence identity to the amino acid sequence of SEQ ID NO: 5 and a VL comprising ID NO: 47.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 5 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 5 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 5 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 5 and a VL comprising an amino acid sequence having at least 95% (e.g., at least 95%, 96%, 97%, 98%, 99%, or more) sequence identity to the amino acid sequence of SEQ ID NO: 57. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 5 and a VL comprising an amino acid sequence having at least 99% (e.g., at least 99%, or more) sequence identity to the amino acid sequence of SEQ ID NO: 57. In certain embodiments, an anti-MMP-9 antibody suitable for use with the disclosed methods comprises a VH comprising an amino acid having 100% sequence identity to the amino acid sequence of SEQ ID NO: 5 and a VL comprising ID NO: 57.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 5 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 5 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 5 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 5 and a VL comprising an amino acid sequence having at least 95% (e.g., at least 95%, 96%, 97%, 98%, 99%, or more) sequence identity to the amino acid sequence of SEQ ID NO: 58. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 5 and a VL comprising an amino acid sequence having at least 99% (e.g., at least 99%, or more) sequence identity to the amino acid sequence of SEQ ID NO: 58. In certain embodiments, an anti-MMP-9 antibody suitable for use with the disclosed methods comprises a VH comprising an amino acid having 100% sequence identity to the amino acid sequence of SEQ ID NO: 5 and a VL comprising ID NO: 58.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 5 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 5 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 5 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 5 and a VL comprising an amino acid sequence having at least 95% (e.g., at least 95%, 96%, 97%, 98%, 99%, or more) sequence identity to the amino acid sequence of SEQ ID NO: 59. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 5 and a VL comprising an amino acid sequence having at least 99% (e.g., at least 99%, or more) sequence identity to the amino acid sequence of SEQ ID NO: 59. In certain embodiments, an anti-MMP-9 antibody suitable for use with the disclosed methods comprises a VH comprising an amino acid having 100% sequence identity to the amino acid sequence of SEQ ID NO: 5 and a VL comprising ID NO: 59.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 5 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 5 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 5 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 5 and a VL comprising an amino acid sequence having at least 95% (e.g., at least 95%, 96%, 97%, 98%, 99%, or more) sequence identity to the amino acid sequence of SEQ ID NO: 60. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 5 and a VL comprising an amino acid sequence having at least 99% (e.g., at least 99%, or more) sequence identity to the amino acid sequence of SEQ ID NO: 60. In certain embodiments, an anti-MMP-9 antibody suitable for use with the disclosed methods comprises a VH comprising an amino acid having 100% sequence identity to the amino acid sequence of SEQ ID NO: 5 and a VL comprising ID NO: 60.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 5 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 5 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 5 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 5 and a VL comprising an amino acid sequence having at least 95% (e.g., at least 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 5 and a VL comprising an amino acid sequence having at least 99% (e.g., at least 99%, or more) sequence identity to the amino acid sequence of SEQ ID NO: 6. In certain embodiments, an anti-MMP-9 antibody suitable for use with the disclosed methods comprises a VH comprising an amino acid having 100% sequence identity to the amino acid sequence of SEQ ID NO: 5 and a VL comprising ID NO: 6.

In certain embodiments, an anti-MMP-9 antibody suitable for use with the disclosed methods comprises a heavy chain comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 17 and a light chain comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 18. In certain embodiments, an anti-MMP-9 antibody suitable for use with the disclosed methods comprises a heavy chain comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 17 and a light chain comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 18. In certain embodiments, an anti-MMP-9 antibody suitable for use with the disclosed methods comprises a heavy chain comprising an amino acid having at least 90% (e.g., at least 90%, 91%, 92%, 93%, 94%, 95%, 96%, 97%, 98%, 99%, or more) sequence identity to the amino acid sequence of SEQ ID NO: 17 and a light chain comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 18. In certain embodiments, an anti-MMP-9 antibody suitable for use with the disclosed methods comprises a heavy chain comprising an amino acid having at least 95% (e.g., at least 95%, 96%, 97%, 98%, 99%, or more) sequence identity to the amino acid sequence of SEQ ID NO: 17 and a light chain comprising an amino acid sequence having at least 95% (e.g., at least 95%, 96%, 97%, 98%, 99%, or more) sequence identity to the amino acid sequence of SEQ ID NO: 18. In certain embodiments, an anti-MMP-9 antibody suitable for use with the disclosed methods comprises a heavy chain comprising an amino acid having at least 99% (e.g., at least 99%, or more) sequence identity to the amino acid sequence of SEQ ID NO: 17 and a light chain comprising an amino acid sequence having at least 99% (e.g., at least 99%, or more) sequence identity to the amino acid sequence of SEQ ID NO: 18. In certain embodiments, an anti-MMP-9 antibody suitable for use with the disclosed methods comprises a heavy chain comprising an amino acid having 100% sequence identity to the amino acid sequence of SEQ ID NO: 17 and a light chain comprising an amino acid sequence having 100% sequence identity to the amino acid sequence of SEQ ID NO: 18.

In certain embodiments, an anti-MMP-9 antibody suitable for use with the disclosed methods comprises a heavy chain comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 39 and a light chain comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 18. In certain embodiments, an anti-MMP-9 antibody suitable for use with the disclosed methods comprises a heavy chain comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 39 and a light chain comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 18. In certain embodiments, an anti-MMP-9 antibody suitable for use with the disclosed methods comprises a heavy chain comprising an amino acid having at least 90% (e.g., at least 90%, 91%, 92%, 93%, 94%, 95%, 96%, 97%, 98%, 99%, or more) sequence identity to the amino acid sequence of SEQ ID NO: 39 and a light chain comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 18. In certain embodiments, an anti-MMP-9 antibody suitable for use with the disclosed methods comprises a heavy chain comprising an amino acid having at least 95% (e.g., at least 95%, 96%, 97%, 98%, 99%, or more) sequence identity to the amino acid sequence of SEQ ID NO: 39 and a light chain comprising an amino acid sequence having at least 95% (e.g., at least 95%, 96%, 97%, 98%, 99%, or more) sequence identity to the amino acid sequence of SEQ ID NO: 18. In certain embodiments, an anti-MMP-9 antibody suitable for use with the disclosed methods comprises a heavy chain comprising an amino acid having at least 99% (e.g., at least 99%, or more) sequence identity to the amino acid sequence of SEQ ID NO: 39 and a light chain comprising an amino acid sequence having at least 99% (e.g., at least 99%, or more) sequence identity to the amino acid sequence of SEQ ID NO: 18. In certain embodiments, an anti-MMP-9 antibody suitable for use with the disclosed methods comprises a heavy chain comprising an amino acid having 100% sequence identity to the amino acid sequence of SEQ ID NO: 39 and a light chain comprising an amino acid sequence having 100% sequence identity to the amino acid sequence of SEQ ID NO: 18.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 19 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 19 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 19 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 19 and a VL comprising an amino acid sequence having at least 95% (e.g., at least 95%, 96%, 97%, 98%, 99%, or more) sequence identity to the amino acid sequence of SEQ ID NO: 6. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 19 and a VL comprising an amino acid sequence having at least 99% (e.g., at least 99%, or more) sequence identity to the amino acid sequence of SEQ ID NO: 6. In certain embodiments, an anti-MMP-9 antibody suitable for use with the disclosed methods comprises a VH comprising an amino acid having 100% sequence identity to the amino acid sequence of SEQ ID NO: 19 and a VL comprising ID NO: 6.

In certain embodiments, an anti-MMP-9 antibody suitable for use with the disclosed methods comprises a heavy chain variable region comprising an HCDR1 comprising the amino acid sequence of SEQ ID NO: 21, an HCDR2 comprising the amino acid sequence of SEQ ID NO: 22, and an HCDR3 comprising the amino acid sequence of SEQ ID NO: 23, and a light chain variable region comprising a light chain complementarity determining region 1 (LCDR1) comprising the amino acid sequence of SEQ ID NO: 24, an LCDR2 comprising the amino acid sequence of SEQ ID NO: 25, and an LCDR3 comprising the amino acid sequence of SEQ ID NO: 26.

In certain embodiments, an anti-MMP-9 antibody suitable for use with the disclosed methods comprises a light chain comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 27. In certain embodiments, an anti-MMP-9 antibody suitable for use with the disclosed methods comprises a light chain comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 27. In certain embodiments, an anti-MMP-9 antibody suitable for use with the disclosed methods comprises a light chain comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 27. In certain embodiments, an anti-MMP-9 antibody suitable for use with the disclosed methods comprises a light chain comprising an amino acid sequence having at least 95% (e.g., at least 95%, 96%, 97%, 98%, 99%, or more) sequence identity to the amino acid sequence of SEQ ID NO: 27. In certain embodiments, an anti-MMP-9 antibody suitable for use with the disclosed methods comprises a light chain comprising an amino acid sequence having at least 99% (e.g., at least 99%, or more) sequence identity to the amino acid sequence of SEQ ID NO: 27. In certain embodiments, an anti-MMP-9 antibody suitable for use with the disclosed methods comprises a light chain comprising an amino acid sequence having 100% sequence identity to the amino acid sequence of SEQ ID NO: 27.

In certain embodiments, an anti-MMP-9 antibody suitable for use with the disclosed methods comprises a light chain comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 38. In certain embodiments, an anti-MMP-9 antibody suitable for use with the disclosed methods comprises a light chain comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 38. In certain embodiments, an anti-MMP-9 antibody suitable for use with the disclosed methods comprises a light chain comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 38. In certain embodiments, an anti-MMP-9 antibody suitable for use with the disclosed methods comprises a light chain comprising an amino acid sequence having at least 95% (e.g., at least 95%, 96%, 97%, 98%, 99%, or more) sequence identity to the amino acid sequence of SEQ ID NO: 38. In certain embodiments, an anti-MMP-9 antibody suitable for use with the disclosed methods comprises a light chain comprising an amino acid sequence having at least 99% (e.g., at least 99%, or more) sequence identity to the amino acid sequence of SEQ ID NO: 38. In certain embodiments, an anti-MMP-9 antibody suitable for use with the disclosed methods comprises a light chain comprising an amino acid sequence having 100% sequence identity to the amino acid sequence of SEQ ID NO: 38.

In certain embodiments, an anti-MMP-9 antibody suitable for use with the disclosed methods comprises a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 28. In certain embodiments, an anti-MMP-9 antibody suitable for use with the disclosed methods comprises a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 28. In certain embodiments, an anti-MMP-9 antibody suitable for use with the disclosed methods comprises a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 28. In certain embodiments, an anti-MMP-9 antibody suitable for use with the disclosed methods comprises a VL comprising an amino acid sequence having at least 95% (e.g., at least 95%, 96%, 97%, 98%, 99%, or more) sequence identity to the amino acid sequence of SEQ ID NO: 28. In certain embodiments, an anti-MMP-9 antibody suitable for use with the disclosed methods comprises a VL comprising an amino acid sequence having at least 99% (e.g., at least 99%, or more) sequence identity to the amino acid sequence of SEQ ID NO: 28. In certain embodiments, an anti-MMP-9 antibody suitable for use with the disclosed methods comprises a VL comprising an amino acid sequence having 100% sequence identity to the amino acid sequence of SEQ ID NO: 28.

In certain embodiments, an anti-MMP-9 antibody suitable for use with the disclosed methods comprises a light chain variable region comprising a light chain complementarity determining region 1 (LCDR1) comprising the amino acid sequence of SEQ ID NO: 29, an LCDR2 comprising the amino acid sequence of SEQ ID NO: 30, and an LCDR3 comprising the amino acid sequence of SEQ ID NO: 31.

In certain embodiments, an anti-MMP-9 antibody suitable for use with the disclosed methods comprises a heavy chain comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 33 and a light chain comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 32. In certain embodiments, an anti-MMP-9 antibody suitable for use with the disclosed methods comprises a heavy chain comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 33 and a light chain comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 32. In certain embodiments, an anti-MMP-9 antibody suitable for use with the disclosed methods comprises a heavy chain comprising an amino acid having at least 90% (e.g., at least 90%, 91%, 92%, 93%, 94%, 95%, 96%, 97%, 98%, 99%, or more) sequence identity to the amino acid sequence of SEQ ID NO: 33 and a light chain comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 32. In certain embodiments, an anti-MMP-9 antibody suitable for use with the disclosed methods comprises a heavy chain comprising an amino acid having at least 95% (e.g., at least 95%, 96%, 97%, 98%, 99%, or more) sequence identity to the amino acid sequence of SEQ ID NO: 33 and a light chain comprising an amino acid sequence having at least 95% (e.g., at least 95%, 96%, 97%, 98%, 99%, or more) sequence identity to the amino acid sequence of SEQ ID NO: 32. In certain embodiments, an anti-MMP-9 antibody suitable for use with the disclosed methods comprises a heavy chain comprising an amino acid having at least 99% (e.g., at least 99%, or more) sequence identity to the amino acid sequence of SEQ ID NO: 33 and a light chain comprising an amino acid sequence having at least 99% (e.g., at least 99%, or more) sequence identity to the amino acid sequence of SEQ ID NO: 32. In certain embodiments, an anti-MMP-9 antibody suitable for use with the disclosed methods comprises a heavy chain comprising an amino acid having 100% sequence identity to the amino acid sequence of SEQ ID NO: 33 and a light chain comprising an amino acid sequence having 100% sequence identity to the amino acid sequence of SEQ ID NO: 32.

In certain embodiments, an anti-MMP-9 antibody suitable for use with the disclosed methods comprises a heavy chain comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 33 and a light chain comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 49. In certain embodiments, an anti-MMP-9 antibody suitable for use with the disclosed methods comprises a heavy chain comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 33 and a light chain comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 49. In certain embodiments, an anti-MMP-9 antibody suitable for use with the disclosed methods comprises a heavy chain comprising an amino acid having at least 90% (e.g., at least 90%, 91%, 92%, 93%, 94%, 95%, 96%, 97%, 98%, 99%, or more) sequence identity to the amino acid sequence of SEQ ID NO: 33 and a light chain comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 49. In certain embodiments, an anti-MMP-9 antibody suitable for use with the disclosed methods comprises a heavy chain comprising an amino acid having at least 95% (e.g., at least 95%, 96%, 97%, 98%, 99%, or more) sequence identity to the amino acid sequence of SEQ ID NO: 33 and a light chain comprising an amino acid sequence having at least 95% (e.g., at least 95%, 96%, 97%, 98%, 99%, or more) sequence identity to the amino acid sequence of SEQ ID NO: 49. In certain embodiments, an anti-MMP-9 antibody suitable for use with the disclosed methods comprises a heavy chain comprising an amino acid having at least 99% (e.g., at least 99%, or more) sequence identity to the amino acid sequence of SEQ ID NO: 33 and a light chain comprising an amino acid sequence having at least 99% (e.g., at least 99%, or more) sequence identity to the amino acid sequence of SEQ ID NO: 49. In certain embodiments, an anti-MMP-9 antibody suitable for use with the disclosed methods comprises a heavy chain comprising an amino acid having 100% sequence identity to the amino acid sequence of SEQ ID NO: 33 and a light chain comprising an amino acid sequence having 100% sequence identity to the amino acid sequence of SEQ ID NO: 49.

In certain embodiments, an anti-MMP-9 antibody suitable for use with the disclosed methods comprises a heavy chain comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 50 and a light chain comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 32. In certain embodiments, an anti-MMP-9 antibody suitable for use with the disclosed methods comprises a heavy chain comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 50 and a light chain comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 32. In certain embodiments, an anti-MMP-9 antibody suitable for use with the disclosed methods comprises a heavy chain comprising an amino acid having at least 90% (e.g., at least 90%, 91%, 92%, 93%, 94%, 95%, 96%, 97%, 98%, 99%, or more) sequence identity to the amino acid sequence of SEQ ID NO: 50 and a light chain comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 32. In certain embodiments, an anti-MMP-9 antibody suitable for use with the disclosed methods comprises a heavy chain comprising an amino acid having at least 95% (e.g., at least 95%, 96%, 97%, 98%, 99%, or more) sequence identity to the amino acid sequence of SEQ ID NO: 50 and a light chain comprising an amino acid sequence having at least 95% (e.g., at least 95%, 96%, 97%, 98%, 99%, or more) sequence identity to the amino acid sequence of SEQ ID NO: 32. In certain embodiments, an anti-MMP-9 antibody suitable for use with the disclosed methods comprises a heavy chain comprising an amino acid having at least 99% (e.g., at least 99%, or more) sequence identity to the amino acid sequence of SEQ ID NO: 50 and a light chain comprising an amino acid sequence having at least 99% (e.g., at least 99%, or more) sequence identity to the amino acid sequence of SEQ ID NO: 32. In certain embodiments, an anti-MMP-9 antibody suitable for use with the disclosed methods comprises a heavy chain comprising an amino acid having 100% sequence identity to the amino acid sequence of SEQ ID NO: 50 and a light chain comprising an amino acid sequence having 100% sequence identity to the amino acid sequence of SEQ ID NO: 32.

In certain embodiments, an anti-MMP-9 antibody suitable for use with the disclosed methods comprises a heavy chain comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 50 and a light chain comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 49. In certain embodiments, an anti-MMP-9 antibody suitable for use with the disclosed methods comprises a heavy chain comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 50 and a light chain comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 49. In certain embodiments, an anti-MMP-9 antibody suitable for use with the disclosed methods comprises a heavy chain comprising an amino acid having at least 90% (e.g., at least 90%, 91%, 92%, 93%, 94%, 95%, 96%, 97%, 98%, 99%, or more) sequence identity to the amino acid sequence of SEQ ID NO: 50 and a light chain comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 49. In certain embodiments, an anti-MMP-9 antibody suitable for use with the disclosed methods comprises a heavy chain comprising an amino acid having at least 95% (e.g., at least 95%, 96%, 97%, 98%, 99%, or more) sequence identity to the amino acid sequence of SEQ ID NO: 50 and a light chain comprising an amino acid sequence having at least 95% (e.g., at least 95%, 96%, 97%, 98%, 99%, or more) sequence identity to the amino acid sequence of SEQ ID NO: 49. In certain embodiments, an anti-MMP-9 antibody suitable for use with the disclosed methods comprises a heavy chain comprising an amino acid having at least 99% (e.g., at least 99%, or more) sequence identity to the amino acid sequence of SEQ ID NO: 50 and a light chain comprising an amino acid sequence having at least 99% (e.g., at least 99%, or more) sequence identity to the amino acid sequence of SEQ ID NO: 49. In certain embodiments, an anti-MMP-9 antibody suitable for use with the disclosed methods comprises a heavy chain comprising an amino acid having 100% sequence identity to the amino acid sequence of SEQ ID NO: 50 and a light chain comprising an amino acid sequence having 100% sequence identity to the amino acid sequence of SEQ ID NO: 49.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 51 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 34. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 51 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 34. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 51 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 34. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 51 and a VL comprising an amino acid sequence having at least 95% (e.g., at least 95%, 96%, 97%, 98%, 99%, or more) sequence identity to the amino acid sequence of SEQ ID NO: 34. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 51 and a VL comprising an amino acid sequence having at least 99% (e.g., at least 99%, or more) sequence identity to the amino acid sequence of SEQ ID NO: 34. In certain embodiments, an anti-MMP-9 antibody suitable for use with the disclosed methods comprises a VH comprising an amino acid having 100% sequence identity to the amino acid sequence of SEQ ID NO: 51 and a VL comprising an amino acid sequence having 100% sequence identity to the amino acid sequence of SEQ ID NO: 34.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 51 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 52. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 51 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 52. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 51 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 52. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 51 and a VL comprising an amino acid sequence having at least 95% (e.g., at least 95%, 96%, 97%, 98%, 99%, or more) sequence identity to the amino acid sequence of SEQ ID NO: 52. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 51 and a VL comprising an amino acid sequence having at least 99% (e.g., at least 99%, or more) sequence identity to the amino acid sequence of SEQ ID NO: 52. In certain embodiments, an anti-MMP-9 antibody suitable for use with the disclosed methods comprises a VH comprising an amino acid having 100% sequence identity to the amino acid sequence of SEQ ID NO: 51 and a VL comprising an amino acid sequence having 100% sequence identity to the amino acid sequence of SEQ ID NO: 52.

In certain embodiments, an anti-MMP-9 antibody suitable for use with the disclosed methods comprises a heavy chain comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 43 and a light chain comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 44. In certain embodiments, an anti-MMP-9 antibody suitable for use with the disclosed methods comprises a heavy chain comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 43 and a light chain comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 44. In certain embodiments, an anti-MMP-9 antibody suitable for use with the disclosed methods comprises a heavy chain comprising an amino acid having at least 90% (e.g., at least 90%, 91%, 92%, 93%, 94%, 95%, 96%, 97%, 98%, 99%, or more) sequence identity to the amino acid sequence of SEQ ID NO: 43 and a light chain comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 44. In certain embodiments, an anti-MMP-9 antibody suitable for use with the disclosed methods comprises a heavy chain comprising an amino acid having at least 95% (e.g., at least 95%, 96%, 97%, 98%, 99%, or more) sequence identity to the amino acid sequence of SEQ ID NO: 43 and a light chain comprising an amino acid sequence having at least 95% (e.g., at least 95%, 96%, 97%, 98%, 99%, or more) sequence identity to the amino acid sequence of SEQ ID NO: 44. In certain embodiments, an anti-MMP-9 antibody suitable for use with the disclosed methods comprises a heavy chain comprising an amino acid having at least 99% (e.g., at least 99%, or more) sequence identity to the amino acid sequence of SEQ ID NO: 43 and a light chain comprising an amino acid sequence having at least 99% (e.g., at least 99%, or more) sequence identity to the amino acid sequence of SEQ ID NO: 44. In certain embodiments, an anti-MMP-9 antibody suitable for use with the disclosed methods comprises a heavy chain comprising an amino acid having 100% sequence identity to the amino acid sequence of SEQ ID NO: 43 and a light chain comprising an amino acid sequence having 100% sequence identity to the amino acid sequence of SEQ ID NO: 44.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 83 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 84. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 83 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 84. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 83 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 84. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 83 and a VL comprising an amino acid sequence having at least 95% (e.g., at least 95%, 96%, 97%, 98%, 99%, or more) sequence identity to the amino acid sequence of SEQ ID NO: 84. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 83 and a VL comprising an amino acid sequence having at least 99% (e.g., at least 99%, or more) sequence identity to the amino acid sequence of SEQ ID NO: 84. In certain embodiments, an anti-MMP-9 antibody suitable for use with the disclosed methods comprises a VH comprising an amino acid having 100% sequence identity to the amino acid sequence of SEQ ID NO: 83 and a VL comprising an amino acid sequence having 100% sequence identity to the amino acid sequence of SEQ ID NO: 84.

In certain embodiments, an anti-MMP-9 antibody suitable for use with the disclosed methods comprises a heavy chain variable region comprising an HCDR1 comprising the amino acid sequence of SEQ ID NO: 85, an HCDR2 comprising the amino acid sequence of SEQ ID NO: 86, and an HCDR3 comprising the amino acid sequence of SEQ ID NO: 87, and a light chain variable region comprising a light chain complementarity determining region 1 (LCDR1) comprising the amino acid sequence of SEQ ID NO: 88, an LCDR2 comprising the amino acid sequence of SEQ ID NO: 89, and an LCDR3 comprising the amino acid sequence of SEQ ID NO: 90.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 91 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 92. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 91 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 92. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 91 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 92. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 91 and a VL comprising an amino acid sequence having at least 95% (e.g., at least 95%, 96%, 97%, 98%, 99%, or more) sequence identity to the amino acid sequence of SEQ ID NO: 92. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 91 and a VL comprising an amino acid sequence having at least 99% (e.g., at least 99%, or more) sequence identity to the amino acid sequence of SEQ ID NO: 92. In certain embodiments, an anti-MMP-9 antibody suitable for use with the disclosed methods comprises a VH comprising an amino acid having 100% sequence identity to the amino acid sequence of SEQ ID NO: 91 and a VL comprising an amino acid sequence having 100% sequence identity to the amino acid sequence of SEQ ID NO: 92.

In certain embodiments, an anti-MMP-9 antibody suitable for use with the disclosed methods comprises a heavy chain variable region comprising an HCDR1 comprising the amino acid sequence of SEQ ID NO: 93, an HCDR2 comprising the amino acid sequence of SEQ ID NO: 94, and an HCDR3 comprising the amino acid sequence of SEQ ID NO: 95, and a light chain variable region comprising a light chain complementarity determining region 1 (LCDR1) comprising the amino acid sequence of SEQ ID NO: 96, an LCDR2 comprising the amino acid sequence of SEQ ID NO: 97, and an LCDR3 comprising the amino acid sequence of SEQ ID NO: 98.

In certain embodiments, an anti-MMP-9 antibody suitable for use with the disclosed methods comprises a VH comprising an amino acid having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 99 and a VL comprising an amino acid sequence having at least 80% (e.g., at least 80%, 81%, 82%, 83%, 84%, 85%, 86%, 87%, 88%, 89%, 90%, 91%, 92%, 93%, 94%, 95%, 96%, 97%, 98%, 99%, or more) sequence identity to the amino acid sequence of SEQ ID NO: 100. In certain embodiments, an anti-MMP-9 antibody suitable for use with the disclosed methods comprises a VH comprising an amino acid having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 99 and a VL comprising an amino acid sequence having at least 85% (e.g., at least 85%, 86%, 87%, 88%, 89%, 90%, 91%, 92%, 93%, 94%, 95%, 96%, 97%, 98%, 99%, or more) sequence identity to the amino acid sequence of SEQ ID NO: 100. In certain embodiments, an anti-MMP-9 antibody suitable for use with the disclosed methods comprises a VH comprising an amino acid having at least 90% (e.g., at least 90%, 91%, 92%, 93%, 94%, 95%, 96%, 97%, 98%, 99%, or more) sequence identity to the amino acid sequence of SEQ ID NO: 99 and a VL comprising an amino acid sequence having at least 90% (e.g., at least 90%, 91%, 92%, 93%, 94%, 95%, 96%, 97%, 98%, 99%, or more) sequence identity to the amino acid sequence of SEQ ID NO: 100. In certain embodiments, an anti-MMP-9 antibody suitable for use with the disclosed methods comprises a VH comprising an amino acid having at least 95% (e.g., at least 95%, 96%, 97%, 98%, 99%, or more) sequence identity to the amino acid sequence of SEQ ID NO: 99 and a VL comprising an amino acid sequence having at least 95% (e.g., at least 95%, 96%, 97%, 98%, 99%, or more) sequence identity to the amino acid sequence of SEQ ID NO: 100. In certain embodiments, an anti-MMP-9 antibody suitable for use with the disclosed methods comprises a VH comprising an amino acid having at least 99% (e.g., at least 99%, or more) sequence identity to the amino acid sequence of SEQ ID NO: 99 and a VL comprising an amino acid sequence having at least 99% (e.g., at least 99%, or more) sequence identity to the amino acid sequence of SEQ ID NO: 100. In certain embodiments, an anti-MMP-9 antibody suitable for use with the disclosed methods comprises a VH comprising an amino acid having 100% sequence identity to the amino acid sequence of SEQ ID NO: 99 and a VL comprising an amino acid sequence having 100% sequence identity to the amino acid sequence of SEQ ID NO: 100.

In certain embodiments, an anti-MMP-9 antibody suitable for use with the disclosed methods comprises a heavy chain variable region comprising an HCDR1 comprising the amino acid sequence of SEQ ID NO: 101, an HCDR2 comprising the amino acid sequence of SEQ ID NO: 102, and an HCDR3 comprising the amino acid sequence of SEQ ID NO: 103, and a light chain variable region comprising a light chain complementarity determining region 1 (LCDR1) comprising the amino acid sequence of SEQ ID NO: 104, an LCDR2 comprising the amino acid sequence of SEQ ID NO: 105, and an LCDR3 comprising the amino acid sequence of SEQ ID NO: 106.

As described herein, SEQ ID NO: 1, 17, 33, 35, 39, 43, and 50 pertain to an anti-MMP-9 heavy chain. As described herein, SEQ ID NO: 3-5, 19, 46, 48, 51, 53-56 pertain to an anti-MMP-9 heavy chain variable region or VH. As described herein, SEQ ID NO: 2, 18, 27, 32, 36, 38, 44, and 49 pertain to an anti-MMP-9 light chain, As described herein, SEQ ID NO: 8, 21, 45 pertain to an anti-MMP-9 light chain variable region or VL. As described herein, SEQ ID NO: 13, 26, and 51 correspond to an anti-MMP-9 heavy chain CDR1. As described herein, SEQ ID NO: 9 and 22 correspond to an anti-MMP-9 heavy chain CDR2. As described herein, SEQ ID NO: 10 and 23 correspond to an anti-MMP-9 heavy chain CDR3. As described herein, SEQ ID NO: 11, 24, and 29 correspond to an anti-MMP-9 light chain CDR1. As described herein, SEQ ID NO: 12, 25, and 30 correspond to an anti-MMP-9 light chain CDR2. As described herein, SEQ ID NO: 26 and 31 correspond to an anti-MMP-9 light chain CDR3. As described herein, SEQ ID NO: 14 and 15 pertain to the MMP-9 protein. As described herein, SEQ ID NO: 16 corresponds to a MMP-9 signal peptide. As described herein, SEQ ID NO: 40 corresponds to a neo-epitope. As described herein, SEQ ID NO: 41 corresponds to a neo-epitope fragment. As described herein, SEQ ID NO: 42 corresponds to an MMP-9 total cleavage site.

In certain embodiments, the anti-MMP-9 antibodies is andecaliximab or an antigen-binding fragment thereof. Andecaliximab binds MMP-9 at an arginine residue at position 162 of the MMP-9 amino acid sequence (R162). US/2012/0135004. Additional MMP-9 residues that are bound by andecaliximab are E111, D113, and I198. R162, E111, D113, and I198 are near a Ca2+ ion binding pocket on MMP-9. US/2012/0135004. Accordingly, in some embodiments, administration of an andecaliximab or an antigen-binding fragment thereof results in binding of andecaliximab to these residues.

Diagnostic Use of Antibodies

In some embodiments, antibodies or antigen-binding fragments thereof described herein are used to detect subjects having certain disorders such as gHO (e.g., FOP) using a conventional immunoassay, such as an enzyme linked immunosorbent assays (ELISA), a radioimmunoassay or tissue immunohistochemistry. In some embodiments, the method comprises contacting a biological sample with the antibody or antigen-binding fragment described herein such that the antibody detects the one or more disorders. In some embodiments, the antibody or antigen-binding fragment is labeled with a detectable marker, such as a fluorescent label.

In some embodiments, the antibody or antigen-binding fragment is labeled with horseradish peroxidase, alkaline phosphatase, β-galactosidase, acetylcholinesterase, streptavidin/biotin and avidin/biotin, umbelliferone, fluorescein, fluorescein isothiocyanate, rhodamine, dichlorotriazinylamine fluorescein, dansyl chloride or phycoerythrin, luminol. $^{125}$I, $^{131}$I, $^{35}$S or $^{3}$H. In some embodiments, MMP-9 can be assayed in biological fluids of a subject by one of many known techniques in the art.

Inhibitory Polypeptides Targeting MMP-9

In some embodiments, methods disclosed herein contemplate use of one or more inhibitory peptides targeting MMP-9. Accordingly, provided herein are methods for treating gHO (e.g., FOP) in a subject, which comprise administration of one or more triple-helical peptide inhibitors. Triple-helical peptide inhibitors include but are not limited to α1(V)GlyΨ{PO$_2$H—CH$_2$} Val THPI [C$_6$-(Gly-Pro-Hyp)$_4$-Gly-Pro-Pro-GlyΨ{PO$_2$H—CH$_2$}(R,S)Val-Val-Gly-Glu-Gln-Gly-Glu-Gln-Gly-Pro-Pro-(Gly-Pro-Hyp)$_4$-NH$_2$] (SEQ ID NO: 61). A stabilized version of α1(V) GlyΨ{PO$_2$H—CH$_2$} Val THPI [C$_6$-(Gly-Pro-Hyp)$_4$-Gly-Pro-Pro-Gly {PO$_2$H—CH$_2$}(R,S)Val-Val-Gly-Glu-Gln-Gly-Glu-Gln-Gly-Pro-Pro-(Gly-Pro-Hyp)$_4$-NH$_2$] is α1(V) Gly{PO$_2$H—CH$_2$} Val [mep$_{14, 32}$,Flp$_{15, 33}$] (SEQ ID NO: 62) THPI, where mep was (2S,4R)-4-methylproline and Flp was (2S,4R)-4-fluoroproline. (Bhowmick M, Tokmina-Roszyk D, Onwuha-Ekpete L, Harmon K, Robichaud T, Fuerst R, et al. Second generation triple-helical peptide transition state analog matrix metalloproteinase inhibitors. J Med Chem. (2017) 60:3814-27. doi: 10.1021/acs.jmedchem.7b00018). α1(V)GlyΨ{PO$_2$H—CH$_2$} Val [mep$_{14, 32}$,Flp$_{15, 33}$] THPI exhibited K$_i$ values of 90.6 nM against MMP-9 at 25° Celsius and 0.98 nM at 37° Celsius. Triple-helical peptide inhibitors have been found to be stable to proteolysis in numerous in vitro experiments and in vivo in rats. α1(V)GlyΨ{PO$_2$H—CH$_2$} Val [mep$_{14, 32}$,Flp$_{15, 33}$] THPI effectively reduced clinical severity and weight loss in a mouse model of multiple sclerosis.

As disclosed in WO2023192880, non-limiting examples of non-antibody protein or peptide inhibitors of MMP-9 include proteins from the tissue inhibitors of metalloproteinase (TIMP) family such as TIMP-1, TIMP-3 and the like, FFAGLDD peptide (SEQ ID NO: 81), FFAGLDD TFA, cyclic CTTHWGFTLC (SEQ ID NO: 82), cyclic CTTHWGFTLC TFA, and the like.

Small Molecule Inhibitors of MMP-9

In some embodiments, methods disclosed herein contemplate use of one or more small molecule inhibitors of MMP-9. Accordingly, provided herein are various MMP-9 small molecule inhibitors suitable for the treatment of a subject having gHO (e.g., FOP).

As disclosed in WO/2023/192880, non-limiting examples of small molecules that inhibit MMP-9 include actinonin, ageladine A TFA, apigenin-7-glucuronide, ARP 100, astragaloside IV, BR351, chlorhexidine dihydrochloride, cipemastat, CMC2.24, CP-471474, CP-544439, FSL-1 TFA, ginkgolide C, ilomastat (also referred to as GM6001), JNJ0966, luteolin 7-O-glucuronide, marimastat, MMP-2/MMP-9 Inhibitor I, MMP-2/MMP-9 Inhibitor II, MMP3 inhibitor 1, MMP-9-IN-1, MMP-9 Inhibitor I, MMP-9 Inhibitor II, MMP-9/MMP-13 inhibitor I, MMP Inhibitor II, MMP13-IN-3, MMPI-1154, morroniside, ND-336, NNGH, (R)-ND-336, PF-00356231 hydrochloride, PD-166793, prinomastat, prinomastat hydrochloride, salvianolic acid A, S 3304, SB-3CT, SM-7368, tanomastat, tetracycline derivatives such as doxycycline, incyclinide, and minocycline, UK 356618, UK-370106, XL-784, and the like. MMP-9 inhibitors are described in, for example, Fields (Cells. 2019 September; 8(9): 984).

In some embodiments, MMP-9 small molecule inhibitors comprise thiirane-based inhibitors, which bind the active site of MMP-9. Examples of thiirane-based inhibitors include, without limitation, SB-3CT, the O-phosphate prodrug form of SB-3CT, and ND-322. In some embodiments, the thiirane-based inhibitor comprises an O-phosphate prodrug form of SB-3CT. Without wishing to be bound by any theory, SB-3CT may act through increased CD8$^+$ T cell cytotoxicity, activation of lymphocytes, and potentially inhibition of PD-L1. In some embodiments, SB-3CT is administered at a dosage of 5, 10, 15, 20, 25, 30, 35, 40, 45, or 50 mg/kg/day. The chemical structure of SB-3CT is provided below.

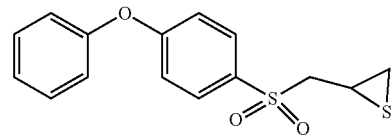 [SMILES: O=S(=O)(CC1CS1)c1ccc(Oc2ccccc2)cc1]

In some embodiments, the small molecule inhibitor is ND-322 (chemical structure provided below).

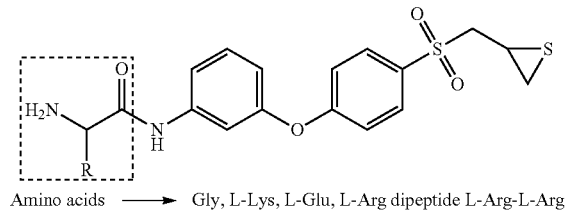

Amino acids ⟶ Gly, L-Lys, L-Glu, L-Arg dipeptide L-Arg-L-Arg

In some embodiments, a small molecule inhibitor of MMP-9 is a non-active site small molecule inhibitor. An example of a non-active site small molecule inhibitor of MMP-9 is N-[4-(difluoromethoxy)phenyl]-2-[(4-oxo-6-propyl-1H-pyrimidin-2-yl) sulfanyl]-acetamide, which binds MMP-9 at the hemopexin domain with a K$_D$ of 2.1 mM. In MDA-MB-435 mouse models, N-[4-(difluoromethoxy)phenyl]-2-[(4-oxo-6-propyl-1H-pyrimidin-2-yl) sulfanyl]-acetamide reduced tumor growth and metastasis. The structure of N-[4-(difluoromethoxy)phenyl]-2-[(4-oxo-6-propyl-1H-pyrimidin-2-yl) sulfanyl]-acetamide is provided below.

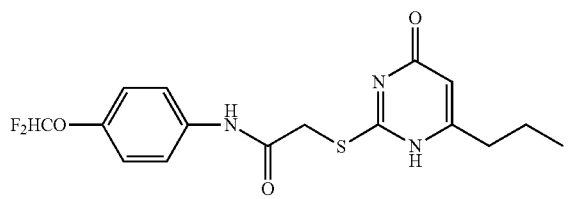 [SMILES: CCCc1cc(=O)nc(SCC(=O)Nc2ccc(OC(F)F)cc2)[nH]1]

In some embodiments, a non-active site small molecule inhibitor of MMP-9 is N-4-fluorophenyl)-4-(4-oxo-3,4,5,6,7,8-hexahydroquinazolin-2-ylthio) butanamide, which interferes with the association of MMP-9 with α4b1 integrin and CD44, thereby causing the dissociation of epidermal growth factor receptor (EGFR) from the β1 integrin subunit and CD44. N-(4-fluorophenyl)-4-(4-oxo-3,4,5,6,7,8-hexahydroquinazolin-2-ylthio) butanamide binds MMP-9 with a $K_D$ of 320 nM. The chemical structure of N-(4-fluorophenyl)-4-(4-oxo-3,4,5,6,7,8-hexahydroquinazolin-2-ylthio) butanamide is provided below.

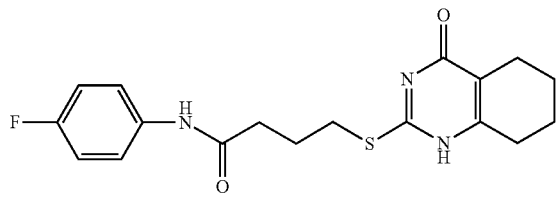 [SMILES: O=C(CCCSc1nc(=O)c2c([nH]1)CCCC2)Nc1ccc(F)cc1]

In some embodiments, the non-active site small molecule inhibitor comprises JNJ0966 or N-(2-((2-methoxyphenyl)amino)-4'-methyl-[4,5'-bithiazol]-2'yl) acetamide. JNJ0966 binds selectively to MMP-9 with a $K_D$ of 5.0 mM, prevents the activation of pro-MMP-9, inhibits the migration of HT1080 cells, and penetrates the blood-brain barrier. The chemical structure of N-(2-((2-methoxyphenyl)amino)-4'-methyl-[4,5'-bithiazol]-2'yl) acetamide is provided below.

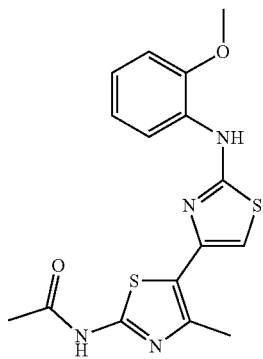 [SMILES: COc1ccccc1Nc1nc(-c2sc(NC(C)=O)nc2C)cs1]

As used herein in reference to small molecules, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein in reference to small molecules, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers, enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers or are prepared by methods known to those skilled in the art.

A variety of methods are known to administer one or more small molecules of the present invention. As will be appreciated by a skilled artisan, the route and/or mode of administration will vary depending upon the desired results. In some embodiments, a small molecule is prepared with a carrier that protects the compound against rapid release, such as a controlled release formulation, including implants, transdermal patches, and microencapsulated delivery systems. Biodegradable, biocompatible polymers can be used, such as ethylene vinyl acetate, polyethylene glycol (PEG), polyanhydrides, polyglycolic acid, collagen, polyorthoesters, and polylactic acid. Many methods for the preparation of such formulations are patented or generally known to those skilled in the art.

MMP-9 Inhibitory Nucleic Acids

In some embodiments, disclosed are methods for treatment of gHO (e.g., FOP) by administering an effective amount of inhibitory nucleic acid molecules (e.g., inhibitory RNA). In some embodiments, an inhibitory RNA suitable for use with the disclosed methods comprises an antisense oligonucleotide (ASO), a short interfering RNA (siRNA), a microRNA (miRNA), a short hairpin RNA (shRNA), or an shRNA-adapted microRNA (shmiRNA).

Methods disclosed herein may include contacting a target nucleic acid (e.g., pre-mRNA or mRNA) encoding MMP-9 with an inhibitory RNA molecule capable of hybridizing to the MMP-9 target nucleic acid and promoting its degradation by, e.g., promoting recruitment of RNase H and by inhibition of translation (e.g., through steric hinderance). The MMP-9 target nucleic acid may be a mammalian MMP-9 mRNA sequence.

The inhibitory RNA molecules suitable for use with the methods disclosed herein include a nucleoside sequence that is at least substantially complementary or fully complementary to a region of the sequence of MMP-9 mRNA or variants thereof, said complementarity being sufficient to yield specific binding under intracellular conditions. For example, the disclosure contemplates an inhibitory RNA having an antisense sequence that is complementary to at least 7 (e.g., at least 7, 8, 9, 10, 11, 12, 13, 14, 15, 16, 17, 18, 19, 20, 21, 22, or more) consecutive nucleotides of one or more regions of an MMP-9 mRNA. In some embodiments, the inhibitory RNA molecule has an antisense sequence that is complementary to 7 consecutive nucleotides of one or more regions of an MMP-9 mRNA. In some embodiments, the inhibitory RNA molecule has an antisense sequence that is complementary to 8 consecutive nucleotides of one or more regions of an MMP-9 mRNA. In some embodiments, the inhibitory RNA molecule has an antisense sequence that is complementary to 9 consecutive nucleotides of one or more regions of an MMP-9 mRNA. In some embodiments, the inhibitory RNA molecule has an antisense sequence that is complementary to 10 consecutive nucleotides of one or more regions of an MMP-9 mRNA. In some embodiments, the inhibitory RNA molecule has an antisense sequence that is complementary to 11 consecutive nucleotides of one or more regions of an MMP-9 mRNA. In some embodiments, the inhibitory RNA molecule has an antisense sequence that is complementary to 12 consecutive nucleotides of one or more regions of an MMP-9 mRNA. In some embodiments, the inhibitory RNA molecule has an antisense sequence that is complementary to 13 consecutive nucleotides of one or more regions of an MMP-9 mRNA. In some embodiments, the inhibitory RNA molecule has an antisense sequence that is complementary to 14 consecutive nucleotides of one or more regions of an MMP-9 mRNA. In some embodiments, the inhibitory RNA molecule has an antisense sequence that is complementary to 15 consecutive nucleotides of one or more regions of an MMP-9 mRNA. In some embodiments, the inhibitory RNA molecule has an antisense sequence that is complementary to 16 consecutive nucleotides of one or more regions of an MMP-9 mRNA. In some embodiments, the inhibitory RNA molecule has an antisense sequence that is complementary to 17 consecutive nucleotides of one or more regions of an MMP-9 mRNA. In some embodiments, the inhibitory RNA molecule has an antisense sequence that is complementary to 18 consecutive nucleotides of one or more regions of an MMP-9 mRNA. In some embodiments, the inhibitory RNA molecule has an antisense sequence that is complementary to 19 consecutive nucleotides of one or more regions of an MMP-9 mRNA. In some embodiments, the inhibitory RNA molecule has an antisense sequence that is complementary to 20 consecutive nucleotides of one or more regions of an MMP-9 mRNA. In some embodiments, the inhibitory RNA molecule has an antisense sequence that is complementary to 21 consecutive nucleotides of one or more regions of an MMP-9 mRNA. In some embodiments, the inhibitory RNA molecule has an antisense sequence that is complementary to 22 consecutive nucleotides of one or more regions of an MMP-9 mRNA. In some embodiments, the inhibitory RNA molecule has an antisense sequence that is complementary to 23 consecutive nucleotides of one or more regions of an MMP-9 mRNA. In some embodiments, the inhibitory RNA molecule has an antisense sequence that is complementary to 24 consecutive nucleotides of one or more regions of an MMP-9 mRNA. In some embodiments, the inhibitory RNA molecule has an antisense sequence that is complementary to 25 consecutive nucleotides of one or more regions of an MMP-9 mRNA. In some embodiments, the inhibitory RNA molecule has an antisense sequence that is complementary to 26 consecutive nucleotides of one or more regions of an MMP-9 mRNA. In some embodiments, the inhibitory RNA molecule has an antisense sequence that is complementary to 27 consecutive nucleotides of one or more regions of an MMP-9 mRNA. In some embodiments, the inhibitory RNA molecule has an antisense sequence that is complementary to 28 consecutive nucleotides of one or more regions of an MMP-9 mRNA. In some embodiments, the inhibitory RNA molecule has an antisense sequence that is complementary to 29 consecutive nucleotides of one or more regions of an MMP-9 mRNA. In some embodiments, the inhibitory RNA molecule has an antisense sequence that is complementary to 30 consecutive nucleotides of one or more regions of an MMP-9 mRNA. In yet another example, the inhibitory RNA molecule has an antisense sequence that is 100% complementary to the nucleotides of one or more regions of an MMP-9 mRNA.

The disclosure contemplates inhibitory RNA molecules that, when bound to one or more regions of an MMP-9 mRNA, form a duplex structure with the MMP-9 mRNA of between 7-22 (e.g., 7, 8, 9, 10, 11, 12, 13, 14, 15, 16, 17, 18, 19, 20, 21, or 22) nucleotides in length. For example, the duplex structure between the inhibitory RNA molecule and the MMP-9 mRNA may be 7 nucleotides in length. In some embodiments, the duplex structure between the inhibitory RNA molecule and the MMP-9 mRNA may be 8 nucleotides in length. In some embodiments, the duplex structure between the inhibitory RNA molecule and the MMP-9 mRNA may be 9 nucleotides in length. In some embodiments, the duplex structure between the inhibitory RNA molecule and the MMP-9 mRNA may be 10 nucleotides in length. In some embodiments, the duplex structure between the inhibitory RNA molecule and the MMP-9 mRNA may be 11 nucleotides in length. In some embodiments, the duplex structure between the inhibitory RNA molecule and the MMP-9 mRNA may be 12 nucleotides in length. In some embodiments, the duplex structure between the inhibitory RNA molecule and the MMP-9 mRNA may be 13 nucleotides in length. In some embodiments, the duplex structure between the inhibitory RNA molecule and the MMP-9 mRNA may be 14 nucleotides in length. In some embodiments, the duplex structure between the inhibitory RNA molecule and the MMP-9 mRNA may be 15 nucleotides in length. In some embodiments, the duplex structure between the inhibitory RNA molecule and the MMP-9 mRNA may be 16 nucleotides in length. In some embodiments, the duplex structure between the inhibitory RNA molecule and the MMP-9 mRNA may be 17 nucleotides in length. In some embodiments, the duplex structure between the inhibitory RNA molecule and the MMP-9 mRNA may be 18 nucleotides in length. In some embodiments, the duplex structure between the inhibitory RNA molecule and the MMP-9 mRNA may be 19 nucleotides in length. In some embodiments, the duplex structure between the inhibitory RNA molecule and the MMP-9 mRNA may be 20 nucleotides in length. In some embodiments, the duplex structure between the inhibitory RNA molecule and the MMP-9 mRNA may be 21 nucleotides in length. In yet another example, the duplex structure between the inhibitory RNA molecule and the MMP-9 mRNA may be 10 nucleotides in length. According to the disclosed methods and compositions, the duplex structure formed by an inhibitory RNA molecule (e.g., an agent having at least 90% (at least 91%, 92%, 93%, 94%, 95%, 96%, 97%, 98%, 99%, or more) sequence identity to the nucleic acid sequence of any one or more regions of an MMP-9 mRNA) may include at least one (e.g., at least 2, 3, 4, 5, 6, 7, 8, 9, 10, 11, 12, 13, 14, or 15) mismatch, where a mismatch may be an insertion of a nucleobase that is not present in the MMP-9 mRNA, a deletion of a nucleobase that is present in the MMP-9 mRNA, or a nucleobase that is not complementary to the MMP-9 mRNA. For example, the duplex structure may contain 1 mismatch. In some embodiments, the duplex structure contains 2 mismatches. In some embodiments, the duplex structure contains 3 mismatches. In some embodiments, the duplex structure contains 4 mismatches. In some embodiments, the duplex structure contains 5 mismatches. In some embodiments, the duplex structure contains 6 mismatches. In some embodiments, the duplex structure contains 7 mismatches. In some embodiments, the duplex structure contains 8 mismatches. In some embodiments, the duplex structure contains 9 mismatches. In some embodiments, the duplex structure contains 10 mismatches. In some embodiments, the duplex structure contains 11 mismatches. In some embodiments, the duplex structure contains 12 mismatches. In some embodiments, the duplex structure contains 13 mismatches. In some embodiments, the duplex structure contains 14 mismatches. In yet another example, the duplex structure contains 15 mismatches.

In some embodiments, the inhibitory RNA molecule of the disclosure is capable of modulating the expression of the MMP-9 target nucleic acid by inhibiting or downregulating the expression of the MMP-9 target nucleic acid (MMP-9 pre-mRNA or mRNA) in a cell. Such modulation produces an inhibition of expression of MMP-9 target nucleic acid of at least 10% (e.g., at least 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more) compared to the expression level of the target in the cell in the absence of treatment with the inhibitory RNA molecule. The modulation of MMP-9 expression may occur in vitro (e.g., in primary cell cultures, cell lines, or tissue organoids) or in vivo (e.g., upon administration to an animal, e.g., a mammal, e.g., a human). In some embodiments, inhibitory RNA molecules of the disclosure may be capable of inhibiting expression levels of MMP-9 mRNA in a cell by at least 60% (e.g., at least 65%, 70%, 75%, 80%, 85%, 90%, 91%, 92%, 93%, 94%, 95%, 96%, 97%, 98%, 99% or more) in vitro following application of 5 pM the inhibitory RNA molecule to the cells. In some embodiments, inhibitory RNA molecules of the disclosure may be capable of inhibiting expression levels of MMP-9 protein in a cell by at least 50% (e.g., at least 55%, 60%, 65%, 70%, 75%, 80%, 85%, 90%, 91%, 92%, 93%, 94%, 95%, 96%, 97%, 98%, 99% or more) in vitro following application of 0.5 pM of the inhibitory RNA molecules to the cells. Suitably, the examples provide assays, which may be used to measure MMP-9 RNA or protein inhibition.

The modulation of the MMP-9 target nucleic acid may be triggered by the hybridization between a contiguous nucleotide sequence of the inhibitory RNA molecule and the MMP-9 target nucleic acid. In some embodiments, the inhibitory RNA molecule of the disclosure includes one or more (e.g., 1, 2, 3, 4, 5, 6, 7, 8, 10, 11, 12, 13, 14, 15, or more) mismatches between the inhibitory RNA molecule and the MMP-9 target nucleic acid. Hybridization to the MMP-9 target nucleic acid may still be sufficient to show a desired modulation of MMP-9 expression even in the absence of the one or more mismatches. Reduced binding affinity resulting from mismatches may advantageously be compensated by increasing number of nucleotides in the inhibitory RNA molecule or increasing the number of modified nucleosides capable of increasing the binding affinity to the target, such as, e.g., 2' sugar-modified nucleosides (e.g., LNA) present within the ASO sequence. In some embodiments, at least one nucleoside modification is a uridine modification or an adenosine modification. In some embodiments, at least one nucleoside modification is selected from N6-methyladenosine (m6A), pseudouridine (ψ), N1-methylpseudouridine (m1ψ), and 5-methoxyuridine (5 moU). In some embodiments, the precursor RNA is modified with methylpseudouridine (m1ψ).

In some embodiments, the inhibitory RNA molecule includes a contiguous sequence of 10 to 30 nucleotides in length, which is at least 90% (e.g., at least 91%, 92%, 93%, 94%, 95%, 96%, 97%, 98%, 99%, or more) complementary to a region of the MMP-9 target nucleic acid. The inhibitory RNA molecule of the disclosure, or contiguous nucleotide sequence thereof, may be fully complementary (i.e., 100% complementary) to a region of the MMP-9 target nucleic acid.

The inhibitory RNA molecule of the disclosure may include or consists of 10 to 35 nucleotides in length (e.g., 10, 11, 12, 13, 14, 15, 16, 17, 18, 19, 20, 21, 22, 23, 24, 25, 26, 27, 28, 29, 30, 31, 32, 33, 34, or 35 nucleotides in length). In some embodiments, the inhibitory RNA molecule includes or consists of 16 to 22 (e.g., 16, 17, 18, 19, 20, 21, or 22) nucleotides in length. In some embodiments, the inhibitory RNA molecule includes or consists of 16 to 20 (e.g., 16, 17, 18, 19, 20) nucleotides in length. In some embodiments, the inhibitory RNA molecule or contiguous nucleotide sequence thereof includes or consists of 22 nucleotides or less (e.g., 22, 21, 20, 19, 18, 17, 16 nucleotides, or less). It is to be understood that any range given herein includes the range endpoints. For example, if an inhibitory RNA molecule is said to include from 10 to 30 nucleotides, both 10 and 30 nucleotides are included. In some embodiments, the contiguous nucleotide sequence includes or consists of 10, 11, 12, 13, 14, 15, 16, 17, 18, 19, 20, 21, 22, 23, 24, 25, 26, 27, 28, 29 or 30 contiguous nucleotides. In some embodiments, the inhibitory RNA molecule includes or consists of 16, 17, 18, 19 or 20 nucleotides.

It is understood that the contiguous nucleobase sequences can be modified to, e.g., increase nuclease resistance or binding affinity to the MMP-9 target nucleic acid. The pattern in which the modified nucleosides (such as high affinity modified nucleosides) are incorporated into the inhibitory RNA molecule sequence is generally termed ASO design. The inhibitory RNA molecules of the disclosure are designed with modified nucleosides and DNA nucleosides. Advantageously, high affinity modified nucleosides can be used.

In some embodiments, the inhibitory RNA molecule includes at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides. In some embodiments, the inhibitory RNA molecule includes from 1 to 10 (e.g., 1, 2, 3, 4, 5, 6, 7, 8, 9, or 10) modified nucleosides.

In some embodiments, the inhibitory RNA molecule includes one or more sugar-modified nucleosides, such as 2' sugar-modified nucleosides. Preferably the inhibitory RNA molecule of the disclosure includes one or more (e.g., 1, 2, 3, 4, 5, 6, 7, 8, 9, 10, 11, 12, 13, 14, 15, or more) 2' sugar-modified nucleoside independently selected from the group consisting of 2'-O-alkyl-RNA (e.g., 2'-O-methyl-RNA), 2'-alkoxy-RNA, 2'-O-methoxyethyl-RNA, 2'-amino- DNA, 2'-fluoro-DNA, arabino nucleic acid (ANA), 2'-fluoro-ANA, and LNA nucleosides. It is advantageous if one or more (e.g., 1, 2, 3, 4, 5, 6, 7, 8, 9, 10, 11, 12, 13, 14, 15, or more) of the modified nucleosides is a locked nucleic acid (LNA).

In some embodiments, the inhibitory RNA molecule of the disclosure includes at least one LNA nucleoside, such as at least 1, 2, 3, 4, 5, 6, 7, or 8 LNA nucleosides, such as from 2 to 6 (e.g., 2, 3, 4, 5, or 6) LNA nucleosides, such as from 3 to 7 (e.g., 3, 4, 5, 6, or 7) LNA nucleosides, 4 to 8 (e.g., 4, 5, 6, 7, or 8) LNA nucleosides or 3, 4, 5, 6, 7 or 8 LNA nucleosides. In some embodiments, at least 75% (e.g., at least 76%, 80%, 85%, 90%, 95%, 96%, 97%, 98%, 99%, or more) of the modified nucleosides in the inhibitory RNA molecule are LNA nucleosides, such as, e.g., beta-D-oxy LNA or ScET. In some embodiments, all the modified nucleosides in the ASO are LNA nucleosides. In some embodiments, the inhibitory RNA molecule may include beta-D-oxy-LNA and one or more (e.g., 1, 2, 3, 4, 5, 6, 7, 8, 9, 10, 11, 12, 13, 14, 15, or more) of the following LNA nucleosides: thio-LNA, amino-LNA, oxy-LNA, ScET, or ENA in either the beta-D or alpha-L configurations or combinations thereof. In some embodiments, all of the LNA cytosine nucleosides are 5-methylcytosine nucleosides. The inhibitory RNA molecule or contiguous nucleotide sequence may have at least 1 LNA nucleoside at the 5' end and at least 2 LNA nucleosides at the 3' end of the nucleotide sequence to impart nuclease resistance to the inhibitory RNA molecule. In some embodiments, an ASO of the disclosure is capable of recruiting RNase H.

In some embodiments, the inhibitory RNA molecule may include one or more (e.g., 1, 2, 3, 4, 5, 6, 7, 8, 9, 10, 11, 12, 13, 14, 15, or more) inverted nucleosides. In some embodiments, the inhibitory RNA molecule may include one or more (e.g., 1, 2, 3, 4, 5, 6, 7, 8, 9, 10, 11, 12, 13, 14, 15, or more) DNA 7-deaza-8-aza-guanine pyrazolo [3,4-d] pyrimidine (PPG) nucleoside.

Within the context of the disclosure, it may be advantageous to employ an inhibitory RNA molecule structural design that is a gapmer design. The gapmer design includes gapmers with uniform flanks, mixed wing flanks, alternating flanks, and gap-breaker designs. It may be advantageous if the inhibitory RNA molecule of the disclosure is a gapmer with an F-G-F' design, a particular gapmer of formula 5'-F-G-F'-3', where regions F and F' independently include 1-8 (e.g., 1, 2, 3, 4, 5, 6, 7, or 8) nucleosides, of which 2-5 (e.g., 2, 3, 4, or 5) are 2' sugar-modified and define the 5' and 3' end of the F and F' region, and G is a region between 6-16 (e.g., 6, 7, 8, 9, 10, 11, 12, 13, 14, 15, or 16) nucleosides which are capable of recruiting RNase H, such as a region including 6-16 (e.g., 6, 7, 8, 9, 10, 11, 12, 13, 14, 15, or 16) DNA nucleosides. In some embodiments, the gapmer is an LNA gapmer. In some embodiments, the LNA gapmer is selected from the following uniform flank designs 4-10-4, 3-11-4, 4-11-4, 4-12-4 or 4-14-2, wherein the generic formula is 5' flank-central block-3' flank. In some embodiments, the LNA gapmer is selected from the following alternating flanks designs 3-1-3-10-2, 1-3-4-6-1-3-2, 1-2-1-2-8-4, or 3-3-1-8-2-1-2.

In some embodiments, the inhibitory RNA molecule of the disclosure has 1, 2, or 3 phosphodiester-linked nucleoside monomers, such as DNA monomers, at the 5' or 3' end of the gapmer region.

The inhibitory RNA molecule may also include at least one (e.g., at least 2, 3, 4, 5, 6, 7, 8, 9, 10, 11, 12, 13, 14, 15, or more) modified internucleoside linkages. In some embodiments, at least 75% (e.g., at least 76%, 80%, 85%, 90%, 95%, 96%, 97%, 98%, 99%, or more) of internucleoside linkages within the contiguous nucleotide sequence are phosphorothioate or boranophosphate internucleoside linkages. In some embodiments, all the internucleotide linkages in the inhibitory RNA molecule or a contiguous sequence thereof are phosphorothioate linkages.

In some embodiments, an inhibitory RNA suitable for use with the disclosed methods comprises a nucleic acid sequence of any one of SEQ ID NOs: 63-80. In some embodiments, an inhibitory RNA suitable for use with the disclosed methods comprises a nucleic acid sequence of SEQ ID NO: 63. In some embodiments, an inhibitory RNA suitable for use with the disclosed methods comprises a nucleic acid sequence of SEQ ID NO: 64. In some embodiments, an inhibitory RNA suitable for use with the disclosed methods comprises a nucleic acid sequence of SEQ ID NO: 65. In some embodiments, an inhibitory RNA suitable for use with the disclosed methods comprises a nucleic acid sequence of SEQ ID NO: 66. In some embodiments, an inhibitory RNA suitable for use with the disclosed methods comprises a nucleic acid sequence of SEQ ID NO: 67. In some embodiments, an inhibitory RNA suitable for use with the disclosed methods comprises a nucleic acid sequence of SEQ ID NO: 68. In some embodiments, an inhibitory RNA suitable for use with the disclosed methods comprises a nucleic acid sequence of SEQ ID NO: 69. In some embodiments, an inhibitory RNA suitable for use with the disclosed methods comprises a nucleic acid sequence of SEQ ID NO: 70. In some embodiments, an inhibitory RNA suitable for use with the disclosed methods comprises a nucleic acid sequence of SEQ ID NO: 71. In some embodiments, an inhibitory RNA suitable for use with the disclosed methods comprises a nucleic acid sequence of SEQ ID NO: 72. In some embodiments, an inhibitory RNA suitable for use with the disclosed methods comprises a nucleic acid sequence of SEQ ID NO: 73. In some embodiments, an inhibitory RNA suitable for use with the disclosed methods comprises a nucleic acid sequence of SEQ ID NO: 74. In some embodiments, an inhibitory RNA suitable for use with the disclosed methods comprises a nucleic acid sequence of SEQ ID NO: 75. In some embodiments, an inhibitory RNA suitable for use with the disclosed methods comprises a nucleic acid sequence of SEQ ID NO: 76. In some embodiments, an inhibitory RNA suitable for use with the disclosed methods comprises a nucleic acid sequence of SEQ ID NO: 77. In some embodiments, an inhibitory RNA suitable for use with the disclosed methods comprises a nucleic acid sequence of SEQ ID NO: 78. In some embodiments, an inhibitory RNA suitable for use with the disclosed methods comprises a nucleic acid sequence of SEQ ID NO: 79. In some embodiments, an inhibitory RNA suitable for use with the disclosed methods comprises a nucleic acid sequence of SEQ ID NO: 80.

In some embodiments, delivery of the inhibitory RNA includes the use of a hydrogel. Delivery vehicles are selected based on lower toxicity and immunogenicity, improved half-life, increased stability, and efficiency.

In some embodiments, inhibitory RNA molecules of the disclosure are encapsulated in a lipid formulation, e.g., a lipid nanoparticle (LNP), or another nucleic acid-lipid particle. LNPs are very useful for systemic applications, as they exhibit extended circulation lifetimes following intravenous injection and accumulate at distal sites (e.g., sites physically separated from the administration site). LNPs include "pSPLP," which include an encapsulated condensing agent-nucleic acid complex. The LNP particles typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles are resistant in aqueous solution to degradation with a nuclease.

The lipid to drug ratio (mass/mass ratio) (e.g., lipid to oligonucleotide ratio) may be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the disclosure.

Non-limiting examples of cationic lipid include N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy) propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoy 1-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino) propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino) ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,55,6α5)-N,N-dimethyl-2,2-di((9Z,12Z)-octadeca-9,12-dienyetetrahydro-3aH-cyclopenta[d][1,3]dioxo1-5-amine (ALN100), (6Z,9Z,28Z,31Z)-heptatriaconta-6,9,28,31-tetraen-19-yl4-(dimethylamino) bu-tanoate (MC3), 1,1'-(2-(4-(2-((2-(bis(2-hydroxydodecyl)amino)ethyl)(2-hydroxydodecyl)amino) ethyl)piperazin-1-yeethylazanediyedidodecan-2-ol (Tech G1), or a mixture thereof. The cationic lipid can include, for example, from about 20 mol % to about 50 mol % or about 40 mol % of the total lipid present in the particle.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-0-monomethyl PE, 16-0-dimethyl PE, 18-1-trans PE, 1-stearoyl-2-oleoyl-phosphatidyethanolamine (SOPE), cholesterol, or a mixture thereof. The non-cationic lipid can be, for example, from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl (Ci2), a PEG-dimyristyloxypropyl (Ci4), a PEG-dipalmityloxypropyl (Cis), or a PEG-distearyloxypropyl (C]a). The conjugated lipid that prevents aggregation of particles can be, for example, from 0 mol % to about 20 mol % or about 2 mol % of the total lipid present in the particle. The nucleic acid-lipid particle may further include cholesterol at, e.g., about 10 mol % to about 60 mol % or about 50 mol % of the total lipid present in the particle.

Recombinant Expression Systems for MMP-9 Knock-Out or Knock-Down

In some embodiments, an MMP-9 inhibitor suitable for use with the disclosed methods down-regulates the activity or level of MMP-9 by genetically ablating the MMP-9 gene from its endogenous locus. In some embodiments, the MMP-9 inhibitor comprises a CRISPR/Cas system for knocking out or knocking down MMP-9 or otherwise reducing MMP-9 expression.

CRISPR/Cas systems are RNA-directed nuclease complexes that have been described to function as an adaptive immune system in microbes. In their natural context, CRISPR/Cas systems occur in CRISPR (clustered regularly interspaced short palindromic repeats) operons or loci, which generally comprise two parts: (i) an array of short repetitive sequences (30-40 bp) separated by equally short spacer sequences, which encode the RNA-based targeting element; and (ii) ORFs encoding the Cas encoding the nuclease polypeptide directed by the RNA-based targeting element alongside accessory proteins/enzymes. Efficient nuclease targeting of a particular target nucleic acid sequence generally requires both (i) complementary hybridization between the first 6-8 nucleic acids of the target (the target seed) and the RNA guide; and (ii) the presence of a protospacer-adjacent motif (PAM) sequence within a defined vicinity of the target seed (the PAM usually being a sequence not commonly represented within the host genome).

In some embodiments, the CRISPR-Cas system is CRISPR/Cas9. In some embodiments, the CRISPR-Cas system is CRISPR/Cas12. In some embodiments, the CRISPR-Cas system is CRISPR/Cas system comprising an inactive nuclease domain and an effector domain (e.g., KRAB domain) capable of transcriptionally repressing expression of MMP-9. In some embodiments, the CRISPR-Cas system comprises a guide RNA capable of binding to an MMP-9 gene or MMP-9 transcript (e.g., pre-mRNA or mRNA). In certain embodiments, the CRISPR-Cas system comprises a Cas9 protein and a guide RNA, a single guide RNA, or at least one nucleic acid molecule that targets the Cas protein to a nucleic acid encoding MMP-9.

MMP-9 Biology

MMP-9 is involved in many developmental processes, including ECM degradation, angiogenesis and formation of endochondral bone (for which it appears to play a unique role in the MMP family). Substrates of MMP-9 include matrix proteins, growth factors and cytokines, and in addition to extracellular matrix remodeling, MMP-9 can render growth factors bioavailable (e.g. VEGF, from heparin sulfate proteoglycans) or potentiate the activity of cytokines by cleavage. Neutrophils, macrophages, fibroblasts, and endothelial cells are among the cell types that secrete MMP-9. (Vandooren J., Van den Steen P. E., Opdenakker G.

Biochemistry and molecular biology of gelatinase B or matrix metalloproteinase-9 (MMP-9): The next decade. Crit. Rev. Biochem. Mol. Biol. 2013; 48:222-272. doi: 10.3109/10409238.2013.770819). Secreted MMP-9 exists in a pro-form, which requires other proteases to cleave it, thereby converting it into the active form. (Huang, H., Sensors (Basel). 2018 October; 18 (10): 3249). MMP-9 latency is maintained by the interaction of one cysteine (Cys99) residue in the propeptide of pro-MMP-9 with the catalytic zinc ion of MMP-9. (Huang, H., Sensors (Basel). 2018 October; 18 (10): 3249). When this interaction is disrupted by proteolytic cleavage, reactive oxygen species, or nitric oxide, MMP-9 is activated. (Huang, H., Sensors (Basel). 2018 October; 18 (10): 3249). In some embodiments, the methods of the invention provide one or more MMP-9 inhibitors, which can prevent activation of MMP-9 from its pro-form and/or directly inhibit MMP-9 activity via a non-substrate competitive, allosteric mechanism.

Non-genetic heterotopic ossification in mice involves MMP-9, for which a variety of roles in initiation of HO, in the context of inflammatory injury and aberrant wound repair, have been described. For example, MMP-9 has been described as critical in the opening of the blood-nerve barrier in mouse peripheral nerves. Rodenberg E, et al. Matrix metalloproteinase-9 is a diagnostic marker of heterotopic ossification in a murine model. Tissue Eng Part A 17:2487-2496 (2011). Opening the blood-nerve barrier allows osteoblast progenitors to enter into endoneurial vessels and exit the nerve through the circulation. Salisbury E, et al. Sensory nerve induced inflammation contributes to heterotopic ossification. J Cell Biochem 112:2748-2758 (2011); Lazard Z W, et al. Osteoblasts have a neural origin in heterotopic ossification. Clin Orthop Relat Res 473:2790-2806 (2015). MMP-9 may mediate opening of the endoneurial vessels through binding and regulation of claudin 1. Hackel D, et al. Transient opening of the perineurial barrier for analgesic drug delivery. Proc Natl Acad Sci USA 109: E2018-E2027 (2012).

MMP-9 activity is elevated in mice within 24 hours following the induction of heterotopic ossification in injury-based or BMP-signaling based models of non-genetic heterotopic ossification. Davis E L, et al. Location-dependent heterotopic ossification in the rat model: The role of activated matrix metalloproteinase 9. J Orthop Res. 34 (11): 1894-1904 (2016). Treatment of heterotopic ossification in mice with the MMP-9 inhibitor minocycline results in reduced bone formation compared to mice treated with the vehicle. Minocycline treatment may reduce heterotopic ossification in mice by inhibiting activation of MMP-9 and MMP-9 activity. The activated form of MMP-9 was absent from minocycline treated mice., which had a percentage of cells expressing active MMP-9/total MMP-9 of 4.1%±0.56 S.E.M. compared to 95.5%±1.75 S.E.M for vehicle treated mice. Davis E L, et al. Location-dependent heterotopic ossification in the rat model: The role of activated matrix metalloproteinase 9. J Orthop Res. 34 (11): 1894-1904 (2016). In a rat model of traumatic brain injury, MMP-9 was identified as predictive a biomarker for HO formation (Shi et al Mol. Med. Rep 2017). In physiologically-relevant rat model of combat-related HO, MMP-9 was among a subset of factors found to be associated with HO formation, with strong and sustained expression at the site of new bone formation (Qureshi et. al. Clin Orthop Relat Res (2015).

Elevated MMP-9 expression has been reported in non-genetic heterotopic ossification in humans as well. Tissues from patients undergoing active bone formation show positive staining for both active MMP-9 and total MMP-9 protein in the nascent HO lesion, with the majority of the protein being activated. Davis E L, et al. Location-dependent heterotopic ossification in the rat model: The role of activated matrix metalloproteinase 9. J Orthop Res. 34 (11): 1894-1904 (2016). Analysis of highly penetrant war-wounds in veterans identified elevated MMP-9, among 13 other factors including BMP2, as associated with injuries that progress to HO as compared to those that do not. Evans et al Clin Orthop Relat Res (2014).

NHHO Diagnosis

Acquired heterotopic ossification can occur with essentially any musculoskeletal trauma, spinal cord injury, central nervous system injury, head injury, cerebrovascular accident, sickle cell anemia, hemophilia, tetanus, poliomyelitis, multiple sclerosis, toxic epidermal necrolysis and burns. Heterotopic ossification occurs most commonly after joint arthroplasty, spinal cord injury, traumatic brain injury, blast trauma, elbow and acetabular fractures, and thermal injury (Ranganathan K, et al., (2015). J Bone Joint Surg Am, 97 (17)). Examples of musculoskeletal trauma include, but are not limited to, hip, knee, shoulder, or elbow arthroplasty; fractures; joint dislocations; or soft-tissue trauma, with the musculus quadriceps femoris and *Musculus brachialis*. Acquired heterotopic ossification can also be associated with fever, swelling, and erythema (e.g., local, patchy reddening of the skin). In one embodiment, neurogenic heterotopic ossification is not associated with local trauma.

A triple bone scan or a three-phase bone scan is used diagnostic procedure that includes a series of images that can show early inflammation, bone disease, infection, or fractures. These conditions can be imaged with the scan before they can be seen on standard X-rays in many cases. This scan uses a small amount of radioactive material as a tracer that is absorbed into the bones and detected by a camera to result in an image.

As disclosed in WO2016130897, NHHO typically occurs between about 1 week and 12 weeks following an injury. Heterotopic ossification can be reliably diagnosed by computed tomography, bone scintigraphy and ultrasonography. Two to six weeks later, the abnormal bone formation has progressed to the point that it is detectable by radiography. Bony maturation typically occurs within six months. Conventional treatment usually involves non-steroidal anti-inflammatory drugs (indomethecin, rofecoxib), or bisphosphonate (etidronate, pamidronate), Coumadin/warfarin, salicylates, and/or local radiation can also be administered. Often, surgery is the only option for treatment.

In some embodiments, the MMP-9 inhibitor is an anti-MMP-9 antibody and is administered via subcutaneous administration at a dose of about 50 mg, about 100 mg, about 150 mg, about 200 mg, about 250 mg, about 300 mg, or about 400 mg.

In further embodiments, disclosed is a dosage regimen comprising administration of about 50 mg, about 100 mg, about 150 mg, about 200 mg, about 250 mg, about 300 mg, or about 400 mg every 1, 2, 3, or 4 days.

In preferred embodiments, the subject is of age greater than about 12 years and an MMP-9 inhibitor (such as andecaliximab) dose of 150 mg is administered every week. In another preferred embodiment, the subject is of age greater than about 12 years and an MMP-9 inhibitor dose of 50 mg is administered every week. In another preferred embodiment, the subject is aged between about 6 to about 11 years and an MMP-9 inhibitor dose of 75 mg is administered every week. In another preferred embodiment, the subject is aged between about 6 to about 11 years and an MMP-9 inhibitor dose of 25 mg is administered every week. In another preferred embodiment, the subject is aged between 2 and about 5 years and an MMP-9 inhibitor dose of 45 or 50 mg is administered every week. In another preferred embodiment, the subject is aged between 2 and about 5 years and an MMP-9 inhibitor dose of 15 mg is administered every week.

In preferred embodiments, the subject is aged 6-11 years and an MMP-9 inhibitor (such as andecaliximab) dose of 75 mg is administered every week. In some embodiments, the subject is aged 6-11 years and a dose of 25 mg is administered every week. In some embodiments, the subject is aged 2-5 years and a dose of 50 or 45 mg is administered every other week. In some embodiments, the subject is aged 2-5 years and a dose of 15 mg is administered every other week. In some embodiments, the subject is aged 6-11 years and a dose of 75 mg is administered every other week. In some embodiments, the subject is aged 2-5 years and a dose of 45 or 50 mg is administered every other week.

In some embodiments, the subject is a human. In some embodiments, the subject is under about thirty years of age. In some embodiments, the subject is aged 12 or above. In some embodiments, the subject is aged 18 or above. In some embodiments, the subject is aged 6-12. In some embodiments, the subject is aged 2-12.

In some embodiments, the occurrence of NHHO or a symptom of NHHO is identified with a triple bone scan within 2 days of the of the NHHO-inductive event.

In some embodiments, the occurrence of NHHO or a symptom of NHHO is identified with a triple bone scan within 3 days of the of the NHHO-inductive event.

In some embodiments, the occurrence of NHHO or a symptom of NHHO is identified with a triple bone scan within 4 days of the of the NHHO-inductive event.

In some embodiments, the occurrence of NHHO or a symptom of NHHO is identified with a triple bone scan within 5 days of the of the NHHO-inductive event.

In some embodiments, the occurrence of NHHO or a symptom of NHHO is identified with a triple bone scan within 6 days of the of the NHHO-inductive event.

In some embodiments, the occurrence of NHHO or a symptom of NHHO is identified with a triple bone scan within 7 days of the of the NHHO-inductive event.

In some embodiments, the occurrence of NHHO or a symptom of NHHO is identified with a triple bone scan within 8 days of the of the NHHO-inductive event.

In some embodiments, the occurrence of NHHO or a symptom of NHHO is identified with a triple bone scan within 9 days of the of the NHHO-inductive event.

In some embodiments, the occurrence of NHHO or a symptom of NHHO is identified with a triple bone scan within 10 days of the of the NHHO-inductive event.

In some embodiments, the occurrence of NHHO or a symptom of NHHO is identified with a triple bone scan within 11 days of the of the NHHO-inductive event.

In some embodiments, the occurrence of NHHO or a symptom of NHHO is identified with a triple bone scan within 12 days of the of the NHHO-inductive event.

In some embodiments, the occurrence of NHHO or a symptom of NHHO is identified with a triple bone scan within 13 days of the of the NHHO-inductive event.

In some embodiments, the occurrence of NHHO or a symptom of NHHO is identified with a triple bone scan within 2 weeks of the of the NHHO-inductive event.

In some embodiments, the occurrence of NHHO or a symptom of NHHO is identified with a triple bone scan within 3 weeks of the of the NHHO-inductive event.

In some embodiments, the occurrence of NHHO or a symptom of NHHO is identified with a triple bone scan within 1 month of the of the NHHO-inductive event.

In some embodiments, the occurrence of NHHO or a symptom of NHHO is identified with a triple bone scan within 2 months of the of the NHHO-inductive event.

In additional embodiments, disclosed is a pharmaceutical composition comprising a dose of 75 mg is administered every week, a dose of 25 mg administered every week, a dose of 50 or 45 mg administered every other week, a dose of 15 mg administered every other week, a dose of 75 mg administered every other week, or a dose of 45 or 50 mg administered every other week of an MMP-9 inhibitor suitable for intravenous administration to a human subject having a spinal cord injury, trauma, brain injuries, burns, fractures, muscle contusion, joint arthroplasty/replacement, hip surgery/replacement, acetabular surgery/replacement, elbow fracture, fracture of the long bones of the lower leg, combat-related trauma, amputation, neuromuscular blockade used to manage adult respiratory distress syndrome, or a nontraumatic myelopathy.

In further embodiments, disclosed is a method of preventing or reducing the severity and/or duration of a condition associated with a nonhereditary heterotopic ossification (NHHO) comprising administering to a human subject an effective amount of an inhibitor of MMP-9 activation or activity.

The efficacy of a given treatment for a disorder comprising abnormal bone growth as described herein can be determined by the skilled clinician. However, a treatment is considered "effective treatment," as the term is used herein, if any one or all of the signs or symptoms of the disease or disorder is/are altered in a beneficial manner (e.g., reduced ossification, regression of abnormal bone growths, reduced pain, increased range of motion etc.), other clinically accepted symptoms or markers of disease are improved, or even ameliorated, e.g., by at least 10% following treatment with an agent. Efficacy can also be measured by the failure of an individual to worsen as assessed by stabilization of the disease or disorder, hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of abnormal bone growth; or (2) relieving the disease, e.g., causing regression of symptoms; and (3) preventing or reducing the likelihood of the development of a disease (e.g., ossification following trauma).

Kits

In various aspects, the invention provides kits comprising one or more components that comprise, but are not limited to, MMP-9 inhibitors such as antibodies or antigen-binding fragments, small molecules, peptides, nucleic acids, as disclosed herein, one or more pharmaceutically acceptable carrier and/or a therapeutic agent. In some embodiments, the MMP-9 inhibitors such as antibodies or antigen-binding fragments, small molecules, peptides, nucleic acids and/or the therapeutic agent can be formulated as a substantially pure composition or in combination with a pharmaceutically acceptable carrier, in a pharmaceutical composition.

In alternative aspects, the MMP-9 inhibitors such as antibodies or antigen-binding fragments, small molecules, peptides, nucleic acids are provided as components of a diagnostic or theranostic kit.

In various aspects, the kit includes MMP-9 inhibitors such as antibodies or antigen-binding fragments, small molecules, peptides, nucleic acids thereof of the invention or a pharmaceutical composition thereof in one container (e.g., in a sterile glass or plastic vial) and a pharmaceutical composition thereof and/or a therapeutic agent in another container (e.g., in a sterile glass or plastic vial).

In some embodiments, the kit comprises a combination of the invention, including MMP-9 inhibitors such as antibodies or antigen-binding fragments, small molecules, peptides, nucleic acids thereof of the invention with a pharmaceutically acceptable carrier, optionally in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices known in the art.

Optional components of the kit includes a package insert including information concerning the pharmaceutical compositions and dosage forms of MMP-9 inhibitors such as antibodies or antigen-binding fragments, small molecules, peptides, nucleic acids in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

MMP-9 inhibitors such as antibodies or antigen-binding fragments, small molecules, peptides, nucleic acids thereof of the invention can be packaged as reagents in predetermined amounts with instructions for performing the diagnostic or detection assay. In some embodiments, where the antibody or fragment is labeled with an enzyme, the kit will include substrates and cofactors required by the enzyme (e.g., a substrate precursor which provides the detectable chromophore or fluorophore). Other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Depending on the desired use, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support or may be applied to the surface of a solid support when the kit is used. In some embodiments of the invention, the signal generating means may come pre-associated with an antibody or fragment of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In particular aspects, an enzyme that catalyzes the formation of a chemiluminescent or chromogenic product or the reduction of a chemilluminescent or chromogenic substrate is a component of the signal generating means. Such enzymes are well known in the art. Kits may comprise any of the capture agents and detection reagents described herein. The kit can also include instructions for carrying out the methods of the invention.

In certain preferred aspects, the kit comprises one or more labels describing the contents of the container and providing indications and/or instructions regarding use of the contents of the container to treat one or more MMP-9 associated disorders as described herein using MMP-9 inhibitors such as antibodies or antigen-binding fragments, small molecules, peptides, nucleic acids thereof of the invention.

In one aspect, the kit comprises treatment for MMP-9 related disorders including genetic heterotopic ossification (gHO), such as fibrodysplasia ossificans progressive (FOP) by administering one or more MMP-9 inhibitors such as antibodies or antigen-binding fragments, small molecules, peptides, nucleic acids thereof of the invention. The kit may optionally further include a syringe for parenteral, e.g., intravenous, administration. Preferably, the kit comprises anti-MMP-9 antibody or antigen-binding fragment thereof and a label attached to or packaged with the container describing use of the antibody or fragment. In yet another aspect, the kit comprises a prophylactic agent or further therapeutic agent and a label attached to or packaged with the container describing use of the prophylactic agent or further therapeutic agent with the anti-MMP-9 antibody or fragment. In some embodiments, an anti-MMP-9 antibody and prophylactic agent or further therapeutic agent are in separate vials or are combined together in the same pharmaceutical composition.

As discussed above in the combination therapy section, concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The therapeutic and detection kits disclosed herein may also be prepared with one or more MMP-9 inhibitors such as antibodies or antigen-binding fragments, small molecules, peptides, nucleic acids disclosed herein and instructions for using the composition as a detection reagent or therapeutic agent. Containers for use in such kits may typically comprise at least one vial, test tube, flask, bottle, syringe or other suitable container, into which one or more of the detection and/or therapeutic composition(s) may be placed, and preferably suitably aliquoted. Where a second therapeutic agent is also provided, the kit may also contain a second distinct container into which this second detection and/or therapeutic composition may be placed. Alternatively, a plurality of compounds may be prepared in a single pharmaceutical composition, and may be packaged in a single container means, such as a vial, flask, syringe, bottle, or other suitable single container. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorogenic, or other type of detectable label or detecting means is included within the kit, the labeling agent may be provided either in the same container as the detection or therapeutic composition itself or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery. A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces. In further embodiments, also provided is a processor, a computer readable memory, and a routine stored on the computer readable memory and adapted to be executed on the processor to perform any of the methods described herein. Examples of suitable computing systems, environments, and/or configurations include personal computers, server computers, handheld or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

EQUIVALENTS

It will be readily apparent to those skilled in the art that other suitable modifications and adaptions of the methods of the invention described herein are obvious and may be made using suitable equivalents without departing from the scope of the disclosure or the embodiments. Having now described certain compounds and methods in detail, the same will be more clearly understood by reference to the following examples, which are introduced for illustration only and not intended to be limiting.

EXAMPLES

The present invention is further described by the following examples, which are not intended to be limiting in any way.

Example 1: In Vitro Assay for Inhibiting Activity of MMP-9 of an Anti-MMP-9 Antibody To determine if the antibody can efficiently block catalytic activity of murine or human MMP-9, the ability of MMP-9 to cleave the (7-methoxycoumarin-4-yl) acetyl-Pro-Leu-Gly-Leu-(3-[2,4-dinitrophenyl]-L-2,3-diaminopropionyl)-Ala-Arg-NH$_2$ fluorescent substrate (R&D Systems, ES001) at the presence of different concentrations of antibody are measured. Catalytic domains of human or murine MMP-9 protease are purchased in Enzo Life Sciences (Cat #BML-SE360-0010) and Anaspec (Cat #AS-55884-10), correspondently.

In mice, the anti-MMP-9 antibody administered is AB0046. In humans, the anti-MMP-9 antibody administered is andecaliximab (AB0045). The activity assay with catalytic domains of MMP-9 (10 nM) is performed in 0.2 ml of 50 mM Hepes buffer, pH 7.5 containing 100 mM NaCl, 10 mM CaCh. 10 mM ZnCh, 0.5 mM MgCh and 0.005% Brij 35 at 37° C. The concentration of Mca-PLGL-Dpa-AR-NH2 fluorescent substrate is 10 mM. To determine the IC50 value of the inhibitory antibody, MMP-9 is pre-incubated for 30 min at 20° C. with increasing concentrations of the antibody (0-1,000 nM). The steady state rate of substrate hydrolysis is continuously monitored at $1_{ec}$ (excitation wavelength) of 320 nm and $1_{eih}$ (emission wavelength) of 400 nm by using Varioskan Lux fluorescence spectrophotometer (Thermo Scientific). All assays are performed in triplicate in wells of a 96 well plate. IC50 values are calculated by determining the concentrations of antibody needed to inhibit 50% of the MMP-9 activity against peptidic substrate. GraphPad Prism is used as fitting software.

Example 2: Mouse Model of Fibrodysplasia Ossificans Progressiva

As described in Hatsell et al (Science Translational Medicine 2015), a knock-in transgenic model (Acvr1[R206H] FIEx/+; Gt(ROSA26)SorCreERT2/+) is used for these studies.

All animal studies are conducted under an IACUC approved protocol in accordance with OLAW. All animals are housed in ALAACA accredited vivarium under standard conditions as described by OLAW. Animals are randomly selected based on age and health. Experimental groups are selected randomly, and animals coded to avoid bias. Group sizes are based on historical data; however, power analysis is repeated after data collection to ensure appropriate group sizes.

Example 3: In Vivo Evaluation of Anti-MMP-9 Antibody in Mice

A conditional-on knock-in mouse model ACVR1R206H/FIEx was used to generate tamoxifen-inducible global R206H mutant allele expression after recombination by Cre recombinase. The ACVR1R206H/+; CreERT2−/+ FOP mouse model (FOP mice) has been shown to form heterotopic bone following transgene activation by tamoxifen injections and local muscle injury with cardiotoxin.

Tamoxifen was dissolved in corn oil at a concentration of 15 mg/ml by shaking overnight at 21±3° C. Tamoxifen is light-sensitive and was made and stored in a light-blocking vessel (amber). The next day, the mixture was incubated in a water bath set to maintained at 37° C. and stirred until complete dissolution of Tamoxifen. Daily aliquots of Tamoxifen solution were prepared and stored at 4° C. The stock solution was stable for several weeks and was discarded at the end of the study. The day of dosing, the aliquot was dispensed at room temperature.

Cardiotoxin stock solution was prepared by dissolution in phosphate buffered saline at a concentration of 10 μM. An aliquot can be stored in a freezer set to maintain −20° C. and thawed on the day of dosing.

8-12 week old Acvr1$^{cR206H/+}$ mice (Acvr1[R206H] FIEx/+; Gt(ROSA26)SorCreERT2/+) were injected with tamoxifen by intraperitoneal (IP) route to induce transgene activation and mutant gene expression globally. The induction of disease occurred via tamoxifen (75 mg/kg×7 days, IP) and cardiotoxin injection on day 0 (10 µM, 100 µL) in the right gastrocnemius muscle. Dosing occurred at 30 mg/kg three days prior to injury (loading dose to address initial target-mediated drug disposition), then 15 mg/kg on days 0 and 3, which is a similar regimen as Lounev et al., 2024, or 15 mg/kg continuing twice per week after day 3, via IP route.

Faxitron images (medio-lateral view) of the collected entire right and left hindlimbs from all animals were performed (ex vivo) to document the presence of ectopic bone. Images were assessed qualitatively.

The effect of the anti-MMP-9 antibody, AB0046, on bone formation in the mouse model was evaluated ex vivo at the end of the in-life period. Analysis of HO formation was performed at 14-24 days post-injury. Quantitation of heterotopic ossification at the injury site was assessed in all animals using a high-resolution micro-CT system (Scanco Medical AG micro-CT 100) and analyzed using the 3-D morphometry, in order to determine the volume of heterotopic bone.

The quantity of HO is reported for each treatment group in FIG. 1. In IgG control-treated mice, the amount of HO was shown to be significantly greater than in anti-MMP-9 antibody-treated mice, yielding consistent findings to that reported Lounev et al., 2024. These results show that anti-MMP-9 antibody treatment reduced HO in mice.

Example 4: Inhibition of MMP-9 as a Potential Treatment Strategy for FOP Using the Anti-MMP-9 Antibody Andecaliximab A pooled analysis was conducted of all safety data from prior randomized, double-blind, placebo-controlled clinical trials where andecaliximab was administered subcutaneously as a monotherapy in non-oncologic conditions.

The pooled safety analysis consisted of 347 patients enrolled in double-blind (DB) placebo-controlled trials [age 18-78 yrs, median duration of treatment: DB=8 wk; DB+ open label extension (OLE)=17 wk; max 75 wk]. During the DB treatment period, treatment-emergent adverse event (TEAE) assessed as related to study drug occurred in 19 (17.8%) receiving 150 mg Q2W, 23 (20.2%) receiving 150 mg QW, 13 (22.4%) receiving 300 mg QW, none of those receiving 600 mg andecaliximab QW, and 20 participants (22.0%) received a placebo. Treatment-related TEAEs more common with andecaliximab compared with placebo (difference of >1 percentage point) were injection site erythema (2.1% versus 1.1%), headache (1.4% versus 0%), anemia (1.1% versus 0%), and injection site pain (1.1% versus 0%).

MMP-9 inhibition represents a novel strategy to block HO formation in FOP. Preclinical toxicology studies and prior safety experience (including with SC doses higher than planned in ANDECAL) support the initiation of a phase 2/3 study of andecaliximab in patients with FOP age 2 yr and older. Enrollment in ANDECAL study will initiate later this year.

Example 5: In Vivo Evaluation of Anti-MMP-9 Antibody for NHHO

Initial treatment with a loading dose of anti-MMP9 antibody (e.g. 30 mg/kg AB0046) is made prior to HO induction to address the existing pool of MMP-9 and promote generation of more predictable pharmacokinetic properties thereafter. Following induction of HO, mice are dosed twice a week with 15 mg/kg AB0046 (or control IgG) for 9-12 weeks. The effect of anti-MMP-9 antibody on bone formation in the mouse model is evaluated using whole-mount skeletal preparation. At end of treatment, the degree of HO formation is quantified using longitudinal micro CT (computed tomography) scans focused on the hind limbs at the site of injury. After the mice are euthanized by $CO_2$ inhalation, soft tissues encompassing the site of new bone formation were isolated from the rear hind limb and flash frozen to enable additional histopathological analysis.

In micro CT analysis, scans are taken 9 weeks post-injury using 80 peak kilovoltage (kVp), 80 mA, and 1,100-ms exposure. Images are reconstructed, and HO volume formation is analyzed using a calibrated imaging protocol. Calculation of cortical thickness is performed in MicroView. Briefly, the fusepoint of the tibia and fibula in the uninjured right leg is selected as a reference landmark. A region encompassing only the proximal tibia is defined as the region of interest. The mean cortical thickness of the given region is then determined automatically with a 1,800-Hounsfield unit threshold cutoff.

The quantity of HO is reported for each treatment group. In IgG control-treated mice, it is anticipated that animals show HO in the injured limb. In IgG control treated mice, the amount of HO is expected to be significantly greater than in anti-MMP-9 antibody treated mice. Results show that anti-MMP-9 antibody treatment reduces HO in mice.

Example 6: Mouse Model for NHHO Formation

To evaluate the effect of matrix metalloproteinase 9 (MMP9) gene knockdown, mice are burned and induced with tenotomy to form non-hereditary heterotopic ossification. Male mice are housed in a group of 4 animals in a cage with clean bedding before surgery, and are individually housed post-surgery. The three mice strains include B6.FVB (Cg)-Mmp9tm1Tvu/J as strain 1, B6FVBF1/J (wild type) as strain 2, and C57BL/6J as strain 3, as seen in Table 1. Each cage is clearly labeled with a color-coded cage card indicating study, group, and animal numbers. Animals are maintained and monitored for good health in accordance with test facility SOPs, and at the discretion of the laboratory animal veterinarian. Food and water are provided ad libitum for the mice in this study. Environmental controls for the animal room will be set to maintain a temperature of 22±3° C., humidity of 30-70% RH, and a 12-hour light/12-hour dark cycle.

This protocol involves creating a 30% total body surface area partial thickness contact burn on the dorsal skin, as well as division of the Achilles tendon at its midpoint, as described in the Peterson literature (Peterson J R, et al, (2015). J. Vis. Exp., (102): e52880). Relying solely on a traumatic injury to induce HO at a predictable location provides an isolated time-course study of endochondral heterotopic bone formation from intrinsic physiologic processes and environment only.

To induce heterotopic ossification, burn injury and tenotomy is performed on day 0. Animals are anesthetized using inhalation anesthesia. Buprenorphine at 0.1 mg/kg is administered subcutaneously before surgery initiation. The mouse dorsum (2 cm×3 cm) and left hind paw (from heel to the knee) are shaved. Achilles tenotomy is performed on the left Achilles tendon.

A longitudinal incision is made along the medial aspect of the left Achilles tendon. The incision is extended so the Achilles tendon can be easily visualized; approximately 0.5 cm. Achilles tenotomy is performed with sharp dissection of the tendon at the midpoint with sharp tissue scissors. One blade of the tissue scissor is inserted in the tissue plane beneath the tendon and dissected along the plane until the blade is at the tendon midpoint. The scissor blades are closed to sever the tendon sharply.

Following the tenotomy surgery, a dorsal partial thickness burn injury is performed with an aluminum block weighing 35 g and measurements of approximately 2 cm×2 cm×3 cm which are heated to 60° C. on water bath. To produce partial thickness burn injury, hot aluminum block is kept on shaved skin for 17 seconds. After drying, a Tegaderm dressing is applied on the burn injury to avoid any infection. After surgery, buprenorphine is administered every five hours for the next five days for pain management.

Figure 3:
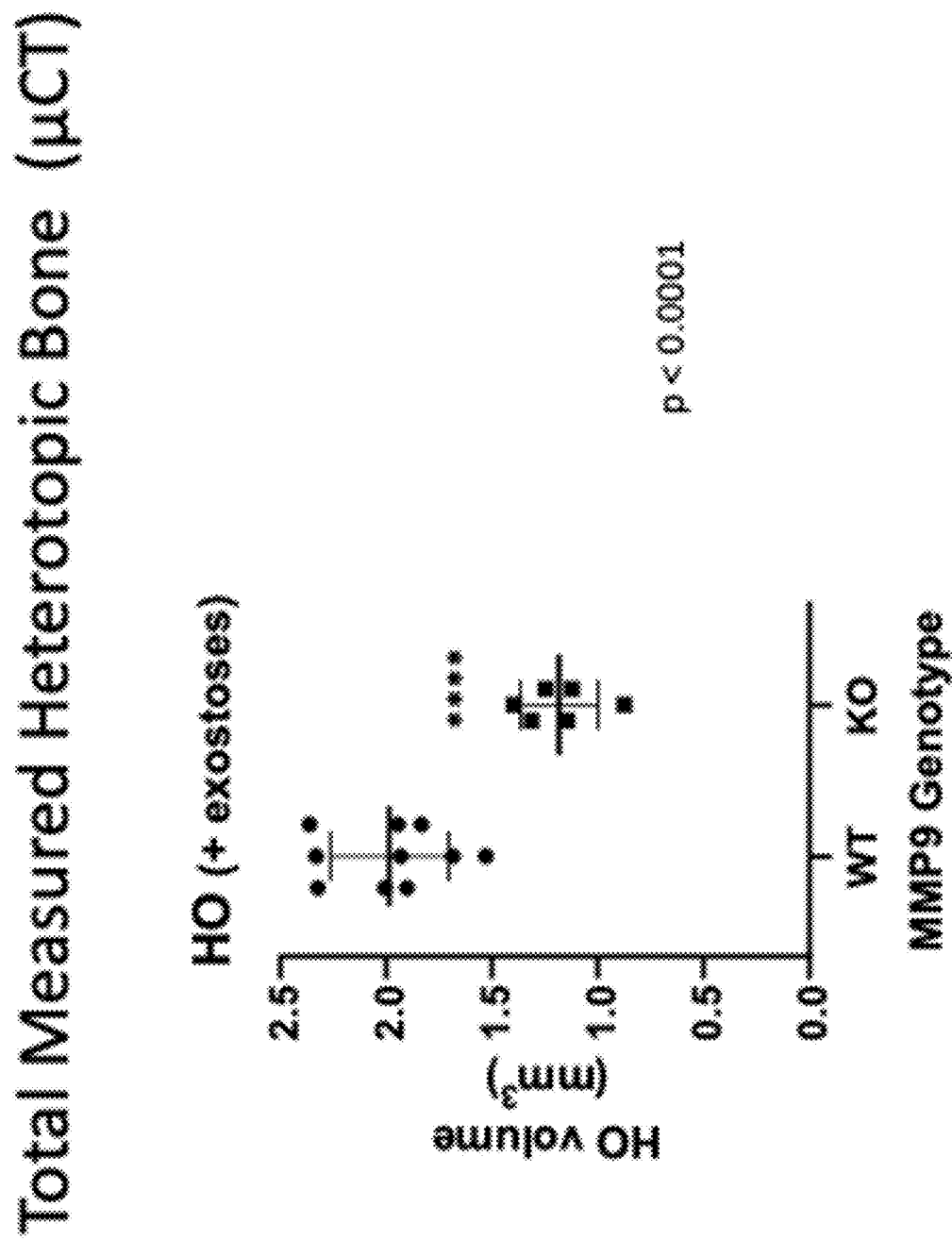
FIG. 3 shows the total measured heterotopic bone (in µCT) present in both the WT and KO MMP-9 mice. HO is measured in soft tissue and exostoses attached to calcaneum, and depicts that HO was significantly reduced in MMP-9 KO mice compared to wild-type littermate controls.

Body weight is measured once on pre-study and then followed by twice a week. Detailed clinical observation occurs every two-weeks pre-study and then weekly. Animals are observed for cage-side observation daily from day 1 and mortality/morbidity are checked twice daily. On the terminal day 62, gross examination is performed. A tail snip is individually collected from all study animals, and using PCR techniques, the snips are placed into polypropylene tubes and frozen immediately over dry ice. Samples are stored in a freezer set to maintain −80° C. for future analysis. Hind limbs are collected, skin removed, pinned on paraffin blocks, fixed in 10% neutral buffered formalin for 48 hours and then transferred to 70% ethanol. Samples are shipped in ethanol. After the completion of the experiments, animals are euthanized as per SOP-BIO-IPH-126-03 and are disposed as per SOP-BIO-AH-117-04. See FIG. 3 for the HO quantification of soft tissue for both WT and MMP-9 KO mice.

Example 7: NHHO Mice Imaging Protocol for μCT Acquisition and Analysis

To image the results of the mouse model for NHHO formation, the anesthetized mouse is secured on the scanner bed in the prone position, and the hind limbs are taped securely to the bed to prevent breathing motion artifact. The air, water, and hydroxyapatite containing phantom is included beneath the mouse for image calibration. The Bone Analysis software is opened and a region of interest (ROI) is defined to encompass both hind limbs from the hip joint proximally to the tip of the hind paw distally. The image is obtained with 80 kV, 500 MA and 1,300 msec exposure, 48 μm voxel size parameters.

Figure 2:
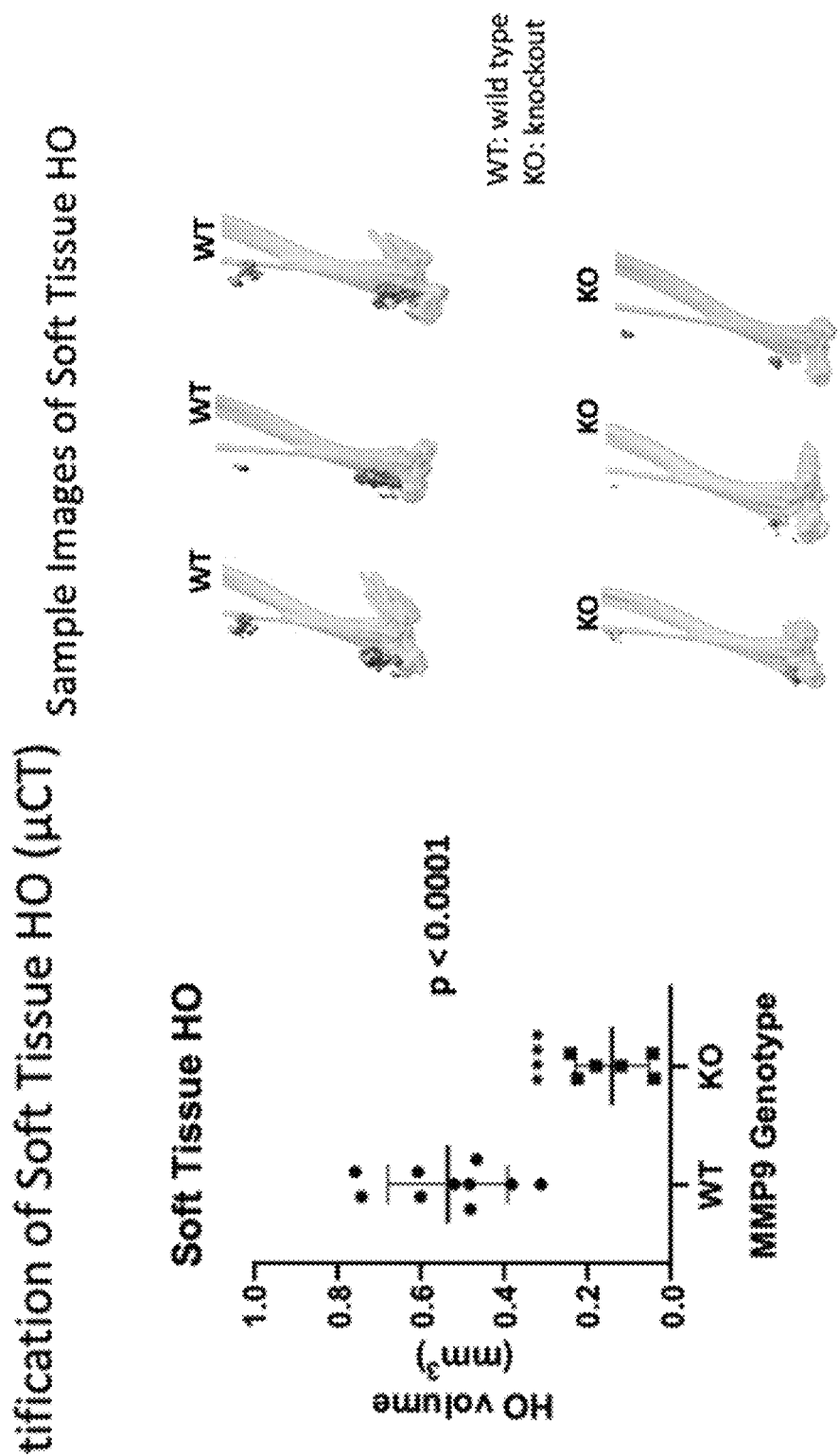
FIG. 2 shows the quantification of soft tissue HO (in µCT) present in both the WT and MMP-9 KO mice, and a sample image of soft tissue HO in both WT and KO mice. This figure demonstrates significant inhibition of NHHO demonstrated with an MMP-9 blockade, as HO originating in soft tissue was significantly reduced in MMP-9 KO mice compared to wild-type littermate controls

The image is then calibrated to Hounsfield units (HU) by drawing a ROI in each of the three phantom chambers and inputting the average density into the appropriate fields in the software. Using the "grabber" tool in the software, the image is re-oriented so the tibia of the left hind limb is parallel along the Z axis to allow the clearest anatomical view for the delineation of orthotopic cortical bone structures and HO formation. Beginning at the knee, scroll distally through the image slices until HO is encountered. Using the manual spline tool, an ROI is made around the ectopic bone on every 5 slice continuing distally through the paw or until HO has been surpassed. Using the extrapolate tool, extend and stitch the ROIs together into one ROI that contains all the HO. A 3D ROI is made, and the bone volume is calculated by setting the lower and upper threshold values that best show the bone window. The same fixed threshold values are used for all scans. See FIG. 2 for the total HO-formed plot.

NUMBERED EMBODIMENTS

Embodiments disclosed herein include embodiments A1 to A78, as follows:

Embodiment A1. A method of treating a subject having a non-hereditary heterotopic ossification disorder, administering to the subject an effective amount of an MMP-9 inhibitor.

Embodiment A2. The method of Embodiment A1, wherein the MMP-9 inhibitor is selected from the group consisting of: an anti-MMP-9 antibody or antigen-binding fragment thereof, an inhibitory RNA, an inhibitory polypeptide, a small molecule inhibitor, and a CRISPR-Cas system.

Embodiment A3. The method of Embodiment A2, wherein the MMP-9 inhibitor is an anti-MMP-9 antibody or antigen-binding fragment thereof.

Embodiment A4. The method of Embodiment A3, wherein the anti-MMP-9 antibody or antigen-binding fragment thereof binds to: (i) an MMP-9 pro-form and inhibits activation of the pro-form; and/or (ii) an MMP-9 active form and inhibits activity of the active form.

Embodiment A5. The method of Embodiment A4, wherein the anti-MMP-9 antibody or antigen-binding fragment thereof binds to the MMP-9 pro-form.

Embodiment A6. The method of Embodiment A4, wherein the anti-MMP-9 antibody or antigen-binding fragment thereof binds to the active form of MMP-9.

Embodiment A7. The method of any one of Embodiments A3 to A6, wherein the anti-MMP-9 antibody or antigen-binding fragment thereof comprises a heavy chain variable region (VH) comprising an amino acid having at least 80% sequence identity to the amino acid sequence of SEQ ID NO: 55 and a light chain variable region (VL) comprising an amino acid sequence having at least 80% sequence identity to the amino acid sequence of SEQ ID NO: 7.

Embodiment A8. The method of Embodiment A7, wherein the anti-MMP-9 antibody or antigen-binding fragment thereof comprises andecaliximab or an antigen-binding fragment thereof.

Embodiment A9. The method of any one of Embodiments A1 to A8, wherein the anti-MMP-9 antibody or antigen-binding fragment thereof comprises one or more amino acid sequences having at least 80% sequence identity to any one of the amino acid sequences listed in Table 1.

Embodiment A10. The method of Embodiment A2, wherein the inhibitory RNA comprises an antisense oligonucleotide (ASO), a short interfering RNA (siRNA), a microRNA (miRNA), a short hairpin RNA (shRNA), or an shRNA-adapted microRNA (shmiRNA).

Embodiment A11. The method of Embodiment A2 or A10, wherein the inhibitory RNA or the CRISPR-Cas system are formulated in a lipid nanoparticle (LNP).

Embodiment A12. A method of treating inflammatory flare-ups in a subject with fibrodysplasia ossificans progressiva (FOP), comprising administering to the subject an MMP-9 inhibitor.

Embodiment A13. The method of Embodiment A12, wherein the inflammatory flare-ups are associated with heterotopic ossification in the subject.

Embodiment A14. The method of Embodiment A12, wherein the inflammatory flare-ups are not associated with heterotopic ossification in the subject.

Embodiment A15. The method of any one of Embodiments A12 to A14, wherein the flare-ups are spontaneous or induced by an external trigger.

Embodiment A16. The method of Embodiment A15, wherein the external trigger is selected from the group consisting of: intra-muscular injections, biopsy, muscle fatigue, dental work, trauma, or infection.

Embodiment A17. The method of any one of Embodiments A12 to A16, wherein the method reduces the frequency of inflammatory flare-ups as compared to the frequency of inflammatory flare-ups prior to administering the MMP-9 inhibitor.

Embodiment A18. The method of any one of Embodiments A12 to A17, wherein the method reduces the severity of inflammatory flare-ups as compared to the severity of inflammatory flare-ups prior to administering the MMP-9 inhibitor.

Embodiment A19. A method of treating a genetic heterotopic ossification (gHO) in a subject in need thereof, comprising administering to the subject an MMP-9 inhibitor.

Embodiment A20. The method of any one of Embodiments A12 to A19, wherein the MMP-9 inhibitor is selected from the group consisting of: an anti-MMP-9 antibody or antigen-binding fragment thereof, an inhibitory RNA, an inhibitory polypeptide, a small molecule inhibitor, and a CRISPR-Cas system.

Embodiment A21. The method of Embodiment A20, wherein the MMP-9 inhibitor is an anti-MMP-9 antibody or antigen-binding fragment thereof.

Embodiment A22. The method of Embodiment A21, wherein the anti-MMP-9 antibody or antigen-binding fragment thereof binds to: (i) an MMP-9 pro-form and inhibits activation of the pro-form; and/or (ii) an MMP-9 active form and inhibits activity of the active form.

Embodiment A23. The method of Embodiment A22, wherein the anti-MMP-9 antibody or antigen-binding fragment thereof binds to the MMP-9 pro-form.

Embodiment A24. The method of Embodiment A22, wherein the anti-MMP-9 antibody or antigen-binding fragment thereof binds to the active form of MMP-9.

Embodiment A25. The method of any one of Embodiments A21 to A24, wherein the anti-MMP-9 antibody or antigen-binding fragment thereof comprises a heavy chain variable region (VH) comprising an amino acid having at least 80% sequence identity to the amino acid sequence of SEQ ID NO: 55 and a light chain variable region (VL) comprising an amino acid sequence having at least 80% sequence identity to the amino acid sequence of SEQ ID NO: 7.

Embodiment A26. The method of Embodiment A25, wherein the anti-MMP-9 antibody or antigen-binding fragment thereof comprises andecaliximab or an antigen-binding fragment thereof.

Embodiment A27. The method of any one of Embodiments A12 to A26, wherein the anti-MMP-9 antibody or antigen-binding fragment thereof comprises one or more amino acid sequences having at least 80% sequence identity to any one of the amino acid sequences listed in Table 1.

Embodiment A28. The method of Embodiment A20, wherein the inhibitory RNA comprises an antisense oligonucleotide (ASO), a short interfering RNA (siRNA), a microRNA (miRNA), a short hairpin RNA (shRNA), or an shRNA-adapted microRNA (shmiRNA).

Embodiment A29. The method of Embodiment A20 or A28, wherein the inhibitory RNA or the CRISPR-Cas system are formulated in a lipid nanoparticle (LNP).

Embodiment A30. The method of any one of Embodiments A12 to A29, wherein the method further comprises administration of an additional active agent or supportive therapy for treating gHO.

Embodiment A31. The method of Embodiment A30, wherein the additional active agent or supportive therapy for treating gHO is selected from the group consisting of: isotretinoin, etidronate with oral corticosteroids, perhexiline maleate, Activin-A inhibitor, Activin A Receptor Type 2 (ALK2) inhibitor, allele-specific RNA interference of ALK2, hypoxia inducible factor-1a (Hif-1α) inhibitor, small molecule inhibitor of Bone Morphogenetic Protein (BMP) signaling, anti-BMP9 antibody or antigen-binding fragment thereof, anti-BMP10 antibody or antigen-binding fragment thereof, anti-TGF-B antibody or antigen-binding fragment thereof, an IL1beta inhibitor, an IL6 inhibitor, momelotinib, chromolyn, imatinib, apyrase, rapamycin, a kinase inhibitor, saracatinib, palovarotene, retinoic acid receptor gamma agonists, retinoic acid receptor alpha agonists, bisphosphonates, radiation therapy, anti-inflammatory agents, physical therapy, and combinations thereof.

Embodiment A32. The method of Embodiment A30 or A31, wherein the additional active agent comprises a second MMP inhibitor selected from the group consisting of an MMP-2 inhibitor, an MMP-7 inhibitor, an MMP-13 inhibitor, an MMP-14 inhibitor, or an MMP-16 inhibitor.

Embodiment A33. The method of any one of Embodiments A30 to A32, wherein the additional active agent or supportive therapy is administered concurrently with the MMP-9 inhibitor.

Embodiment A34. The method of any one of Embodiments A30 to A33, wherein the additional active agent or supportive therapy is administered sequentially with the MMP-9 inhibitor.

Embodiment A35. The method of any one of Embodiments A19 to A34, wherein the gHO is FOP.

Embodiment A36. The method of any one of Embodiments A19 to A35, wherein the gHO is characterized by endochondral ossification.

Embodiment A37. The method of any one of Embodiments A19 to A36, wherein the gHO occurs in one or more tissues selected from the group consisting of bone, skin, subcutaneous tissue, skeletal muscle, tendon, ligament, aponeuroses, fibrotic tissue adjacent to joints, walls of blood vessels, and ligaments.

Embodiment A38. The method of any one of the preceding Embodiments A1 to A37, wherein the MMP-9 inhibitor is administered in a therapeutically effective amount.

Embodiment A39. The method of any one of the proceeding Embodiments A1 to A38, wherein administration of the MMP-9 inhibitor to the subject results in a reduction in symptoms selected form the group consisting of: a number of heterotopic ossifications, size of heterotopic ossifications, growth of heterotopic ossifications, or formation of heterotopic ossifications as compared to the symptoms in the subject prior to administration of the MMP-9 inhibitor.

Embodiment A40. The method of any one of Embodiments A19 to A39, wherein the subject has been identified as exhibiting formation of a gHO.

Embodiment A41. The method of Embodiment A40, wherein the subject has been identified as exhibiting formation of a gHO by way of a triple bone scan, computed tomography (CT) scan or genetic analysis.

Embodiment A42. The method of any one of Embodiments A19 to A41, wherein the MMP-9 inhibitor is an anti-MMP-9 antibody and is administered via subcutaneous administration at a dose of about 50 mg, about 100 mg, about 150 mg, about 200 mg, about 250 mg, about 300 mg, or about 400 mg.

Embodiment A43. The method of any one of the preceding Embodiments A1 to A42, wherein the subject is a human.

Embodiment A44. The method of Embodiment A43, wherein the subject is aged 12 or above or aged 18 or above.

Embodiment A45. The method of Embodiment A43, wherein the subject is aged 6-12.

Embodiment A46. The method of Embodiment A43, wherein the subject is aged 2, 3, 4, 5, 6, 7, 8, 9, 10, 11, 12, 13, 14, 15, 16, 17, 18 or above 18.

Embodiment A47. The method of Embodiment A46, wherein the subject is aged 2-5.

Embodiment A48. The method of Embodiment A46, wherein the subject is aged 6-11.

Embodiment A49. The method of Embodiment A43, wherein the anti-MMP-9 antibody or antigen-binding fragment thereof comprises a heavy chain variable region (VH) comprising an amino acid having at least 80% sequence identity to the amino acid sequence of SEQ ID NO: 55 and a light chain variable region (VL) comprising an amino acid sequence having at least 80% sequence identity to the amino acid sequence of SEQ ID NO: 7.

Embodiment A50. The method of Embodiment A49, wherein the anti-MMP-9 antibody or antigen-binding fragment thereof comprises andecaliximab or an antigen-binding fragment thereof.

Embodiment A51. The method of any one of Embodiments A43 to A50, wherein the subject is aged 2-5, and the antibody or antigen-binding fragment thereof is administered subcutaneously.

Embodiment A52. The method of any one of Embodiment A43 to A50, wherein the subject is aged 6-11, and the antibody or antigen-binding fragment thereof is administered subcutaneously.

Embodiment A53. The method of Embodiment A50, wherein the subject is aged from about 6 to about 11 years, and wherein the andecaliximab or an antigen-binding fragment thereof is administered about every week at a dose of from about 25 mg to about 75 mg.

Embodiment A54. The method of Embodiment A50, wherein the subject is aged from about 6 to about 11 years, and wherein the andecaliximab or an antigen-binding fragment thereof is administered from about every 8 days to about every 16 days at a dose of from about 25 mg to about 75 mg.

Embodiment A55. The method of Embodiment A50, wherein the subject is aged from about 2 to about 5 years, and wherein the andecaliximab or an antigen-binding fragment thereof is administered about every week at a dose of from about 15 mg to about 50 mg.

Embodiment A56. The method of Embodiment A50, wherein the subject is aged from about 2 to about 5 years, and wherein the andecaliximab or an antigen-binding fragment thereof is administered from about every 8 days to about every 16 days at a dose of from about 15 mg to about 50 mg.

Embodiment A57. The method of Embodiment A50, wherein the subject is aged from about 6 to about 11 years, and wherein the andecaliximab or an antigen-binding fragment thereof is administered subcutaneously about every week at a dose of about 25 mg, about 50 mg or about 75 mg.

Embodiment A58. The method of Embodiment A50, wherein the subject is aged from about 2 to about 5 years, and wherein the andecaliximab or an antigen-binding fragment thereof is administered subcutaneously from about every other week at a dose of about 15 mg, about 45 mg or about 50 mg.

Embodiment A59. The method of Embodiment A50, wherein the subject is aged from about 12 to about 50 years, and wherein the andecaliximab or an antigen-binding fragment thereof is administered subcutaneously from about every week at a dose of about 150 mg.

Embodiment A60. The method of Embodiment A50, wherein the subject is aged from about 12 to about 50 years, and wherein the andecaliximab or an antigen-binding fragment thereof is administered subcutaneously from about every week at a dose of about 50 mg.

Embodiment A61. The method of Embodiment A50, wherein the subject is aged from about 12 to about 50 years, and wherein the andecaliximab or an antigen-binding fragment thereof is administered subcutaneously from about every 8 days to about every 16 days at a dose of about 150 mg.

Embodiment A62. The method of Embodiment A50, wherein a single or not more than three loading doses are administered subcutaneously followed by a maintenance dose of from about 15 mg to about 75 mg. administered subcutaneously from about every seven to about every fourteen days, wherein the loading dose is greater than the maintenance dose.

Embodiment A63. The method of Embodiment A50, wherein the subject is aged from about 2 to about 11 years, and wherein the andecaliximab or an antigen-binding fragment thereof is administered about subcutaneously in a sustained release formulation.

Embodiment A64. The method of any one of Embodiments A19 to A63, wherein the subject has a gain-of-function mutation in the ACVR1/ALK2 gene.

Embodiment A65. The method of Embodiment A64, wherein the gain-of-function mutation the ACVR1/ALK2 gene is R206H.

Embodiment A66. The method of any one of Embodiments A1 to A41, wherein the MMP-9 inhibitor is administered by way of systemic delivery.

Embodiment A67. The method of Embodiment A5, wherein the systemic delivery comprises intravenous, intraarterial, intramuscular, subcutaneous, intraperitoneal, or intra-thoracic administration.

Embodiment A68. The method of any one of Embodiments A1 to A41, wherein the MMP-9 inhibitor is administered by way of local delivery.

Embodiment A69. The method of Embodiment A7, wherein the local delivery comprises direct injection into an area of heterotopic ossification, a tissue, or an organ.

Embodiment A70. The method of any one of preceding Embodiments A1 to A69, wherein the MMP-9 inhibitor is administered to the subject for a duration that is between one month and 90 years.

Embodiment A71. The method of any one of the preceding Embodiments A1 to A70, wherein administration of the MMP-9 inhibitor begins between the age of 2 and 18 and terminates between the age of 30 and 100.

Embodiment A72. The method of any one of the preceding Embodiments A1 to A71, wherein the MMP-9 inhibitor has no detectable inhibitory activity to human MMP-2.

Embodiment A73. A pharmaceutical composition comprising an inhibitory IgG4 antibody selective for matrix metalloproteinase-9 (MMP-9) with no detectable inhibitory activity to human MMP-2, in an amount effective to reduce heterotopic bone formation in a tissue selected from muscle, tendon, ligament, and fascia in a human subject under the age of about thirty and having a gain-of-function mutation in the ACVR1/ALK2 gene, when administered once daily by intravenous or subcutaneous administration to the human subject.

Embodiment A74. The pharmaceutical composition of Embodiment A73, wherein the inhibitory IgG4 antibody comprises andecaliximab, and wherein the human subject comprises an R206H mutation in the ACVR1/ALK2 gene.

Embodiment A75. The pharmaceutical composition of Embodiment A73 or A74, wherein the inhibitory IgG4 antibody comprises andecaliximab, and wherein the human subject has at least one symptom of fibrodysplasia ossificans progressive (FOP).

Embodiment A76. The pharmaceutical composition of any one of Embodiments A73 to A75, wherein the composition is formulated for subcutaneous administration.

Embodiment A77. A unit dosage comprising the pharmaceutical composition of Embodiment A73, wherein the inhibitory IgG4 antibody comprises andecaliximab, in an amount effective to reduce heterotopic bone formation in a tissue selected from muscle, tendon, ligament, and fascia by at least about 10% over a period of no greater than about four weeks in a human subject under the age of about thirty and having a gain-of-function mutation in the ACVR1/ALK2 gene, when administered once daily by intravenous or subcutaneous administration to the human subject.

Embodiment A78. The unit dosage of Embodiment A77, wherein the dosage is formulated for subcutaneous administration.

OTHER EMBODIMENTS

While the invention has been particularly shown and described with reference to a preferred embodiment and various alternate embodiments, it will be understood by persons skilled in the relevant art that various changes in form and details can be made therein without departing from the spirit and scope of the invention. All references, issued patents and patent applications cited within the body of the instant specification are hereby incorporated by reference in their entirety, for all purposes.

TABLE 1

SEQUENCE LISTING

| SEQ ID NO | Sequence | Description |
| --- | --- | --- |
| 1 | MAVLVLFLCLVAFPSCVLSQVQLKESGP GLVAPSQSLSITCTVSGFSLLSYGVHWVR QPPGKGLEWLGVIWTGGTTNYNSALMS RLSISKDDSKSQVFLKMNSLQTDDTAIYY CARYYYGMDYWGQGTSVTVSSAKTTPP SVYPLAPGCGDTTGSSVTLGCLVKGYFPE SVTVTWNSGSLSSSVHTFPALLQSGLYT MSSSVTVPSSTWPSQTVTCSVAHPASSTT VDKKLEPSGPISTINPCPPCKECHKCPAPN LEGGPSVFIFPPNIKDVLMISLTPKVTCVV VDVSEDDPDVRISWFVNNVEVHTAQTQT HREDYNSTIRVVSALPIQHQDWMSGKEF KCKVNNKDLPSPIERTISKIKGLVRAPQV YILPPPAEQLSRKDVSLTCLVVGFNPGDIS VEWTSNGHTEENYKDTAPVLDSDGSYFI YSKLDIKTSKWEKTDSFSCNVRHEGLKN YYLKKTISRSPGK | AB0041 heavy chain |
| 2 | MESQIQVFVFVFLWLSGVDGDIVMTQSH KFMSTSVGDRVSITCKASQDVRNTVAWY QQKTGQSPKLLIYSSSYRNTGVPDRFTGS GSGTDFTFTISSVQAEDLAVYFCQQHYIT PYTFGGGTKLEIKRADAAPTVSIFPPSSEQ LTSGGASVVCFLNNFYPKDINVKWKIDG SERQNGVLNSWTDQDSKDSTYSMSSTLT LTKDEYERHNSYTCEATHKTSTSPIVKSF NRNEC | AB0041 light chain |
| 3 | QVQLKESGPGLVAPSQSLSITCTVSGFSLL SYGVHWVRQPPGKGLEWLGVIWTGGTT NYNSALMSRLSISKDDSKSQVFLKMNSL QTDDTAIYYCARYYYGMDYWGQGTSVT VSS | AB0041 heavy chain variable region |
| 4 | QVQLQESGPGLVKPSETLSLTCTVSGFSL LSYGVHWVRQPPGKGLEWLGVIWTGGT TNYNSALMSRLTISKDDSKSTVYLKMNS LKTEDTAIYYCARYYYGMDYWGQGTSV TVSS | AB0041 variant 1 heavy chain variable region (VH1) |
| 5 | QVQLQESGPGLVKPSETLSLTCTVSGFSL LSYGVHWVRQPPGKGLEWLGVIWTGGT TNYNSALMSRLTISKDDSKNTVYLKMNS LKTEDTAIYYCARYYYGMDYWGQGTLV TVSS | AB0041 variant 2 heavy chain variable region (VH2) |
| 6 | DIQMTQSPSSLSASVGDRVTITCKASQDV RNTVAWYQQKPGKAPKLLIYSSSYRNTG VPDRFSGSGSGTDFTLTISSLQAEDVAVY FCQQHYITPYTFGGGTKVEIK | AB0041 variant 3 light chain variable region (VK3) |

TABLE 1-continued

SEQUENCE LISTING

| SEQ ID NO | Sequence | Description |
|---|---|---|
| 7 | DIQMTQSPSSLSASVGDRVTITCKASQDV RNTVAWYQQKPGKAPKLLIYSSSYRNTG VPDRFSGSGSGTDFTLTISSLQAEDVAVY YCQQHYITPYTFGGGTKVEIK | andecaliximab and AB0041 variant 4 (VK4) light chain variable region |
| 8 | GFSLLSYGVH | Heavy chain CDR1 for: Andecaliximab AB0041 AB0041 VH variants 1-4 M4 |
| 9 | VIWTGGTTNYNSALMS | Heavy chain CDR2 for: Andecaliximab AB0041 AB0041 VH variants 1-4 M4 |
| 10 | YYYGMDY | Heavy chain CDR3 for: Andecaliximab AB0041 AB0041 VH variants 1-4 M4 |
| 11 | KASQDVRNTVA | Light chain CDR1 for: Andecaliximab AB0041 AB0041 VK variants 1-4 M4 |
| 12 | SSSYRNT | Light chain CDR2 for: Andecaliximab AB0041 AB0041 VK variants 1-4 M4 |
| 13 | QQHYITPYT | Light chain CDR5 for: Andecaliximab AB0041 AB0041 VK variants 1-4 M4 |
| 14 | MSLWQPLVLVLLVLGCCFAAPRQRQSTL VLFPGDLRTNLTDRQLAEEYLYRYGYTR VAEMRGESKSLGPALLLLQKQLSLPETGE LDSATLKAMRTPRCGVPDLGRFQTFEGD LKWHHHNITYWIQNYSEDLPRAVIDDAF ARAFALWSAVTPLTFTRVYSRDADIVIQF GVAEHGDGYPFDGKDGLLAHAFPPGPGI QGDAHFDDDELWSLGKGVVVPTRFGNA DGAACHFPFIFEGRSYSACTTDGRSDGLP WCSTTANYDTDDRFGFCPSERLYTRDGN ADGKPCQFPFIFQGQSYSACTTDGRSDGY RWCATTANYDRDKLFGFCPTRADSTVM GGNSAGELCVFPFTFLGKEYSTCTSEGRG DGRLWCATTSNFDSDKKWGFCPDQGYS LFLVAAHEFGHALGLDHSSVPEALMYPM YRFTEGPPLHKDDVNGIRHLYGPRPEPEP RPPTTTTPQPTAPPTVCPTGPPTVHPSERP TAGPTGPPSAGPTGPPTAGPSTATTVPLSP VDDACNVNIFDAIAEIGNQLYLFKDGKY WRFSEGRGSRPQGPFLIADKWPALPRKL DSVFEEPLSKKLFFFSGRQVWVYTGASV LGPRRLDKLGLGADVAQVTGALRSGRG KMLLFSGRRLWRFDVKAQMVDPRSASE VDRMFPGVPLDTHDVFQYREKAYFCQD RFYWRVSSRSELNQVDQVGYVTYDILQC PED | Human MMP-9 protein (with signal peptide) |
| 15 | APRQRQSTLVLFPGDLRTNLTDRQLAEE YLYRYGYTRVAEMRGESKSLGPALLLLQ KQLSLPETGELDSATLKAMRTPRCGVPD LGRFQTFEGDLKWHHHNITYWIQNYSED LPRAVIDDAFARAFALWSAVTPLTFTRV YSRDADIVIQFGVAEHGDGYPFDGKDGL | Human MMP-9 protein (without signal peptide) |

TABLE 1-continued

SEQUENCE LISTING

| SEQ ID NO | Sequence | Description |
|---|---|---|
| | LAHAFPPGPGIQGDAHFDDDELWSLGKG VVVPTRFGNADGAACHFPFIFEGRSYSAC TTDGRSDGLPWCSTTANYDTDDRFGFCP SERLYTRDGNADGKPCQFPFIFQGQSYSA CTTDGRSDGYRWCATTANYDRDKLFGF CPTRADSTVMGGNSAGELCVFPFTFLGK EYSTCTSEGRGDGRLWCATTSNFDSDKK WGFCPDQGYSLFLVAAHEFGHALGLDHS SVPEALMYPMYRFTEGPPLHKDDVNGIR HLYGPRPEPEPRPPTTTTPQPTAPPTVCPT GPPTVHPSERPTAGPTGPPSAGPTGPPTA GPSTATTVPLSPVDDACNVNIFDAIAEIGN QLYLFKDGKYWRFSEGRGSRPQGPFLIA DKWPALPRKLDSVFEEPLSKKLFFFSGRQ VWVYTGASVLGPRRLDKLGLGADVAQV TGALRSGRGKMLLFSGRRLWRFDVKAQ MVDPRSASEVDRMFPGVPLDTHDVFQYR EKAYFCQDRFYWRVSSRSELNQVDQVG YVTYDILQCPED | |
| 16 | MSLWQPLVLVLLVLGCCFA | MMP-9 signal peptide |
| 17 | MAVLVLFLCLVAFPSCVLSQVQLKESGP GLVAPSQSLSITCTVSGFSLLSYGVHWVR QPPGKGLEWLGVIWTGGSTNYNSALMSR LSISKDDSKSQVFLKMNSLQTDDTAMYY CARYYYAMDYWGQGTSVTVSSAKTTPP SVYPLAPGCGDTTGSSVTLGCLVKGYFPE SVTVTWNSGSLSSSVHTFPALLQSGLYT MSSSVTVPSSTWPSQTVTCSVAHPASSTT VDKKLEPSGPISTINPCPPCKECHKCPAPN LEGGPSVFIFPPNIKDVLMISLTPKVTCVV VDVSEDDPDVRISWFVNNVEVHTAQTQT HREDYNSTIRVVSALPIQHQDWMSGKEF KCKVNNKDLPSPIERTISKIKGLVRAPQV YILPPPAEQLSRKDVSLTCLVVGFNPGDIS VEWTSNGHTEENYKDTAPVLDSDGSYFI YSKLDIKTSKWEKTDSFSCNVRHEGLKN YYLKKTISRSPGK | M4 hybridoma antibody heavy chain |
| 18 | MESQIQVFVFVFLWLSGVDGDIVMTQSH KFMFTSVGDRVSITCKASQDVRNTVAWY QQKTGQSPKLLIYSASYRNTGVPDRFTGS ISGTDFTFTISSVQAEDLALYYCQQHYSTP YTFGGGTKLEVKRADAAPTVSIFPPSSEQ LTSGGASVVCFLNNFYPKDINVKWKIDG SERQNGVLNSWTDQDSKDSTYSMSSTLT LTKDEYERHNSYTCEATHKTSTSPIVKSF NRNEC | M4 hybridoma antibody light chain |
| 19 | QVQLKESGPGLVAPSQSLSITCTVSGFSLL SYGVHWVRQPPGKGLEWLGVIWTGGST NYNSALMSRLSISKDDSKSQVFLKMNSL QTDDTAMYYCARYYYAMDYWGQGTSV TVSS | M4 hybridoma antibody heavy chain variable region |
| 20 | DIVMTQSHKFMFTSVGDRVSITCKASQD VRNTVAWYQQKTGQSPKLLIYSASYRNT GVPDRFTGSISGTDFTFTISSVQAEDLALY YCQQHYSTPYTFGGGTKLEVK | M4 hybridoma antibody light chain variable region |
| 21 | GFSLLSYGVH | M4 hybridoma antibody heavy chain CDR1 |
| 22 | VIWTGGSTNYNSALMS | M4 hybridoma antibody heavy chain CDR2 |
| 23 | YYYAMDY | M4 hybridoma antibody heavy chain CDR3 |

TABLE 1-continued

SEQUENCE LISTING

| SEQ ID NO | Sequence | Description |
|---|---|---|
| 24 | KASQDVRNTVA | M4 hybridoma antibody light chain CDR1 |
| 25 | SASYRNT | M4 hybridoma antibody light chain CDR2 |
| 26 | QQHYSTPYT | M4 hybridoma antibody light chain CDR3 |
| 27 | QVFVYMLLWLSGVDGDIVMTQSQKFMS TSVGDRVSVTCKASQNVGTNVAWYQQK PGQSPKALIYSASYRFSGVPDRFTGSGSG TDFTLTISNVQSEDLAEYFCQQYNSYPYT FGGGTKLEIKRADAAPTVSIFPPSSEQLTS GGASVVCFLNNFYPKDINVKWKIDGSER QNGVLNSWTDQDSKDSTYSMSSTLTLTK DEYERHNSYTCEATHKTSTSPIVKSFNRN EC | M12 hybridoma light chain |
| 28 | DIVMTQSQKFMSTVGDRVSVTCKASQN VGTNVAWYQQKPGQSPKALIYSASYRFS GVPDRFTGSGSGTDFTLTISNVQSEDLAE YFCQQYNSYPYTFGGGTKLEIK | M12 hybridoma light chain variable region |
| 29 | KASQNVGTNVA | M12 hybridoma light chain CDR1 |
| 30 | SASYRFS | M12 hybridoma light chain light chain CDR2 |
| 31 | QQYNSYPYT | M12 hybridoma light chain light chain CDR3 |
| 32 | MSSAQFLGLLLLCFQGTRCDIQMTQTTSS LSASLGDRVTISCSASQGISNYLNWYQQK PDGTFKLLIYYTSILHSGVPSRFSGSGSGT DYSLTISNLEPEDIATYYCQQYGWLPRTF GGGTKLEIKRADAAPTVSIFPPSSEQLTSG GASVVCFLNNFYPKDINVKWKIDGSERQ NGVLNSWTDQDSKDSTYSMSSTLTLTKD EYERHNSYTCEATHKTSTSPIVKSFNRNE C | AB0046 light chain |
| 33 | MGWSSIILFLVATATGVHSQVQLQQPGS VLVRPGASVKLSCTASGYTFTSYWMNW VKQRPGQGLEWIGEIYPISGRTNYNEKFK VKATLTVDTSSSTAYMDLNSLTSEDSAV YYCARSRANWDDYWGQGTTLTVSSAKT TPPSVYPLAPGSAAQTNSMVTLGCLVKG YFPEPVTVTWNSGSLSSGVHTFPAVLQSD LYTLSSSVTVPSSTWPSETVTCNVAHPAS STKVDKKIVPRDCGCKPCICTVPEVSSVFI FPPKPKDVLTITLTPKVTCVVVDISKDDPE VQFSWFVDDVEVHTAQTQPREEQFNSTF RSVSELPIMHQDWLNGKEFKCRVNSAAF PAPIEKTISKTKGRPKAPQVYTIPPPKEQM AKDKVSLTCMITDFFPEDITVEWQWNGQ PAENYKNTQPIMDTDGSYFVYSKLNVQK SNWEAGNTFTCSVLHEGLHNHHTEKSLS HSPGK | AB0046 heavy chain |
| 34 | DIQMTQTTSSLSASLGDRVTISCSASQGIS NYLNWYQQKPDGTFKLLIYYTSILHSGVP SRFSGSGSGTDYSLTISNLEPEDIATYYCQ QYGWLPRTFGGGTKLEIKR | AB0046 light chain variable region |
| 35 | MGWSLILLFLVAVATRVHSQVQLQESGP GLVKPSETLSLTCTVSGFSLLSYGVHWVR QPPGKGLEWLGVIWTGGTTNYNSALMS RFTISKDDSKNTVYLKMNSLKTEDTAIYY CARYYYGMDYWGQGTLTVTSSASTKGP SVFPLAPCSRSTSESTAALGCLVKDYFPEP VTVSWNSGALTSGVHTFPAVLQSSGLYS LSSVVTVPSSSLGTKTYTCNVDHKPSNTK | andecaliximab heavy chain |

TABLE 1-continued

SEQUENCE LISTING

| SEQ ID NO | Sequence | Description |
|---|---|---|
| | VDKRVESKYGPPCPPCPAPEFLGGPSVFL FPPKPKDTLMISRTPEVTCVVVDVSQEDP EVQFNWYVDGVEVHNAKTKPREEQFNS TYRVVSVLTVLHQDWLNGKEYKCKVSN KGLPSSIEKTISKAKGQPREPQVYTLPPSQ EEMTKNQVSLTCLVKGFYPSDIAVEWES NGQPENNYKTTPPVLDSDGSFFLYSRLTV DKSRWQEGNVFSCSVMHEALHNHYTQK SLSLSLGK | |
| 36 | MRVPAQLLGLLLLWLPGARCDIQMTQSP SSLSASVGDRVTITCKASQDVRNTVAWY QQKPGKAPKLLIYSSSYRNTGVPDRFSGS GSGTDFTLTISSLQAEDVAVYYCQQHYIT PYTFGGGTKVEIKRTVAAPSVFIFPPSDEQ LKSGTASVVCLLNNFYPREAKVQWKVD NALQSGNSQESVTEQDSKDSTYSLSSTLT LSKADYEKHKVYACEVTHQGLSSPVTKS FNRGEC | andecaliximab light chain |
| 37 | MESQIQVFVFVFLWLSGVDGDIVMTQSH KFMFTSVGDRVSITCKASQDVRNTVAWY QQKTGQSPKLLIYSASYRNTGVPDRFTGS ISGTDFTFTISSVQAEDLALYYCQQHYSTP YTFGGGTKLEVKRADAAPTVSIFPPSSEQ LTSG | M4 hybridoma light chain |
| 38 | QVFVYMLLWLSGVDGDIVMTQSQKFMS TSVGDRVSVTCKASQNVGTNVAWYQQK PGQSPKALIYSASYRFSGVPDRFTGSGSG TDFTLTISNVQSEDLAEYFCQQYNSYPYT FGGGTKLEIKRADAAPTVSIFPPSSEQLTS G | anti-MMP-9 light chain |
| 39 | MAVLVLFLCLVAFPSCVLSQVQLKESGP GLVAPSQSLSITCTVSGFSLLSYGVHWVR QPPGKGLEWLGVIWTGGSTNYNSALMSR LSISKDDSKSQVFLKMNSLQTDDTAMYY CARYYYAMDYWGQGTSVTVSSAKTTPP SVYPLAPGCGDTTGSSVTLGCLVKGYFPE SVTVTWNSGSL | anti-MMP-9 heavy chain |
| 40 | FQTFEGD | neo epitope |
| 41 | QTFEGD | neo epitope fragment |
| 42 | VPDLGRFQTFEGD | total cleavage site |
| 43 | QSVEESGGRLVTPGTPLTLTCTASGFTISS YHMTWVRQAPMKGLEWIGTISSSGSTYY ASWAKGRFTISKTSSTTVDLKITSPATEDT ATYFCARSVPGDSSGEIWGRGTLVTVSSG QPKAPSVFPLAPCCGDTPSSTVTLGCLVK GYLPEPVTVTWNSGTLTNGVRTFPSVRQ SSGLYSLSSVVSVTSSSQPVTCNVAHPAT NTKVDKTVAPSTCSKPTCPPPELLGGPSV FIFPPKPKDTLMISRTPEVTCVVVDVSQD DPEVQFTWYINNEQVRTARPPLREQQFN STIRVVSTLPIAHQDWLRGKEFKCKVHN KALPAPIEKTISKARGQPLEPKVYTMGPP REELSSRSVSLTCMINGFYPSDISVEWEK NGKAEDNYKTTPAVLDSDGSYFLYSKLS VPTSEWQRGDVFTCSVMHEALHNHYTQ KSISRSPGK | anti-MMP-9 heavy chain |
| 44 | AQVLTQTASPVSAAVGGTVTINCQSSQS VYNKNWLAWYQQKPGQPPKRLIYSAST LDSGVSSRFKGSGSGTQFTLTISGVQCDD AATYYCQGEFSCSRGDCSAFGGGTEVVV QGDPVAPTVLIFPPSADLVATGTVTIVCV ANKYFPDVTVTWEVDGTTQTTGIENSKT PQNSADCTYNLSSTLTLSTQYNSHKEYT CKVTQGTTSVVQSFNRGDC | anti-MMP-9 light chain |

TABLE 1-continued

SEQUENCE LISTING

| SEQ ID NO | Sequence | Description |
|---|---|---|
| 45 | VIWTGGSTNY | heavy chain CDR1 |
| 46 | QVQLKESGPGLVAPSQSLSITCTVSGFSLL SYGVIIWVRQPPGKGLEWLGVIWTGGTT NYNSALMSRLSISKDDSKSQVFLKMNSL QTDDTAIYYCARYYYGMDYWGQGTSVT VSS | Anti-MMP-9 heavy chain variable region |
| 47 | DIVMTQSHKFMSTSVGDRVSITCKASQD VRNTVAWYQQKTGQSPKLLIYSSSYRNT GVPDRFTGSGSGTDFTFTISSVQAEDLAV YFCQQHYITPYTFGGGTKLEIKR | AB0041 light chain variable region |
| 48 | QVQLQESGPGLVKPSETLSLTCTVSGFSL LSYGVIIWVRQPPGKGLEWLGVIWTGGT TNYNSALMSRLTISKDDSKSTVYLKMNS LKTEDTAIYYCARYYYGMDYWGQGTSV TVSS | Anti-MMP-9 heavy chain variable region |
| 49 | MSSAQFLGLLLLCFQGTRCDIQMTQTTSS LSASLGDRVTISCSASQGISNYLNWYQQK PDGTFKLLIYYTSILIISGVPSRFSGSGSGT DYSLTISNLEPEDIATYYCQQYGWLPRTF GGGTKLEIKRADAAPTVSIFPPSEQLTSGG ASVVCFLNNFYPKDINVKWKIDGSERQN GVLNSWTDQDSKDSTYSMSSTLTLTKDE YERHSYTCEATHKTSPIVKSFNRNEC | anti-MMP-9 light chain |
| 50 | MGWSSIILLTVATATGVHSQVQLQQPGS VLVRPGASVKLSCTASGYTFTSYWMNW VKQRPGQGLEWIGEIYPISGRTNYNEKFK VKATLTVDTSSSTAYMDLNSLTSEDSAV YYCARSRANWDDYWGQGTTLTVSSAKT TPPSVYPLAPGSAAQTNSMVTLCLVKGY FPEPVTVTWNSGSLSSGVHTFPAVLQSDL YTLSSSVTVPSSTWPSETVTCNVAHPASS TKVDKKIVPRDCGCKPCICTVPEVSSVFIF PPKPKDVLTITLTPKVTCVVVDISKDDPE VQFSWFVDDVEVHTAQTQPREEQFNSTF RSVSELPIMHQDWLNGKEFKCRVNSAAF PAPIEKTISKTKGRPKAPQVYTIPPPKEQM AKDKVSLTCMITDFFPEDITVEWQWNGQ PAENTYKNTQPIMDTDGSYFVYSKLNVQ KSNWEAGNTFTCSVLHEGLHNHHTEKSL SHSPGK | anti-MMP9 heavy chain |
| 51 | QVQLQQPGSVLVRPGASVKLSCTASGYT FTSYWMNWVKQRPGQGLEWIGEIYPISG RTNYNEKFKVKATLTVDTSSSTAYMDLN SLTSEDSAVYYCARSRANWDDYWGQGT TLTVSS | AB0046 heavy chain variable region |
| 52 | DIQMTQTTSSLSASLGDRVTISCSASQGIS NYLNWYQQKPDGTFKLLIYYTSILHSGVP SRESGSGSGTDYSLTISNLEPEDIATYYCQ QYGWLPRTFGGGTKLEIK | Anti-MMP-9 light chain variable region |
| 53 | QVQLQESGPGLVKPSETLSLTCTVSGFSL LSYGVIIWVRQPPGKGLEWLGVIWTGGT TNYNSALMSRLTISKDDSKSTVYLKMNS LKTEDTAIYYCARYYYGMDYWGQGTSV TVSS | AB0041 variant 1 heavy chain variable region (VH1) (duplicate) |
| 54 | QVQLQESGPGLVKPSETLSLTCTVSGFSL LSYGVHWVRQPPGKGLEWLGVIWTGGT NYNSALMSRLTISKDDSKNTVYLKMNSL KTEDTAIYYCARYYYGMDYWGQGTLVT VSS | Anti-MMP-9 heavy chain variable region |
| 55 | QVQLQESGPGLVKPSETLSLTCTVSGFSL LSYGVHWVRQPPGKGLEWLGVIWTGGT TNYNSALMSRFTISKDDSKNTVYLKMNS LKTEDTAIYYCARYYYGMDYWGQGTLV TVSS | AB0041 variant 3 AND andecaliximab heavy chain variable region |

TABLE 1-continued

SEQUENCE LISTING

| SEQ ID NO | Sequence | Description |
|---|---|---|
| 56 | QVQLQESGPGLVKPSETLSLTCTVSGFSL LSYGVHWVRQPPGKGLEWLGVIWTGGT TNYNSALMSRFTISKDDSKNTLYLKMNS LKTEDTAIYYCARYYYGMDYWGQGTLV TVSS | AB0041 variant 4 heavy chain variable region |
| 57 | DIVMTQSPSFLSASVGDRVTITCKASQDV RNTVAWYQQKTGKAPKLLIYSSSYRNTG VPDRFTGSGSGTDFTLTISSLQAEDVAVY FCQQHYITPYTFGGGTKVEIK | AB0041 variant 1 variable light chain (VK1) |
| 58 | DIVMTQSPSSLSASVGDRVTITCKASQDV RNTVAWYQQKPGKAPKLLIYSSSYRNTG VPDRFTGSGSGTDFTLTISSLQAEDVAVY FCQQHYITPYTFGGGTKVEIK | AB0041 variant 2 variable light chain (VK2) |
| 59 | DIQMTQSPSSLSASVGDRVTITCKASQDV RNTVAWYQQKPGKAPKLLITYSSSYRNT GVPDRFSGSGSGTDFTLTISSLQAEDVAV YFCQQHYITPYTFGGGTKVEIK | Anti-MMP-9 Variable light chain |
| 60 | DIQMTQSPSSLSASVGDRVTITCKASQDV RNTVAWYQQKPGKAPKLLITYSSSYRNT GVPDRFSGSGSGTDFTLTISSLQAEDVAV YYCQQHYITPYTFGGGTKVEIK | Anti-MMP-9 Variable light chain |
| 61 | α1(V)GlyΨ{PO$_2$H-CH$_2$}Val THPI[C$_6$-(Gly-Pro-Hyp)$_4$-Gly-Pro-Pro-GlyΨ{PO$_2$H-CH$_2$}(R,S)Val-Val-Gly-Glu-Gln-Gly-Glu-Gln-Gly-Pro-Pro-(Gly-Pro-Hyp)$_4$-NH$_2$] | Inhibitory MMP-9 polypeptide |
| 62 | α1(V)GlyΨ{PO$_2$H-CH$_2$}Val[mep$_{14, 32}$, Flp$_{15, 33}$]THPI | Inhibitory MMP-9 polypeptide |
| 63 | UACAUGAGCGCUUCCGGCAC | Inhibitory RNA targeting MMP-9 |
| 64 | UACAUGAGCGCCUCCGGCAC | Inhibitory RNA targeting MMP-9 |
| 65 | UUCACCCGGUUGUGGAAACU | Inhibitory RNA targeting MMP-9 |
| 66 | GGGGCUGCCAGGGACUCAU | Inhibitory RNA targeting MMP-9 |
| 67 | GCUUUCUCUCGGUACUGGAAGACGU | Inhibitory RNA targeting MMP-9 |
| 68 | GCUGACUACGAUAAGGACGGCA | Inhibitory RNA targeting MMP-9 |
| 69 | GCUCAUUGGUGAGGGCAGAGG | Inhibitory RNA targeting MMP-9 |
| 70 | AGACACCUCUGCCCUCACCAUGAG | Inhibitory RNA targeting MMP-9 |
| 71 | AACUGGAUGACGAUGUCUGCGUCC | Inhibitory RNA targeting MMP-9 |
| 72 | GGAGCACGGAGACGGGUAU | Inhibitory RNA targeting MMP-9 |
| 73 | CUGUCUGGGGCUCAUGGUGA | Inhibitory RNA targeting MMP-9 |
| 74 | AAUCUCGAGAGACACCUCUGCCCUCAC CAUGAG | Inhibitory RNA targeting MMP-9 |
| 75 | GUCGUGCGUGUCCAAAGGCA | Inhibitory RNA targeting MMP-9 |
| 76 | CUAUGGUCCUCGCCCUGAAUU | Inhibitory RNA targeting MMP-9 |
| 77 | UUCAGGGGCGACCAUAGUU | Inhibitory RNA targeting MMP-9 |
| 78 | ACUACUGUGCCUUUGAGUCC | Inhibitory RNA targeting MMP-9 |
| 79 | GUUGGCAGUGCAAUACCUGA | Inhibitory RNA targeting MMP-9 |
| 80 | GUCGCCCUCAAAGGUUUGGAAU | Inhibitory RNA targeting MMP-9 |
| 81 | FFAGLDD | Inhibitory MMP-9 polypeptide |

TABLE 1-continued

SEQUENCE LISTING

| SEQ ID NO | Sequence | Description |
|---|---|---|
| 82 | CTTHWGFTLC | Inhibitory MMP-9 polypeptide |
| 83 | VQLQESGGGLVKPGGSLKLSCAASGFAF STYDMSWIRQTPEKRLEWVATISSGGSYT YYPDSVKGRFTISKDNARNTLYLQMSSL RSGDTALYYCTRFRYDGWYFDVWGQG | SDS3 variable heavy chain region |
| 84 | DVLITQTPLSLPVSLGDQASISCRSSQSIV HSNGNTFLEWYLQKPGQSPKLLIYKVSN RFSGVPDRFSGSGSGTDFTLKISRVEAED LGVYYCFQASHVPPTFGG | SDS3 variable light chain region |
| 85 | STYDM | SDS3 HCDR1 |
| 86 | TISSGGSYTYYPDSVK | SDS3 HCDR2 |
| 87 | FRYDGWYFDV | SDS3 HCDR3 |
| 88 | RSSQSIVHSNGNTFLE | SDS3 LCDR1 |
| 89 | KVSNRFS | SDS3 LCDR2 |
| 90 | FQASHVPPT | SDS3 LCDR3 |
| 91 | EVQLQQSGPELVKPGASVKISCKASGYTF TGYYMHWVKQSPEKSLEWIGEINPSTGG TTYNQKFTGKATLTVDKSSSTAYMQLKS LTSDDSAVYYCASYYRYDWFAYWGQGT LVTVSA | SDS4 variable heavy chain region |
| 92 | MADVLMTQTPLSLPVSLGDQASISCRSSQ SLVHSNGNTYLHWYLQKPGQSPKLLIYK VSNRFSGVPDRFSGSGSGTDFTLKISRVE AEDLGVYFCSQSTHVPFTFGSGTKLELKR | SDS4 variable light chain region |
| 93 | GYYMH | SDS4 HCDR1 |
| 94 | EINPSTGGTTYNQKFTG | SDS4 HCDR2 |
| 95 | YYRYDWFAY | SDS4 HCDR3 |
| 96 | RSSQSLVHSNGNTYLH | SDS4 LCDR1 |
| 97 | KVSNRFS | SDS4 LCDR2 |
| 98 | SQSTHVPFT | SDS4 LCDR3 |
| 99 | QVQLQQSGAELVMPGASVKMSCKASGY TFTDYWMHWVKQRPGQGLEWIGAIDTS DTYTRYNQKFKGKATLTVDESSSTAYMQ ASSLTSEDSAVYYCARAVIIYGSSWGYFD VWGQGTTVTVSS | REGA-3G12 variable heavy chain region |
| 100 | DIELTQSPSYLAASPGETITINCRASKSISK YLAWYQEKPGKTNKLLIYSGSTLQSGIPS RFSGSGSGTDFTLTISSLEPEDFAMYYCQ QHNEYPYTFGGGTKLEIK | REGA-3G12 variable light chain region |
| 101 | DYWMH | REGA-3G12 HCDR1 |
| 102 | AIDTSDTYTRYYNQKFKG | REGA-3G12 HCDR2 |
| 103 | AVIIYGSSWGYFDV | REGA-3G12 HCDR3 |
| 104 | RASKSISKYLA | REGA-3G12 LCDR1 |
| 105 | SGSTLQS | REGA-3G12 LCDR2 |
| 106 | QQHNEYPYT | REGA-3G12 LCDR3 |

SEQUENCE LISTING

```
Sequence total quantity: 106
SEQ ID NO: 1            moltype = AA   length = 470
FEATURE                 Location/Qualifiers
source                  1..470
                        mol_type = protein
                        organism = synthetic construct
SEQUENCE: 1
MAVLVLFLCL VAFPSCVLSQ VQLKESGPGL VAPSQSLSIT CTVSGFSLLS YGVHWVRQPP    60
GKGLEWLGVI WTGGTTNYNS ALMSRLSISK DDSKSQVFLK MNSLQTDDTA IYYCARYYYG   120
MDYWGQGTSV TVSSAKTTPP SVYPLAPGCG DTTGSSVTLG CLVKGYFPES VTVTWNSGSL   180
SSSVHTFPAL LQSGLYTMSS SVTVPSSTWP SQTVTCSVAH PASSTTVDKK LEPSGPISTI   240
NPCPPCKECH KCPAPNLEGG PSVFIFPPNI KDVLMISLTP KVTCVVVDVS EDDPDVRISW   300
FVNNVEVHTA QTQTHREDYN STIRVVSALP IQHQDWMSGK EFKCKVNNKD LPSPIERTIS   360
KIKGLVRAPQ VYILPPPAEQ LSRKDVSLTC LVVGFNPGDI SVEWTSNGHT EENYKDTAPV   420
LDSDGSYFIY SKLDIKTSKW EKTDSFSCNV RHEGLKNYYL KKTISRSPGK              470

SEQ ID NO: 2            moltype = AA   length = 234
FEATURE                 Location/Qualifiers
source                  1..234
                        mol_type = protein
                        organism = synthetic construct
SEQUENCE: 2
MESQIQVFVF VFLWLSGVDG DIVMTQSHKF MSTSVGDRVS ITCKASQDVR NTVAWYQQKT    60
GQSPKLLIYS SSYRNTGVPD RFTGSGSGTD FTFTISSVQA EDLAVYFCQQ HYITPYTFGG   120
GTKLEIKRAD AAPTVSIFPP SSEQLTSGGA SVVCFLNNFY PKDINVKWKI DGSERQNGVL   180
NSWTDQDSKD STYSMSSTLT LTKDEYERHN SYTCEATHKT STSPIVKSFN RNEC         234

SEQ ID NO: 3            moltype = AA   length = 115
FEATURE                 Location/Qualifiers
source                  1..115
                        mol_type = protein
                        organism = synthetic construct
SEQUENCE: 3
QVQLKESGPG LVAPSQSLSI TCTVSGFSLL SYGVHWVRQP PGKGLEWLGV IWTGGTTNYN    60
SALMSRLSIS KDDSKSQVFL KMNSLQTDDT AIYYCARYYY GMDYWGQGTS VTVSS        115

SEQ ID NO: 4            moltype = AA   length = 115
FEATURE                 Location/Qualifiers
source                  1..115
                        mol_type = protein
                        organism = synthetic construct
SEQUENCE: 4
QVQLQESGPG LVKPSETLSL TCTVSGFSLL SYGVHWVRQP PGKGLEWLGV IWTGGTTNYN    60
SALMSRLTIS KDDSKSTVYL KMNSLKTEDT AIYYCARYYY GMDYWGQGTS VTVSS        115

SEQ ID NO: 5            moltype = AA   length = 115
FEATURE                 Location/Qualifiers
source                  1..115
                        mol_type = protein
                        organism = synthetic construct
SEQUENCE: 5
QVQLQESGPG LVKPSETLSL TCTVSGFSLL SYGVHWVRQP PGKGLEWLGV IWTGGTTNYN    60
SALMSRLTIS KDDSKNTVYL KMNSLKTEDT AIYYCARYYY GMDYWGQGTL VTVSS        115

SEQ ID NO: 6            moltype = AA   length = 107
FEATURE                 Location/Qualifiers
source                  1..107
                        mol_type = protein
                        organism = synthetic construct
SEQUENCE: 6
DIQMTQSPSS LSASVGDRVT ITCKASQDVR NTVAWYQQKP GKAPKLLIYS SSYRNTGVPD    60
RFSGSGSGTD FTLTISSLQA EDVAVYFCQQ HYITPYTFGG GTKVEIK                 107

SEQ ID NO: 7            moltype = AA   length = 107
FEATURE                 Location/Qualifiers
source                  1..107
                        mol_type = protein
                        organism = synthetic construct
SEQUENCE: 7
DIQMTQSPSS LSASVGDRVT ITCKASQDVR NTVAWYQQKP GKAPKLLIYS SSYRNTGVPD    60
RFSGSGSGTD FTLTISSLQA EDVAVYYCQQ HYITPYTFGG GTKVEIK                 107

SEQ ID NO: 8            moltype = AA   length = 10
FEATURE                 Location/Qualifiers
source                  1..10
                        mol_type = protein
                        organism = synthetic construct
SEQUENCE: 8
```

-continued

```
GFSLLSYGVH                                                                10

SEQ ID NO: 9              moltype = AA   length = 16
FEATURE                   Location/Qualifiers
source                    1..16
                          mol_type = protein
                          organism = synthetic construct
SEQUENCE: 9
VIWTGGTTNY NSALMS                                                         16

SEQ ID NO: 10             moltype = AA   length = 7
FEATURE                   Location/Qualifiers
source                    1..7
                          mol_type = protein
                          organism = synthetic construct
SEQUENCE: 10
YYYGMDY                                                                   7

SEQ ID NO: 11             moltype = AA   length = 11
FEATURE                   Location/Qualifiers
source                    1..11
                          mol_type = protein
                          organism = synthetic construct
SEQUENCE: 11
KASQDVRNTV A                                                              11

SEQ ID NO: 12             moltype = AA   length = 7
FEATURE                   Location/Qualifiers
source                    1..7
                          mol_type = protein
                          organism = synthetic construct
SEQUENCE: 12
SSSYRNT                                                                   7

SEQ ID NO: 13             moltype = AA   length = 9
FEATURE                   Location/Qualifiers
source                    1..9
                          mol_type = protein
                          organism = synthetic construct
SEQUENCE: 13
QQHYITPYT                                                                 9

SEQ ID NO: 14             moltype = AA   length = 707
FEATURE                   Location/Qualifiers
source                    1..707
                          mol_type = protein
                          organism = Homo sapiens
SEQUENCE: 14
MSLWQPLVLV LLVLGCCFAA PRQRQSTLVL FPGDLRTNLT DRQLAEEYL  RYGYTRVAEM         60
RGESKSLGPA LLLLQKQLSL PETGELDSAT LKAMRTPRCG VPDLGRFQTF EGDLKWHHHN        120
ITYWIQNYSE DLPRAVIDDA FARAFALWSA VTPLTFTRVY SRDADIVIQF GVAEHGDGYP        180
FDGKDGLLAH AFPPGPGIQG DAHFDDDELW SLGKGVVVPT RFGNADGAAC HFPPFIFEGRS       240
YSACTTDGRS DGLPWCSTTA NYDTDDRFGF CPSERLYTRD GNADGKPCQF PFIFQGQSYS        300
ACTTDGRSDG YRWCATTANY DRDKLFGFCP TRADSTVMGG NSAGELCVFP FTFLGKEYST        360
CTSEGRGDGR LWCATTSNFD SDKKWGFCPD QGYSLFLVAA HEFGHALGLD HSSVPEALMY        420
PMYRFTEGPP LHKDDVNGIR HLYGPRPEPE PRPPTTTTPQ PTAPPTVCPT GPPTVHPSER        480
PTAGPTGPPS AGPTGPPTAG PSTATTVPLS PVDDACNVNI FDAIAEIGNQ LYLFKDGKYW        540
RFSEGRGSRP QGPFLIADKW PALPRKLDSV FEEPLSKKLF FFSGRQVWVY TGASVLGPRR        600
LDKLGLGADV AQVTGALRSG RGKMLLFSGR RLWRFDVKAQ MVDPRSASEV DRMFPGVPLD        660
THDVFQYREK AYFCQDRFYW RVSSRSELNQ VDQVGYVTYD ILQCPED                     707

SEQ ID NO: 15             moltype = AA   length = 688
FEATURE                   Location/Qualifiers
source                    1..688
                          mol_type = protein
                          organism = Homo sapiens
SEQUENCE: 15
APRQRQSTLV LFPGDLRTNL TDRQLAEEYL YRYGYTRVAE MRGESKSLGP ALLLLQKQLS         60
LPETGELDSA TLKAMRTPRC GVPDLGRFQT FEGDLKWHHH NITYWIQNYS EDLPRAVIDD        120
AFARAFALWS AVTPLTFTRV YSRDADIVIQ FGVAEHGDGY PFDGKDGLLA HAFPPGPGIQ        180
GDAHFDDDEL WSLGKGVVVP TRFGNADGAA CHFPPFIFEGR SYSACTTDGR SDGLPWCSTT       240
ANYDTDDRFG FCPSERLYTR DGNADGKPCQ FPFIFQGQSY SACTTDGRSD GYRWCATTAN        300
YDRDKLFGFC PTRADSTVMG GNSAGELCVF PFTFLGKEYS TCTSEGRGDG RLWCATTSNF        360
DSDKKWGFCP DQGYSLFLVA AHEFGHALGL DHSSVPEALM YPMYRFTEGP PLHKDDVNGI        420
RHLYGPRPEP EPRPPTTTTP QPTAPPTVCP TGPPTVHPSE RPTAGPTGPP SAGPTGPPTA        480
GPSTATTVPL SPVDDACNVN IFDAIAEIGN QLYLFKDGKY WRFSEGRGSR PQGPFLIADK        540
WPALPRKLDS VFEEPLSKKL FFFSGRQVWV YTGASVLGPR RLDKLGLGAD VAQVTGALRS        600
GRGKMLLFSG RRLWRFDVKA QMVDPRSASE VDRMFPGVPL DTHDVFQYRE KAYFCQDRFY        660
WRVSSRSELN QVDQVGYVTY DILQCPED                                          688
```

```
SEQ ID NO: 16           moltype = AA   length = 19
FEATURE                 Location/Qualifiers
source                  1..19
                        mol_type = protein
                        organism = Homo sapiens
SEQUENCE: 16
MSLWQPLVLV LLVLGCCFA                                                    19

SEQ ID NO: 17           moltype = AA   length = 470
FEATURE                 Location/Qualifiers
source                  1..470
                        mol_type = protein
                        organism = synthetic construct
SEQUENCE: 17
MAVLVLFLCL VAFPSCVLSQ VQLKESGPGL VAPSQSLSIT CTVSGFSLLS YGVHWVRQPP        60
GKGLEWLGVI WTGGSTNYNS ALMSRLSISK DDSKSQVFLK MNSLQTDDTA MYYCARYYYA       120
MDYWGQGTSV TVSSAKTTPP SVYPLAPGCG DTTGSSVTLG CLVKGYFPES VTVTWNSGSL       180
SSSVHTFPAL LQSGLYTMSS SVTVPSSTWP SQTVTCSVAH PASSTTVDKK LEPSGPISTI       240
NPCPPCKECH KCPAPNLEGG PSVFIFPPNI KDVLMISLTP KVTCVVVDVS EDDPDVRISW       300
FVNNVEVHTA QTQTHREDYN STIRVVSALP IQHQDWMSGK EFKCKVNNKD LPSPIERTIS       360
KIKGLVRAPQ VYILPPPAEQ LSRKDVSLTC LVVGFNPGDI SVEWTSNGHT EENYKDTAPV       420
LDSDGSYFIY SKLDIKTSKW EKTDSFSCNV RHEGLKNYYL KKTISRSPGK                  470

SEQ ID NO: 18           moltype = AA   length = 234
FEATURE                 Location/Qualifiers
source                  1..234
                        mol_type = protein
                        organism = synthetic construct
SEQUENCE: 18
MESQIQVFVF VFLWLSGVDG DIVMTQSHKF MFTSVGDRVS ITCKASQDVR NTVAWYQQKT        60
GQSPKLLIYS ASYRNTGVPD RFTGSISGTD FTFTISSVQA EDLALYYCQQ HYSTPYTFGG       120
GTKLEVKRAD AAPTVSIFPP SSEQLTSGGA SVVCFLNNFY PKDINVKWKI DGSERQNGVL       180
NSWTDQDSKD STYSMSSTLT LTKDEYERHN SYTCEATHKT STSPIVKSFN RNEC             234

SEQ ID NO: 19           moltype = AA   length = 115
FEATURE                 Location/Qualifiers
source                  1..115
                        mol_type = protein
                        organism = synthetic construct
SEQUENCE: 19
QVQLKESGPG LVAPSQSLSI TCTVSGFSLL SYGVHWVRQP PGKGLEWLGV IWTGGSTNYN        60
SALMSRLSIS KDDSKSQVFL KMNSLQTDDT AMYYCARYYY AMDYWGQGTS VTVSS            115

SEQ ID NO: 20           moltype = AA   length = 107
FEATURE                 Location/Qualifiers
source                  1..107
                        mol_type = protein
                        organism = synthetic construct
SEQUENCE: 20
DIVMTQSHKF MFTSVGDRVS ITCKASQDVR NTVAWYQQKT GQSPKLLIYS ASYRNTGVPD        60
RFTGSISGTD FTFTISSVQA EDLALYYCQQ HYSTPYTFGG GTKLEVK                     107

SEQ ID NO: 21           moltype = AA   length = 10
FEATURE                 Location/Qualifiers
source                  1..10
                        mol_type = protein
                        organism = synthetic construct
SEQUENCE: 21
GFSLLSYGVH                                                              10

SEQ ID NO: 22           moltype = AA   length = 16
FEATURE                 Location/Qualifiers
source                  1..16
                        mol_type = protein
                        organism = synthetic construct
SEQUENCE: 22
VIWTGGSTNY NSALMS                                                       16

SEQ ID NO: 23           moltype = AA   length = 7
FEATURE                 Location/Qualifiers
source                  1..7
                        mol_type = protein
                        organism = synthetic construct
SEQUENCE: 23
YYYAMDY                                                                 7

SEQ ID NO: 24           moltype = AA   length = 11
FEATURE                 Location/Qualifiers
```

```
source                   1..11
                         mol_type = protein
                         organism = synthetic construct
SEQUENCE: 24
KASQDVRNTV A                                                           11

SEQ ID NO: 25            moltype = AA   length = 7
FEATURE                  Location/Qualifiers
source                   1..7
                         mol_type = protein
                         organism = synthetic construct
SEQUENCE: 25
SASYRNT                                                                7

SEQ ID NO: 26            moltype = AA   length = 9
FEATURE                  Location/Qualifiers
source                   1..9
                         mol_type = protein
                         organism = synthetic construct
SEQUENCE: 26
QQHYSTPYT                                                              9

SEQ ID NO: 27            moltype = AA   length = 229
FEATURE                  Location/Qualifiers
source                   1..229
                         mol_type = protein
                         organism = synthetic construct
SEQUENCE: 27
QVFVYMLLWL SGVDGDIVMT QSQKFMSTSV GDRVSVTCKA SQNVGTNVAW YQQKPGQSPK      60
ALIYSASYRF SGVPDRFTGS GSGTDFTLTI SNVQSEDLAE YFCQQYNSYP YTFGGGTKLE     120
IKRADAAPTV SIFPPSSEQL TSGGASVVCF LNNFYPKDIN VKWKIDGSER QNGVLNSWTD     180
QDSKDSTYSM SSTLTLTKDE YERHNSYTCE ATHKTSTSPI VKSFNRNEC                 229

SEQ ID NO: 28            moltype = AA   length = 107
FEATURE                  Location/Qualifiers
source                   1..107
                         mol_type = protein
                         organism = synthetic construct
SEQUENCE: 28
DIVMTQSQKF MSTSVGDRVS VTCKASQNVG TNVAWYQQKP GQSPKALIYS ASYRFSGVPD      60
RFTGSGSGTD FTLTISNVQS EDLAEYFCQQ YNSYPYTFGG GTKLEIK                   107

SEQ ID NO: 29            moltype = AA   length = 11
FEATURE                  Location/Qualifiers
source                   1..11
                         mol_type = protein
                         organism = synthetic construct
SEQUENCE: 29
KASQNVGTNV A                                                           11

SEQ ID NO: 30            moltype = AA   length = 7
FEATURE                  Location/Qualifiers
source                   1..7
                         mol_type = protein
                         organism = synthetic construct
SEQUENCE: 30
SASYRFS                                                                7

SEQ ID NO: 31            moltype = AA   length = 9
FEATURE                  Location/Qualifiers
source                   1..9
                         mol_type = protein
                         organism = synthetic construct
SEQUENCE: 31
QQYNSYPYT                                                              9

SEQ ID NO: 32            moltype = AA   length = 233
FEATURE                  Location/Qualifiers
source                   1..233
                         mol_type = protein
                         organism = synthetic construct
SEQUENCE: 32
MSSAQFLGLL LLCFQGTRCD IQMTQTTSSL SASLGDRVTI SCSASQGISN YLNWYQQKPD      60
GTFKLLIYYT SILHSGVPSR FSGSGSGTDY SLTISNLEPE DIATYYCQQY GWLPRTFGGG     120
TKLEIKRADA APTVSIFPPS SEQLTSGGAS VVCFLNNFYP KDINVKWKID GSERQNGVLN     180
SWTDQDSKDS TYSMSSTLTL TKDEYERHNS YTCEATHKTS TSPIVKSFNR NEC            233

SEQ ID NO: 33            moltype = AA   length = 460
FEATURE                  Location/Qualifiers
```

```
source                 1..460
                       mol_type = protein
                       organism = synthetic construct
SEQUENCE: 33
MGWSSIILFL VATATGVHSQ VQLQQPGSVL VRPGASVKLS CTASGYTFTS YWMNWVKQRP   60
GQGLEWIGEI YPISGRTNYN EKFKVKATLT VDTSSSTAYM DLNSLTSEDS AVYYCARSRA  120
NWDDYWGQGT TLTVSSAKTT PPSVYPLAPG SAAQTNSMVT LGCLVKGYFP EPVTVTWNSG  180
SLSSGVHTFP AVLQSDLYTL SSSVTVPSST WPSETVTCNV AHPASSTKVD KKIVPRDCGC  240
KPCICTVPEV SSVFIFPPKP KDVLTITLTP KVTCVVVDIS KDDPEVQFSW FVDDVEVHTA  300
QTQPREEQFN STFRSVSELP IMHQDWLNGK EFKCRVNSAA FPAPIEKTIS KTKGRPKAPQ  360
VYTIPPPKEQ MAKDKVSLTC MITDFFPEDI TVEWQWNGQP AENYKNTQPI MDTDGSYFVY  420
SKLNVQKSNW EAGNTFTCSV LHEGLHNHHT EKSLSHSPGK                        460

SEQ ID NO: 34          moltype = AA  length = 108
FEATURE                Location/Qualifiers
source                 1..108
                       mol_type = protein
                       organism = synthetic construct
SEQUENCE: 34
DIQMTQTTSS LSASLGDRVT ISCSASQGIS NYLNWYQQKP DGTFKLLIYY TSILHSGVPS   60
RFSGSGSGTD YSLTISNLEP EDIATYYCQQ YGWLPRTFGG GTKLEIKR               108

SEQ ID NO: 35          moltype = AA  length = 461
FEATURE                Location/Qualifiers
source                 1..461
                       mol_type = protein
                       organism = synthetic construct
SEQUENCE: 35
MGWSLILLFL VAVATRVHSQ VQLQESGPGL VKPSETLSLT CTVSGFSLLS YGVHWVRQPP   60
GKGLEWLGVI WTGGTTNYNS ALMSRFTISK DDSKNTVYLK MNSLKTEDTA IYYCARYYYG  120
MDYWGQGTLV TVSSASTKGP SVFPLAPCSR STSESTAALG CLVKDYFPEP VTVSWNSGAL  180
TSGVHTFPAV LQSSGLYSLS SVVTVPSSSL GTKTYTCNVD HKPSNTKVDK RVESKYGPPC  240
PPCPAPEFLG GPSVFLFPPK PKDTLMISRT PEVTCVVVDV SQEDPEVQFN WYVDGVEVHN  300
AKTKPREEQF NSTYRVVSVL TVLHQDWLNG KEYKCKVSNK GLPSSIEKTI SKAKGQPREP  360
QVYTLPPSQE EMTKNQVSLT CLVKGFYPSD IAVEWESNGQ PENNYKTTPP VLDSDGSFFL  420
YSRLTVDKSR WQEGNVFSCS VMHEALHNHY TQKSLSLSLG K                      461

SEQ ID NO: 36          moltype = AA  length = 234
FEATURE                Location/Qualifiers
source                 1..234
                       mol_type = protein
                       organism = synthetic construct
SEQUENCE: 36
MRVPAQLLGL LLLWLPGARC DIQMTQSPSS LSASVGDRVT ITCKASQDVR NTVAWYQQKP   60
GKAPKLLIYS SSYRNTGVPD RFSGSGSGTD FTLTISSLQA EDVAVYYCQQ HYITPYTFGG  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 37          moltype = AA  length = 148
FEATURE                Location/Qualifiers
source                 1..148
                       mol_type = protein
                       organism = synthetic construct
SEQUENCE: 37
MESQIQVFVF VFLWLSGVDG DIVMTQSHKF MFTSVGDRVS ITCKASQDVR NTVAWYQQKT   60
GQSPKLLIYS ASYRNTGVPD RFTGSISGTD FTFTISSVQA EDLALYYCQQ HYSTPYTFGG  120
GTKLEVKRAD AAPTVSIFPP SSEQLTSG                                     148

SEQ ID NO: 38          moltype = AA  length = 143
FEATURE                Location/Qualifiers
source                 1..143
                       mol_type = protein
                       organism = synthetic construct
SEQUENCE: 38
QVFVYMLLWL SGVDGDIVMT QSQKFMSTSV GDRVSVTCKA SQNVGTNVAW YQQKPGQSPK   60
ALIYSASYRF SGVPDRFTGS GSGTDFTLTI SNVQSEDLAE YFCQQYNSYP YTFGGGTKLE  120
IKRADAAPTV SIFPPSSEQL TSG                                          143

SEQ ID NO: 39          moltype = AA  length = 180
FEATURE                Location/Qualifiers
source                 1..180
                       mol_type = protein
                       organism = synthetic construct
SEQUENCE: 39
MAVLVLFLCL VAFPSCVLSQ VQLKESGPGL VAPSQSLSIT CTVSGFSLLS YGVHWVRQPP   60
GKGLEWLGVI WTGGSTNYNS ALMSRLSISK DDSKSQVFLK MNSLQTDDTA MYYCARYYYA  120
MDYWGQGTSV TVSSAKTTPP SVYPLAPGCG DTTGSSVTLG CLVKGYFPES VTVTWNSGSL  180

SEQ ID NO: 40          moltype = AA  length = 7
```

```
FEATURE                 Location/Qualifiers
source                  1..7
                        mol_type = protein
                        organism = synthetic construct
SEQUENCE: 40
FQTFEGD                                                                 7

SEQ ID NO: 41           moltype = AA  length = 6
FEATURE                 Location/Qualifiers
source                  1..6
                        mol_type = protein
                        organism = synthetic construct
SEQUENCE: 41
QTFEGD                                                                  6

SEQ ID NO: 42           moltype = AA  length = 13
FEATURE                 Location/Qualifiers
source                  1..13
                        mol_type = protein
                        organism = synthetic construct
SEQUENCE: 42
VPDLGRFQTF EGD                                                         13

SEQ ID NO: 43           moltype = AA  length = 439
FEATURE                 Location/Qualifiers
source                  1..439
                        mol_type = protein
                        organism = synthetic construct
SEQUENCE: 43
QSVEESGGRL VTPGTPLTLT CTASGFTISS YHMTWVRQAP MKGLEWIGTI SSSGSTYYAS       60
WAKGRFTISK TSSTTVDLKI TSPATEDTAT YFCARSVPGD SSGEIWGRGT LVTVSSGQPK      120
APSVFPLAPC CGDTPSSTVT LGCLVKGYLP EPVTVTWNSG TLTNGVRTFP SVRQSSGLYS      180
LSSVVSVTSS SQPVTCNVAH PATNTKVDKT VAPSTCSKPT CPPPELLGGP SVFIFPPKPK      240
DTLMISRTPE VTCVVVDVSQ DDPEVQFTWY INNEQVRTAR PPLREQQFNS TIRVVSTLPI      300
AHQDWLRGKE FKCKVHNKAL PAPIEKTISK ARGQPLEPKV YTMGPPREEL SSRSVSLTCM      360
INGFYPSDIS VEWEKNGKAE DNYKTTPAVL DSDGSYFLYS KLSVPTSEWQ RGDVFTCSVM      420
HEALHNHYTQ KSISRSPGK                                                  439

SEQ ID NO: 44           moltype = AA  length = 217
FEATURE                 Location/Qualifiers
source                  1..217
                        mol_type = protein
                        organism = synthetic construct
SEQUENCE: 44
AQVLTQTASP VSAAVGGTVT INCQSSQSVY NKNWLAWYQQ KPGQPPKRLI YSASTLDSGV       60
SSRFKGSGSG TQFTLTISGV QCDDAATYYC QGEFSCSRGD CSAFGGGTEV VVQGDPVAPT      120
VLIFPPSADL VATGTTVIVC VANKYFPDVT VTWEVDGTTQ TTGIENSKTP QNSADCTYNL      180
SSTLTLTSTQ YNSHKEYTCK VTQGTTSVVQ SFNRGDC                              217

SEQ ID NO: 45           moltype = AA  length = 10
FEATURE                 Location/Qualifiers
source                  1..10
                        mol_type = protein
                        organism = synthetic construct
SEQUENCE: 45
VIWTGGSTNY                                                             10

SEQ ID NO: 46           moltype = AA  length = 116
FEATURE                 Location/Qualifiers
source                  1..116
                        mol_type = protein
                        organism = synthetic construct
SEQUENCE: 46
QVQLKESGPG LVAPSQSLSI TCTVSGFSLL SYGVIIWVRQ PPGKGLEWLG VIWTGGTTNY       60
NSALMSRLSI SKDDSKSQVF LKMNSLQTDD TAIYYCARYY YGMDYWGQGT SVTVSS          116

SEQ ID NO: 47           moltype = AA  length = 108
FEATURE                 Location/Qualifiers
source                  1..108
                        mol_type = protein
                        organism = synthetic construct
SEQUENCE: 47
DIVMTQSHKF MSTSVGDRVS ITCKASQDVR NTVAWYQQKT GQSPKLLIYS SSYRNTGVPD       60
RFTGSGSGTD FTFTISSVQA EDLAVYFCQQ HYITPYTFGG GTKLEIKR                  108

SEQ ID NO: 48           moltype = AA  length = 116
FEATURE                 Location/Qualifiers
source                  1..116
                        mol_type = protein
```

```
                        organism = synthetic construct
SEQUENCE: 48
QVQLQESGPG LVKPSETLSL TCTVSGFSLL SYGVIIWVRQ PPGKGLEWLG VIWTGGTTNY    60
NSALMSRLTI SKDDSKSTVY LKMNSLKTED TAIYYCARYY YGMDYWGQGT SVTVSS        116

SEQ ID NO: 49           moltype = AA  length = 230
FEATURE                 Location/Qualifiers
source                  1..230
                        mol_type = protein
                        organism = synthetic construct
SEQUENCE: 49
MSSAQFLGLL LLCFQGTRCD IQMTQTTSSL SASLGDRVTI SCSASQGISN YLNWYQQKPD    60
GTFKLLIYYT SILIISGVPS RFSGSGSGTD YSLTISNLEP EDIATYYCQQ YGWLPRTFGG   120
GTKLEIKRAD AAPTVSIFPP SEQLTSGGAS VVCFLNNFYP KDINVKWKID GSERQNGVLN   180
SWTDQDSKDS TYSMSSTLTL TKDEYERHSY TCEATHKTSP IVKSFNRNEC              230

SEQ ID NO: 50           moltype = AA  length = 460
FEATURE                 Location/Qualifiers
source                  1..460
                        mol_type = protein
                        organism = synthetic construct
SEQUENCE: 50
MGWSSIILLT VATATGVHSQ VQLQQPGSVL VRPGASVKLS CTASGYTFTS YWMNWVKQRP    60
GQGLEWIGEI YPISGRTNYN EKFKVKATLT VDTSSSTAYM DLNSLTSEDS AVYYCARSRA   120
NWDDYWGQGT TLTVSSAKTT PPSVYPLAPG SAAQTNSMVT LCLVKGYFPE PVTVTWNSGS   180
LSSGVHTFPA VLQSDLYTLS SSVTVPSSTW PSETVTCNVA HPASSTKVDK KIVPRDCGCK   240
PCICTVPEVS SVFIFPPKPK DVLTITLTPK VTCVVVDISK DDPEVQFSWF VDDVEVHTAQ   300
TQPREEQFNS TFRSVSELPI MHQDWLNGKE FKCRVNSAAF PAPIEKTISK TKGRPKAPQV   360
YTIPPPKEQM AKDKVSLTCM ITDFFPEDIT VEWQWNGQPA ENTYKNTQPI MDTDGSYFVY   420
SKLNVQKSNW EAGNTFTCSV LHEGLHNHHT EKSLSHSPGK                         460

SEQ ID NO: 51           moltype = AA  length = 117
FEATURE                 Location/Qualifiers
source                  1..117
                        mol_type = protein
                        organism = synthetic construct
SEQUENCE: 51
QVQLQQPGSV LVRPGASVKL SCTASGYTFT SYWMNWVKQR PGQGLEWIGE IYPISGRTNY    60
NEKFKVKATL TVDTSSSTAY MDLNSLTSED SAVYYCARSR ANWDDYWGQG TTLTVSS      117

SEQ ID NO: 52           moltype = AA  length = 107
FEATURE                 Location/Qualifiers
source                  1..107
                        mol_type = protein
                        organism = synthetic construct
SEQUENCE: 52
DIQMTQTTSS LSASLGDRVT ISCSASQGIS NYLNWYQQKP DGTFKLLIYY TSILHSGVPS    60
RESGSGSGTD YSLTISNLEP EDIATYYCQQ YGWLPRTFGG GTKLEIK                 107

SEQ ID NO: 53           moltype = AA  length = 116
FEATURE                 Location/Qualifiers
source                  1..116
                        mol_type = protein
                        organism = synthetic construct
SEQUENCE: 53
QVQLQESGPG LVKPSETLSL TCTVSGFSLL SYGVIIWVRQ PPGKGLEWLG VIWTGGTTNY    60
NSALMSRLTI SKDDSKSTVY LKMNSLKTED TAIYYCARYY YGMDYWGQGT SVTVSS       116

SEQ ID NO: 54           moltype = AA  length = 114
FEATURE                 Location/Qualifiers
source                  1..114
                        mol_type = protein
                        organism = synthetic construct
SEQUENCE: 54
QVQLQESGPG LVKPSETLSL TCTVSGFSLL SYGVHWVRQP PGKGLEWLGV IWTGGTNYNS    60
ALMSRLTISK DDSKNTVYLK MNSLKTEDTA IYYCARYYYG MDYWGQGTLV TVSS         114

SEQ ID NO: 55           moltype = AA  length = 115
FEATURE                 Location/Qualifiers
source                  1..115
                        mol_type = protein
                        organism = synthetic construct
SEQUENCE: 55
QVQLQESGPG LVKPSETLSL TCTVSGFSLL SYGVHWVRQP PGKGLEWLGV IWTGGTTNYN    60
SALMSRFTIS KDDSKNTVYL KMNSLKTEDT AIYYCARYYY GMDYWGQGTL VTVSS        115

SEQ ID NO: 56           moltype = AA  length = 115
FEATURE                 Location/Qualifiers
source                  1..115
```

```
                        mol_type = protein
                        organism = synthetic construct
SEQUENCE: 56
QVQLQESGPG LVKPSETLSL TCTVSGFSLL SYGVHWVRQP PGKGLEWLGV IWTGGTTNYN    60
SALMSRFTIS KDDSKNTLYL KMNSLKTEDT AIYYCARYYY GMDYWGQGTL VTVSS         115

SEQ ID NO: 57           moltype = AA  length = 107
FEATURE                 Location/Qualifiers
source                  1..107
                        mol_type = protein
                        organism = synthetic construct
SEQUENCE: 57
DIVMTQSPSF LSASVGDRVT ITCKASQDVR NTVAWYQQKT GKAPKLLIYS SSYRNTGVPD    60
RFTGSGSGTD FTLTISSLQA EDVAVYFCQQ HYITPYTFGG GTKVEIK                  107

SEQ ID NO: 58           moltype = AA  length = 107
FEATURE                 Location/Qualifiers
source                  1..107
                        mol_type = protein
                        organism = synthetic construct
SEQUENCE: 58
DIVMTQSPSS LSASVGDRVT ITCKASQDVR NTVAWYQQKP GKAPKLLIYS SSYRNTGVPD    60
RFTGSGSGTD FTLTISSLQA EDVAVYFCQQ HYITPYTFGG GTKVEIK                  107

SEQ ID NO: 59           moltype = AA  length = 108
FEATURE                 Location/Qualifiers
source                  1..108
                        mol_type = protein
                        organism = synthetic construct
SEQUENCE: 59
DIQMTQSPSS LSASVGDRVT ITCKASQDVR NTVAWYQQKP GKAPKLLITY SSSYRNTGVP    60
DRFSGSGSGT DFTLTISSLQ AEDVAVYFCQ QHYITPYTFG GGTKVEIK                 108

SEQ ID NO: 60           moltype = AA  length = 108
FEATURE                 Location/Qualifiers
source                  1..108
                        mol_type = protein
                        organism = synthetic construct
SEQUENCE: 60
DIQMTQSPSS LSASVGDRVT ITCKASQDVR NTVAWYQQKP GKAPKLLITY SSSYRNTGVP    60
DRFSGSGSGT DFTLTISSLQ AEDVAVYYCQ QHYITPYTFG GGTKVEIK                 108

SEQ ID NO: 61           moltype = AA  length = 39
FEATURE                 Location/Qualifiers
source                  1..39
                        mol_type = protein
                        organism = synthetic construct
SITE                    3
                        note = hydroxyproline
SITE                    6
                        note = hydroxyproline
SITE                    9
                        note = hydroxyproline
SITE                    12
                        note = hydroxyproline
SITE                    16
                        note = glycine phosphinate; Psi-
(R,S)
SITE                    30
                        note = hydroxyproline
SITE                    33
                        note = hydroxyproline
SITE                    36
                        note = hydroxyproline
SITE                    39
                        note = amidated hydroxyproline
SEQUENCE: 61
GPPGPPGPPG PPGPPGVVGE QGEQGPPGPP GPPGPPGPP                            39

SEQ ID NO: 62           moltype = AA  length = 39
FEATURE                 Location/Qualifiers
source                  1..39
                        mol_type = protein
                        organism = synthetic construct
SITE                    3
                        note = hydroxyproline
SITE                    6
                        note = hydroxyproline
SITE                    9
                        note = hydroxyproline
```

```
SITE                      12
                          note = hydroxyproline
SITE                      14
                          note = (2S,4R)-4-methylproline
SITE                      15
                          note = (2S,4R)-4-fluoroproline
SITE                      16
                          note = glycine phosphinate; Psi-
(R,S)
SITE                      30
                          note = hydroxyproline
SITE                      32
                          note = (2S,4R)-4-methylproline
SITE                      33
                          note = (2S,4R)-4-fluoroproline
SITE                      36
                          note = hydroxyproline
SITE                      39
                          note = amidated hydroxyproline
SEQUENCE: 62
GPPGPPGPPG PPGPPGVVGE QGEQGPPGPP GPPGPPGPP                              39

SEQ ID NO: 63             moltype = RNA   length = 20
FEATURE                   Location/Qualifiers
source                    1..20
                          mol_type = other RNA
                          organism = synthetic construct
SEQUENCE: 63
tacatgagcg cttccggcac                                                  20

SEQ ID NO: 64             moltype = RNA   length = 20
FEATURE                   Location/Qualifiers
source                    1..20
                          mol_type = other RNA
                          organism = synthetic construct
SEQUENCE: 64
tacatgagcg cctccggcac                                                  20

SEQ ID NO: 65             moltype = RNA   length = 20
FEATURE                   Location/Qualifiers
source                    1..20
                          mol_type = other RNA
                          organism = synthetic construct
SEQUENCE: 65
ttcacccggt tgtggaaact                                                  20

SEQ ID NO: 66             moltype = RNA   length = 19
FEATURE                   Location/Qualifiers
source                    1..19
                          mol_type = other RNA
                          organism = synthetic construct
SEQUENCE: 66
ggggctgcca gggactcat                                                   19

SEQ ID NO: 67             moltype = RNA   length = 25
FEATURE                   Location/Qualifiers
source                    1..25
                          mol_type = other RNA
                          organism = synthetic construct
SEQUENCE: 67
gctttctctc ggtactggaa gacgt                                            25

SEQ ID NO: 68             moltype = RNA   length = 22
FEATURE                   Location/Qualifiers
source                    1..22
                          mol_type = other RNA
                          organism = synthetic construct
SEQUENCE: 68
gctgactacg ataaggacgg ca                                               22

SEQ ID NO: 69             moltype = RNA   length = 21
FEATURE                   Location/Qualifiers
source                    1..21
                          mol_type = other RNA
                          organism = synthetic construct
SEQUENCE: 69
gctcattggt gagggcagag g                                                21

SEQ ID NO: 70             moltype = RNA   length = 24
FEATURE                   Location/Qualifiers
```

```
source                  1..24
                        mol_type = other RNA
                        organism = synthetic construct
SEQUENCE: 70
agacacctct gccctcacca tgag                                              24

SEQ ID NO: 71           moltype = RNA   length = 24
FEATURE                 Location/Qualifiers
source                  1..24
                        mol_type = other RNA
                        organism = synthetic construct
SEQUENCE: 71
aactggatga cgatgtctgc gtcc                                              24

SEQ ID NO: 72           moltype = RNA   length = 19
FEATURE                 Location/Qualifiers
source                  1..19
                        mol_type = other RNA
                        organism = synthetic construct
SEQUENCE: 72
ggagcacgga gacgggtat                                                    19

SEQ ID NO: 73           moltype = RNA   length = 20
FEATURE                 Location/Qualifiers
source                  1..20
                        mol_type = other RNA
                        organism = synthetic construct
SEQUENCE: 73
ctgtctgggg ctcatggtga                                                   20

SEQ ID NO: 74           moltype = RNA   length = 33
FEATURE                 Location/Qualifiers
source                  1..33
                        mol_type = other RNA
                        organism = synthetic construct
SEQUENCE: 74
aatctcgaga gacacctctg ccctcaccat gag                                    33

SEQ ID NO: 75           moltype = RNA   length = 20
FEATURE                 Location/Qualifiers
source                  1..20
                        mol_type = other RNA
                        organism = synthetic construct
SEQUENCE: 75
gtcgtgcgtg tccaaaggca                                                   20

SEQ ID NO: 76           moltype = RNA   length = 21
FEATURE                 Location/Qualifiers
source                  1..21
                        mol_type = other RNA
                        organism = synthetic construct
SEQUENCE: 76
ctatggtcct cgccctgaat t                                                 21

SEQ ID NO: 77           moltype = RNA   length = 19
FEATURE                 Location/Qualifiers
source                  1..19
                        mol_type = other RNA
                        organism = synthetic construct
SEQUENCE: 77
ttcaggggcg accatagtt                                                    19

SEQ ID NO: 78           moltype = RNA   length = 20
FEATURE                 Location/Qualifiers
source                  1..20
                        mol_type = other RNA
                        organism = synthetic construct
SEQUENCE: 78
actactgtgc ctttgagtcc                                                   20

SEQ ID NO: 79           moltype = RNA   length = 20
FEATURE                 Location/Qualifiers
source                  1..20
                        mol_type = other RNA
                        organism = synthetic construct
SEQUENCE: 79
gttggcagtg caatacctga                                                   20

SEQ ID NO: 80           moltype = RNA   length = 22
```

```
FEATURE                 Location/Qualifiers
source                  1..22
                        mol_type = other RNA
                        organism = synthetic construct
SEQUENCE: 80
gtcgccctca aaggtttgga at                                              22

SEQ ID NO: 81           moltype = AA  length = 7
FEATURE                 Location/Qualifiers
source                  1..7
                        mol_type = protein
                        organism = synthetic construct
SEQUENCE: 81
FFAGLDD                                                                7

SEQ ID NO: 82           moltype = AA  length = 10
FEATURE                 Location/Qualifiers
source                  1..10
                        mol_type = protein
                        organism = synthetic construct
CROSSLNK                1..10
                        note = cyclized via cysteine residues
SEQUENCE: 82
CTTHWGFTLC                                                            10

SEQ ID NO: 83           moltype = AA  length = 111
FEATURE                 Location/Qualifiers
source                  1..111
                        mol_type = protein
                        organism = synthetic construct
SEQUENCE: 83
VQLQESGGGL VKPGGSLKLS CAASGFAFST YDMSWIRQTP EKRLEWVATI SSGGSYTYYP      60
DSVKGRFTIS KDNARNTLYL QMSSLRSGDT ALYYCTRFRY DGWYFDVWGQ G              111

SEQ ID NO: 84           moltype = AA  length = 105
FEATURE                 Location/Qualifiers
source                  1..105
                        mol_type = protein
                        organism = synthetic construct
SEQUENCE: 84
DVLITQTPLS LPVSLGDQAS ISCRSSQSIV HSNGNTFLEW YLQKPGQSPK LLIYKVSNRF      60
SGVPDRFSGS GSGTDFTLKI SRVEAEDLGV YYCFQASHVP PTFGG                     105

SEQ ID NO: 85           moltype = AA  length = 5
FEATURE                 Location/Qualifiers
source                  1..5
                        mol_type = protein
                        organism = synthetic construct
SEQUENCE: 85
STYDM                                                                  5

SEQ ID NO: 86           moltype = AA  length = 16
FEATURE                 Location/Qualifiers
source                  1..16
                        mol_type = protein
                        organism = synthetic construct
SEQUENCE: 86
TISSGGSYTY YPDSVK                                                     16

SEQ ID NO: 87           moltype = AA  length = 10
FEATURE                 Location/Qualifiers
source                  1..10
                        mol_type = protein
                        organism = synthetic construct
SEQUENCE: 87
FRYDGWYFDV                                                            10

SEQ ID NO: 88           moltype = AA  length = 16
FEATURE                 Location/Qualifiers
source                  1..16
                        mol_type = protein
                        organism = synthetic construct
SEQUENCE: 88
RSSQSIVHSN GNTFLE                                                     16

SEQ ID NO: 89           moltype = AA  length = 7
FEATURE                 Location/Qualifiers
source                  1..7
                        mol_type = protein
```

```
SEQUENCE: 89
KVSNRFS                                                             7

SEQ ID NO: 90           moltype = AA   length = 9
FEATURE                 Location/Qualifiers
source                  1..9
                        mol_type = protein
                        organism = synthetic construct
SEQUENCE: 90
FQASHVPPT                                                           9

SEQ ID NO: 91           moltype = AA   length = 118
FEATURE                 Location/Qualifiers
source                  1..118
                        mol_type = protein
                        organism = synthetic construct
SEQUENCE: 91
EVQLQQSGPE LVKPGASVKI SCKASGYTFT GYYMHWVKQS PEKSLEWIGE INPSTGGTTY   60
NQKFTGKATL TVDKSSSTAY MQLKSLTSDD SAVYYCASYY RYDWFAYWGQ GTLVTVSA    118

SEQ ID NO: 92           moltype = AA   length = 115
FEATURE                 Location/Qualifiers
source                  1..115
                        mol_type = protein
                        organism = synthetic construct
SEQUENCE: 92
MADVLMTQTP LSLPVSLGDQ ASISCRSSQS LVHSNGNTYL HWYLQKPGQS PKLLIYKVSN   60
RFSGVPDRFS GSGSGTDFTL KISRVEAEDL GVYFCSQSTH VPFTFGSGTK LELKR       115

SEQ ID NO: 93           moltype = AA   length = 5
FEATURE                 Location/Qualifiers
source                  1..5
                        mol_type = protein
                        organism = synthetic construct
SEQUENCE: 93
GYYMH                                                               5

SEQ ID NO: 94           moltype = AA   length = 17
FEATURE                 Location/Qualifiers
source                  1..17
                        mol_type = protein
                        organism = synthetic construct
SEQUENCE: 94
EINPSTGGTT YNQKFTG                                                  17

SEQ ID NO: 95           moltype = AA   length = 9
FEATURE                 Location/Qualifiers
source                  1..9
                        mol_type = protein
                        organism = synthetic construct
SEQUENCE: 95
YYRYDWFAY                                                           9

SEQ ID NO: 96           moltype = AA   length = 16
FEATURE                 Location/Qualifiers
source                  1..16
                        mol_type = protein
                        organism = synthetic construct
SEQUENCE: 96
RSSQSLVHSN GNTYLH                                                   16

SEQ ID NO: 97           moltype = AA   length = 7
FEATURE                 Location/Qualifiers
source                  1..7
                        mol_type = protein
                        organism = synthetic construct
SEQUENCE: 97
KVSNRFS                                                             7

SEQ ID NO: 98           moltype = AA   length = 9
FEATURE                 Location/Qualifiers
source                  1..9
                        mol_type = protein
                        organism = synthetic construct
SEQUENCE: 98
SQSTHVPFT                                                           9

SEQ ID NO: 99           moltype = AA   length = 123
```

```
FEATURE              Location/Qualifiers
source               1..123
                     mol_type = protein
                     organism = synthetic construct
SEQUENCE: 99
QVQLQQSGAE LVMPGASVKM SCKASGYTFT DYWMHWVKQR PGQGLEWIGA IDTSDTYTRY    60
NQKFKGKATL TVDESSSTAY MQASSLTSED SAVYYCARAV IIYGSSWGYF DVWGQGTTVT   120
VSS                                                                 123

SEQ ID NO: 100       moltype = AA  length = 107
FEATURE              Location/Qualifiers
source               1..107
                     mol_type = protein
                     organism = synthetic construct
SEQUENCE: 100
DIELTQSPSY LAASPGETIT INCRASKSIS KYLAWYQEKP GKTNKLLIYS GSTLQSGIPS    60
RFSGSGSGTD FTLTISSLEP EDFAMYYCQQ HNEYPYTFGG GTKLEIK                 107

SEQ ID NO: 101       moltype = AA  length = 5
FEATURE              Location/Qualifiers
source               1..5
                     mol_type = protein
                     organism = synthetic construct
SEQUENCE: 101
DYWMH                                                                 5

SEQ ID NO: 102       moltype = AA  length = 18
FEATURE              Location/Qualifiers
source               1..18
                     mol_type = protein
                     organism = synthetic construct
SEQUENCE: 102
AIDTSDTYTR YYNQKFKG                                                  18

SEQ ID NO: 103       moltype = AA  length = 14
FEATURE              Location/Qualifiers
source               1..14
                     mol_type = protein
                     organism = synthetic construct
SEQUENCE: 103
AVIIYGSSWG YFDV                                                      14

SEQ ID NO: 104       moltype = AA  length = 11
FEATURE              Location/Qualifiers
source               1..11
                     mol_type = protein
                     organism = synthetic construct
SEQUENCE: 104
RASKSISKYL A                                                         11

SEQ ID NO: 105       moltype = AA  length = 7
FEATURE              Location/Qualifiers
source               1..7
                     mol_type = protein
                     organism = synthetic construct
SEQUENCE: 105
SGSTLQS                                                               7

SEQ ID NO: 106       moltype = AA  length = 9
FEATURE              Location/Qualifiers
source               1..9
                     mol_type = protein
                     organism = synthetic construct
SEQUENCE: 106
QQHNEYPYT                                                             9
```

The invention claimed is:

1. A method of treating a genetic heterotopic ossification (gHO) condition in a human subject to reduce or inhibit heterotopic ossification (HO), the method comprising:
administering to the human subject an anti-MMP-9 antibody or an antigen-binding fragment thereof comprising a heavy chain variable region (VH) comprising a heavy chain complementarity determining region 1 (HCDR1) comprising the amino acid sequence of SEQ ID NO: 8, an HCDR2 comprising the amino acid sequence of SEQ ID NO: 9, and an HCDR3 comprising the amino acid sequence of SEQ ID NO: 10, and a light chain variable region comprising a light chain complementarity determining region 1 (LCDR1) comprising the amino acid sequence of SEQ ID NO: 11, an LCDR2 comprising the amino acid sequence of SEQ ID NO: 12, and an LCDR3 comprising the amino acid sequence of SEQ ID NO: 13,
wherein the anti-MMP-9 antibody or antigen-binding fragment thereof is administered to the human subject via subcutaneous administration about every week to every two weeks at a dose of from 15 mg to 150 mg, adjusted for age group, wherein the human subject is aged from about 2 years to under 30 years and having a mutation predisposing the human subject to fibrodysplasia ossificans progressiva (FOP); and wherein administration of the anti-MMP-9 antibody or antigen-binding fragment reduces or inhibits heterotopic ossification (HO) in the subject.

2. The method of claim 1, wherein administration of the anti-MMP-9 antibody or antigen-binding fragment thereof to the human subject results in a reduction in the formation or progression of heterotopic ossification as assessed by one or more of: number of heterotopic ossifications, size of heterotopic ossifications, volume of heterotopic ossifications, growth of heterotopic ossifications, and formation of heterotopic ossifications.

3. The method of claim 1, wherein the anti-MMP-9 antibody or antigen-binding fragment thereof is administered at a dose of about 15 mg, about 25 mg, about 45 mg, about 50 mg, about 75 mg, about 100 mg, or about 150 mg.

4. The method of claim 1, wherein the human subject is aged from about 2 years to about 18 years.

5. The method of claim 1, wherein the human subject is aged from about 2 years to about 5 years.

6. The method of claim 1, wherein the human subject is aged from about 6 years to about 11 years.

7. The method of claim 1, wherein the human subject is aged from about 12 years to about 18 years.

8. A method of treating a genetic heterotopic ossification (gHO) condition in a human subject to reduce or inhibit heterotopic ossification (HO), the method comprising:

administering to the human subject an anti-MMP-9 antibody or an antigen-binding fragment thereof comprising a heavy chain variable region (VH) comprising a heavy chain complementarity determining region 1 (HCDR1) comprising the amino acid sequence of SEQ ID NO: 8, an HCDR2 comprising the amino acid sequence of SEQ ID NO: 9, and an HCDR3 comprising the amino acid sequence of SEQ ID NO: 10, and a light chain variable region comprising a light chain complementarity determining region 1 (LCDR1) comprising the amino acid sequence of SEQ ID NO: 11, an LCDR2 comprising the amino acid sequence of SEQ ID NO: 12, and an LCDR3 comprising the amino acid sequence of SEQ ID NO: 13, wherein the anti-MMP-9 antibody or antigen-binding fragment thereof is administered to the human subject via subcutaneous administration about every week at a dose of:

about 150 mg in a human subject aged 12 years or older;
about 75 mg in a human subject aged about 6 years to about 11 years; and
about 45 mg or 50 mg in a human subject aged about 2 years to about 5 years;

wherein administration of the anti-MMP-9 antibody or antigen-binding fragment thereof reduces or inhibits heterotopic ossification (HO) in the subject.

9. A method of treating a genetic heterotopic ossification (gHO) condition in a human subject to reduce or inhibit heterotopic ossification (HO), the method comprising:

administering to the human subject an anti-MMP-9 antibody or an antigen-binding fragment thereof comprising a heavy chain variable region (VH) comprising a heavy chain complementarity determining region 1 (HCDR1) comprising the amino acid sequence of SEQ ID NO: 8, an HCDR2 comprising the amino acid sequence of SEQ ID NO: 9, and an HCDR3 comprising the amino acid sequence of SEQ ID NO: 10, and a light chain variable region comprising a light chain complementarity determining region 1 (LCDR1) comprising the amino acid sequence of SEQ ID NO: 11, an LCDR2 comprising the amino acid sequence of SEQ ID NO: 12, and an LCDR3 comprising the amino acid sequence of SEQ ID NO: 13, wherein the anti-MMP-9 antibody or antigen-binding fragment thereof is administered to the human subject via subcutaneous administration about every week at a dose of:

about 50 mg in a human subject aged 12 years or older;
about 25 mg in a human subject aged about 6 years to about 11 years; and
about 15 mg in a human subject aged about 2 years to about 5 years;

wherein administration of the anti-MMP-9 antibody or antigen-binding fragment thereof reduces or inhibits heterotopic ossification (HO) in the subject.

10. A method of treating an inflammatory flare-up in a subject having a symptom of genetic fibrodysplasia ossificans progressiva (FOP), comprising:

administering to the subject an anti-MMP-9 antibody or an antigen-binding fragment thereof comprising a heavy chain variable region (VH) comprising a heavy chain complementarity determining region 1 (HCDR1) comprising the amino acid sequence of SEQ ID NO: 8, an HCDR2 comprising the amino acid sequence of SEQ ID NO: 9, and an HCDR3 comprising the amino acid sequence of SEQ ID NO: 10, and a light chain variable region comprising a light chain complementarity determining region 1 (LCDR1) comprising the amino acid sequence of SEQ ID NO: 11, an LCDR2 comprising the amino acid sequence of SEQ ID NO: 12, and an LCDR3 comprising the amino acid sequence of SEQ ID NO: 13, wherein the anti-MMP-9 antibody or antigen-binding fragment thereof is administered to the human subject via subcutaneous administration at a dose of from 15 mg to 150 mg, adjusted for age group, wherein the human subject is aged from about 2 years to under 30 years and having a mutation predisposing the human subject to fibrodysplasia ossificans progressiva (FOP);

wherein the method reduces the frequency of inflammatory flare-ups in the subject as compared to the frequency of inflammatory flare-ups in the subject prior to administration of the MMP-9 inhibitor to the subject.

11. The method of claim 1, wherein the anti-MMP-9 antibody or an antigen-binding fragment comprises a heavy chain variable region (VH) comprising an amino acid sequence having at least 90% sequence identity to the amino acid sequence of SEQ ID NO: 55 and a light chain variable region (VL) comprising an amino acid sequence having at least 90% sequence identity to the amino acid sequence of SEQ ID NO: 7.

12. The method of claim 8, wherein the anti-MMP-9 antibody or an antigen-binding fragment comprises a heavy chain variable region (VH) comprising an amino acid sequence having at least 90% sequence identity to the amino acid sequence of SEQ ID NO: 55 and a light chain variable region (VL) comprising an amino acid sequence having at least 90% sequence identity to the amino acid sequence of SEQ ID NO: 7.

13. The method of claim 8, wherein administration of the anti-MMP-9 antibody or antigen-binding fragment thereof to the human subject results in a reduction in the formation or progression of heterotopic ossification as assessed by one or more of: number of heterotopic ossifications, size of heterotopic ossifications, volume of heterotopic ossifications, growth of heterotopic ossifications, and formation of heterotopic ossifications.

14. The method of claim 9, wherein the anti-MMP-9 antibody or an antigen-binding fragment comprises a heavy chain variable region (VH) comprising an amino acid sequence having at least 90% sequence identity to the amino acid sequence of SEQ ID NO: 55 and a light chain variable region (VL) comprising an amino acid sequence having at least 90% sequence identity to the amino acid sequence of SEQ ID NO: 7.

15. The method of claim 9, wherein administration of the anti-MMP-9 antibody or antigen-binding fragment thereof to the human subject results in a reduction in the formation or progression of heterotopic ossification as assessed by one or more of: number of heterotopic ossifications, size of heterotopic ossifications, volume of heterotopic ossifications, growth of heterotopic ossifications, and formation of heterotopic ossifications.

* * * * *

UNITED STATES PATENT AND TRADEMARK OFFICE
CERTIFICATE OF CORRECTION

PATENT NO. : 12,421,321 B2
APPLICATION NO. : 19/034098
DATED : September 23, 2025
INVENTOR(S) : Pankaj Bhargava et al.

It is certified that error appears in the above-identified patent and that said Letters Patent is hereby corrected as shown below:

In the Specification

Please replace "spondylarthrites" with -- spondyloarthritis -- (Column 3, Line 31).

Please replace "Johnson," with -- Johnsson, -- (Column 25, Line 1).

Please replace "comprising ID" with -- comprising an amino acid having 100% sequence identity to the amino acid sequence of SEQ ID -- (Column 61, Line 7).

Please replace "comprising ID" with -- comprising an amino acid having 100% sequence identity to the amino acid sequence of SEQ ID -- (Column 61, Line 56).

Please replace "comprising ID" with -- comprising an amino acid having 100% sequence identity to the amino acid sequence of SEQ ID -- (Column 62, Line 38).

Please replace "comprising ID" with -- comprising an amino acid having 100% sequence identity to the amino acid sequence of SEQ ID -- (Column 63, Line 20).

Please replace "comprising ID" with -- comprising an amino acid having 100% sequence identity to the amino acid sequence of SEQ ID -- (Column 64, Line 2).

Please replace "comprising ID" with -- comprising an amino acid having 100% sequence identity to the amino acid sequence of SEQ ID -- (Column 64, Line 51).

Please replace "comprising ID" with -- comprising an amino acid having 100% sequence identity to the amino acid sequence of SEQ ID -- (Column 65, Line 33).

Signed and Sealed this
Ninth Day of December, 2025

John A. Squires
*Director of the United States Patent and Trademark Office*

CERTIFICATE OF CORRECTION (continued)
U.S. Pat. No. 12,421,321 B2

Please replace "comprising ID" with -- comprising an amino acid having 100% sequence identity to the amino acid sequence of SEQ ID -- (Column 66, Line 15).

Please replace "comprising ID" with -- comprising an amino acid having 100% sequence identity to the amino acid sequence of SEQ ID -- (Column 66, Line 64).

Please replace "comprising ID" with -- comprising an amino acid having 100% sequence identity to the amino acid sequence of SEQ ID -- (Column 67, Line 46).

Please replace "comprising ID" with -- comprising an amino acid having 100% sequence identity to the amino acid sequence of SEQ ID -- (Column 68, Line 28).

Please replace "comprising ID" with -- comprising an amino acid having 100% sequence identity to the amino acid sequence of SEQ ID -- (Column 69, Line 10).

Please replace "comprising ID" with -- comprising an amino acid having 100% sequence identity to the amino acid sequence of SEQ ID -- (Column 69, Line 59).

Please replace "comprising ID" with -- comprising an amino acid having 100% sequence identity to the amino acid sequence of SEQ ID -- (Column 70, Line 41).

Please replace "comprising ID" with -- comprising an amino acid having 100% sequence identity to the amino acid sequence of SEQ ID -- (Column 71, Line 23).

Please replace "comprising ID" with -- comprising an amino acid having 100% sequence identity to the amino acid sequence of SEQ ID -- (Column 72, Line 5).

Please replace "comprising ID" with -- comprising an amino acid having 100% sequence identity to the amino acid sequence of SEQ ID -- (Column 72, Line 54).

Please replace "comprising ID" with -- comprising an amino acid having 100% sequence identity to the amino acid sequence of SEQ ID -- (Column 73, Line 36).

Please replace "comprising ID" with -- comprising an amino acid having 100% sequence identity to the amino acid sequence of SEQ ID -- (Column 74, Line 19).

Please replace "comprising ID" with -- comprising an amino acid having 100% sequence identity to the amino acid sequence of SEQ ID -- (Column 75, Line 2).

Please replace "comprising ID" with -- comprising an amino acid having 100% sequence identity to the amino acid sequence of SEQ ID -- (Column 75, Line 51).

CERTIFICATE OF CORRECTION (continued)
U.S. Pat. No. 12,421,321 B2

Please replace "comprising ID" with -- comprising an amino acid having 100% sequence identity to the amino acid sequence of SEQ ID -- (Column 76, Line 33).

Please replace "comprising ID" with -- comprising an amino acid having 100% sequence identity to the amino acid sequence of SEQ ID -- (Column 77, Line 15).

Please replace "comprising ID" with -- comprising an amino acid having 100% sequence identity to the amino acid sequence of SEQ ID -- (Column 77, Line 64).

Please replace "comprising ID" with -- comprising an amino acid having 100% sequence identity to the amino acid sequence of SEQ ID -- (Column 78, Line 46).

Please replace "comprising ID" with -- comprising an amino acid having 100% sequence identity to the amino acid sequence of SEQ ID -- (Column 79, Line 28).

Please replace "comprising ID" with -- comprising an amino acid having 100% sequence identity to the amino acid sequence of SEQ ID -- (Column 80, Line 10).

Please replace "comprising ID" with -- comprising an amino acid having 100% sequence identity to the amino acid sequence of SEQ ID -- (Column 82, Line 29).